US012691267B2

(12) United States Patent
Nae et al.

(10) Patent No.: US 12,691,267 B2
(45) Date of Patent: *Jul. 28, 2026

(54) INTERATRIAL SHUNT WITH EXPANDED NECK REGION

(71) Applicant: V-Wave Ltd., Caesarea (IL)

(72) Inventors: Nir Nae, Binyamina (IL); Neal Eigler, Agoura Hills, CA (US); James S. Whiting, Los Angeles, CA (US); Lior Rosen, Zikhron Ya'akov (IL); Werner Hafelfinger, Thousand Oaks, CA (US); Or Mayo, Ramat Gan (IL); Erez Rozenfeld, Shoham (IL)

(73) Assignee: V-Wave Ltd., Caesarea (IL)

( * ) Notice: Subject to any disclaimer, the term of this patent is extended or adjusted under 35 U.S.C. 154(b) by 314 days.

This patent is subject to a terminal disclaimer.

(21) Appl. No.: 18/506,977

(22) Filed: Nov. 10, 2023

(65) Prior Publication Data

US 2024/0075260 A1 Mar. 7, 2024

Related U.S. Application Data

(63) Continuation of application No. 18/300,092, filed on Apr. 13, 2023, now Pat. No. 11,813,386.

(60) Provisional application No. 63/386,147, filed on Dec. 5, 2022, provisional application No. 63/363,015, filed on Apr. 14, 2022.

(51) Int. Cl.
*A61M 27/00* (2006.01)

(52) U.S. Cl.
CPC ... *A61M 27/002* (2013.01); *A61M 2205/0266* (2013.01); *A61M 2207/10* (2013.01)

(58) Field of Classification Search
CPC ........ A61M 27/002; A61M 2205/0266; A61M 2207/10; A61B 17/11
See application file for complete search history.

(56) References Cited

U.S. PATENT DOCUMENTS

| | | | |
|---|---|---|---|
| 744,589 | A | 11/1903 | Moore |
| 3,852,334 | A | 12/1974 | Dusza et al. |
| (Continued) | | | |

FOREIGN PATENT DOCUMENTS

| | | | |
|---|---|---|---|
| AU | 2003291117 B2 | 4/2009 | |
| CA | 2378920 A1 | 2/2001 | |
| (Continued) | | | |

OTHER PUBLICATIONS

U.S. Appl. No. 09/839,643 / U.S. Pat. No. 8,091,556, filed Apr. 20, 2001 / Jan. 10, 2012.

(Continued)

*Primary Examiner* — Philip R Wiest
(74) *Attorney, Agent, or Firm* — Greenberg Traurig, LLP; Christopher C. Bolten; Albert K. Heng

(57) ABSTRACT

Devices are provided with a bridge made of a biocompatible material that surrounds a neck region of an encapsulated shunt. In one embodiment, the bridge is configured to maintain an outer diameter while the diameter of the neck region is reduced or increased in vivo to adjust the fluid flow rate through the device. The bridge may have an outer diameter that is configured to be placed within an enlarged septal hole. Methods for adjusting the flow of fluid and methods for the manufacture of such devices are also provided.

29 Claims, 19 Drawing Sheets

(56) References Cited

U.S. PATENT DOCUMENTS

| 3,874,388 | A | 4/1975 | King et al. |
|---|---|---|---|
| 3,952,334 | A | 4/1976 | Bokros et al. |
| 4,326,304 | A | 4/1982 | Klawitter |
| 4,364,395 | A | 12/1982 | Redmond et al. |
| 4,484,955 | A | 11/1984 | Hochstein |
| 4,601,309 | A | 7/1986 | Chang |
| 4,617,932 | A | 10/1986 | Kornberg |
| 4,662,355 | A | 5/1987 | Pieronne et al. |
| 4,665,906 | A | 5/1987 | Jervis |
| 4,705,507 | A | 11/1987 | Boyles |
| 4,836,204 | A | 6/1989 | Landymore et al. |
| 4,979,955 | A | 12/1990 | Smith |
| 4,988,339 | A | 1/1991 | Vadher |
| 4,995,857 | A | 2/1991 | Arnold |
| 5,035,702 | A | 7/1991 | Taheri |
| 5,035,706 | A | 7/1991 | Giantureo et al. |
| 5,037,427 | A | 8/1991 | Harada et al. |
| 5,089,005 | A | 2/1992 | Harada |
| 5,108,420 | A | 4/1992 | Marks |
| 5,186,431 | A | 2/1993 | Tamari |
| 5,197,978 | A | 3/1993 | Hess |
| 5,234,447 | A | 8/1993 | Kaster et al. |
| 5,267,940 | A | 12/1993 | Moulder |
| 5,290,227 | A | 3/1994 | Pasque |
| 5,312,341 | A | 5/1994 | Turi |
| 5,326,374 | A | 7/1994 | Ilbawi et al. |
| 5,332,402 | A | 7/1994 | Teitelbaum |
| 5,334,217 | A | 8/1994 | Das |
| 5,378,239 | A | 1/1995 | Termin et al. |
| 5,409,019 | A | 4/1995 | Wilk |
| 5,429,144 | A | 7/1995 | Wilk |
| 5,479,945 | A | 1/1996 | Simon |
| 5,500,015 | A | 3/1996 | Deac |
| 5,531,759 | A | 7/1996 | Kensey et al. |
| 5,545,210 | A | 8/1996 | Hess et al. |
| 5,556,386 | A | 9/1996 | Todd |
| 5,562,641 | A | 10/1996 | Flomenblit et al. |
| 5,578,008 | A | 11/1996 | Hara |
| 5,584,803 | A | 12/1996 | Stevens et al. |
| 5,597,377 | A | 1/1997 | Aldea |
| 5,645,559 | A | 7/1997 | Hachtman et al. |
| 5,655,548 | A | 8/1997 | Nelson et al. |
| 5,662,711 | A | 9/1997 | Douglas |
| 5,702,412 | A | 12/1997 | Popov et al. |
| 5,725,552 | A | 3/1998 | Kotula et al. |
| 5,741,324 | A | 4/1998 | Glastra |
| 5,749,880 | A | 5/1998 | Banas et al. |
| 5,779,716 | A | 7/1998 | Cano et al. |
| 5,795,307 | A | 8/1998 | Krueger |
| 5,810,836 | A | 9/1998 | Hussein et al. |
| 5,824,062 | A | 10/1998 | Patke et al. |
| 5,824,071 | A | 10/1998 | Nelson et al. |
| 5,846,261 | A | 12/1998 | Kotula et al. |
| 5,876,434 | A | 3/1999 | Flomenblit et al. |
| 5,910,144 | A | 6/1999 | Hayashi |
| 5,916,193 | A | 6/1999 | Stevens et al. |
| 5,938,695 | A | 8/1999 | Borghi |
| 5,941,850 | A | 8/1999 | Shah et al. |
| 5,951,583 | A | 9/1999 | Jensen et al. |
| 5,957,949 | A | 9/1999 | Leonhardt et al. |
| 5,990,379 | A | 11/1999 | Gregory |
| 6,007,544 | A | 12/1999 | Kim |
| 6,010,529 | A | 1/2000 | Herweck et al. |
| 6,027,518 | A | 2/2000 | Gaber |
| 6,039,755 | A | 3/2000 | Edwin et al. |
| 6,039,759 | A | 3/2000 | Carpentier et al. |
| 6,059,810 | A | 5/2000 | Brown et al. |
| 6,086,610 | A | 7/2000 | Duerig et al. |
| 6,111,520 | A | 8/2000 | Allen et al. |
| 6,117,159 | A | 9/2000 | Huebsch et al. |
| 6,120,534 | A | 9/2000 | Ruiz |
| 6,124,523 | A | 9/2000 | Banas et al. |
| 6,126,686 | A | 10/2000 | Badylak et al. |
| 6,165,188 | A | 12/2000 | Saadat et al. |
| 6,210,318 | B1 | 4/2001 | Lederman |
| 6,214,029 | B1 * | 4/2001 | Thill .................. A61B 17/0057 |
|  |  |  | 606/213 |
| 6,214,039 | B1 | 4/2001 | Banas et al. |
| 6,216,029 | B1 * | 4/2001 | Paltieli ................... A61B 34/20 |
|  |  |  | 600/461 |
| 6,217,541 | B1 | 4/2001 | Yu |
| 6,221,096 | B1 | 4/2001 | Aiba et al. |
| 6,231,587 | B1 | 5/2001 | Makower |
| 6,242,762 | B1 | 6/2001 | Brown et al. |
| 6,245,099 | B1 | 6/2001 | Edwin et al. |
| 6,254,564 | B1 | 7/2001 | Wilk et al. |
| 6,260,552 | B1 | 7/2001 | Mortier et al. |
| 6,264,684 | B1 | 7/2001 | Banas et al. |
| 6,270,515 | B1 | 8/2001 | Linden et al. |
| 6,270,526 | B1 | 8/2001 | Cox |
| 6,277,078 | B1 | 8/2001 | Porat et al. |
| 6,278,379 | B1 | 8/2001 | Allen et al. |
| 6,290,728 | B1 | 9/2001 | Phelps et al. |
| 6,302,892 | B1 | 10/2001 | Wilk |
| 6,306,141 | B1 | 10/2001 | Jervis |
| 6,328,699 | B1 | 12/2001 | Eigler et al. |
| 6,344,022 | B1 | 2/2002 | Jarvik |
| 6,358,277 | B1 | 3/2002 | Duran |
| 6,391,036 | B1 | 5/2002 | Berg et al. |
| 6,398,803 | B1 | 6/2002 | Layne et al. |
| 6,406,422 | B1 | 6/2002 | Landesberg |
| 6,447,539 | B1 | 9/2002 | Nelson et al. |
| 6,451,051 | B2 | 9/2002 | Drasler et al. |
| 6,458,153 | B1 | 10/2002 | Bailey et al. |
| 6,468,303 | B1 | 10/2002 | Amplatz et al. |
| 6,475,136 | B1 | 11/2002 | Forsell |
| 6,478,776 | B1 | 11/2002 | Rosenman et al. |
| 6,485,507 | B1 | 11/2002 | Walak et al. |
| 6,488,702 | B1 | 12/2002 | Besselink |
| 6,491,705 | B2 | 12/2002 | Gifford, III et al. |
| 6,497,722 | B1 | 12/2002 | Von Oepen et al. |
| 6,527,698 | B1 | 3/2003 | Kung et al. |
| 6,544,208 | B2 | 4/2003 | Ethier et al. |
| 6,547,814 | B2 | 4/2003 | Edwin et al. |
| 6,562,066 | B1 | 5/2003 | Martin |
| 6,572,652 | B2 | 6/2003 | Shaknovich |
| 6,579,314 | B1 | 6/2003 | Lombardi et al. |
| 6,589,198 | B1 | 7/2003 | Soltanpour et al. |
| 6,616,675 | B1 | 9/2003 | Evard et al. |
| 6,632,169 | B2 | 10/2003 | Korakianitis et al. |
| 6,638,303 | B1 | 10/2003 | Campbell |
| 6,641,610 | B2 | 11/2003 | Wolf et al. |
| 6,645,220 | B1 | 11/2003 | Huter et al. |
| 6,652,578 | B2 | 11/2003 | Bailey et al. |
| 6,685,664 | B2 | 2/2004 | Levin et al. |
| 6,712,836 | B1 | 3/2004 | Berg et al. |
| 6,719,781 | B1 | 4/2004 | Kim |
| 6,740,115 | B2 | 5/2004 | Lombardi et al. |
| 6,758,858 | B2 | 7/2004 | McCrea et al. |
| 6,764,507 | B2 | 7/2004 | Shanley et al. |
| 6,770,087 | B2 | 8/2004 | Layne et al. |
| 6,797,217 | B2 | 9/2004 | McCrea et al. |
| 6,805,711 | B2 | 10/2004 | Quijano et al. |
| 6,890,350 | B1 | 5/2005 | Walak |
| 6,923,829 | B2 | 8/2005 | Boyle et al. |
| 6,964,680 | B2 | 11/2005 | Shanley |
| 6,970,742 | B2 | 11/2005 | Mann et al. |
| 7,001,409 | B2 | 2/2006 | Amplatz |
| 7,004,966 | B2 | 2/2006 | Edwin et al. |
| 7,025,777 | B2 | 4/2006 | Moore |
| 7,060,150 | B2 | 6/2006 | Banas et al. |
| 7,083,640 | B2 | 8/2006 | Lombardi et al. |
| 7,115,095 | B2 | 10/2006 | Eigler et al. |
| 7,118,600 | B2 | 10/2006 | Dua et al. |
| 7,128,758 | B2 | 10/2006 | Cox |
| 7,137,953 | B2 | 11/2006 | Eigler et al. |
| 7,147,604 | B1 | 12/2006 | Allen et al. |
| 7,149,587 | B2 | 12/2006 | Wardle et al. |
| 7,169,160 | B1 | 1/2007 | Middleman et al. |
| 7,169,172 | B2 | 1/2007 | Levine et al. |
| 7,195,594 | B2 | 3/2007 | Eigler et al. |
| 7,208,010 | B2 | 4/2007 | Shanley et al. |
| 7,226,558 | B2 | 6/2007 | Nieman et al. |
| 7,245,117 | B1 | 7/2007 | Joy et al. |

(56)  References Cited

U.S. PATENT DOCUMENTS

| | | | |
|---|---|---|---|
| 7,294,115 B1 | 11/2007 | Wilk |
| 7,306,756 B2 | 12/2007 | Edwin et al. |
| 7,383,071 B1 | 6/2008 | Russell et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,575,586 B2 | 8/2009 | Berg et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,632,303 B1 | 12/2009 | Stalker et al. |
| 7,679,355 B2 | 3/2010 | Allen et al. |
| 7,717,854 B2 | 5/2010 | Mann et al. |
| 7,789,975 B2 | 9/2010 | Cheung et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,221,491 B1 | 7/2012 | Burmeister et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,660,667 B1 | 2/2014 | Kusumoto |
| 8,665,086 B2 | 3/2014 | Miller et al. |
| 8,696,611 B2 | 4/2014 | Nitzan et al. |
| 8,715,314 B1 | 5/2014 | Janardhan et al. |
| 8,790,241 B2 | 7/2014 | Edwin et al. |
| 8,808,294 B2 | 8/2014 | Fox et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 8,992,567 B1 | 3/2015 | Houser |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 * | 6/2015 | Gallagher ......... A61M 5/16813 |
| 9,205,236 B2 | 12/2015 | McNamara et al. |
| 9,220,429 B2 | 12/2015 | Nabutovsky et al. |
| 9,232,997 B2 | 1/2016 | Sugimoto et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,136,897 B2 | 11/2018 | Watson et al. |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,265,169 B2 | 4/2019 | Desrosiers et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,542,994 B2 | 1/2020 | Ben-Muvhar et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,744,012 B2 | 8/2020 | Bonsignore et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,045,338 B2 | 6/2021 | Boyle et al. |
| 11,109,988 B2 | 9/2021 | Rosen et al. |
| 11,135,054 B2 * | 10/2021 | Nitzan ............... A61B 17/0057 |
| 11,234,702 B1 | 2/2022 | Eigler et al. |
| 11,253,353 B2 | 2/2022 | Levi et al. |
| 11,255,379 B2 | 2/2022 | Baskin et al. |
| 11,266,501 B2 | 3/2022 | Rottenberg et al. |
| 11,291,807 B2 | 4/2022 | Eigler et al. |
| 11,304,831 B2 | 4/2022 | Nae et al. |
| 11,311,375 B2 | 4/2022 | Li |
| 11,382,747 B2 | 7/2022 | Rottenberg et al. |
| 11,458,287 B2 | 10/2022 | Eigler et al. |
| 11,497,631 B2 | 11/2022 | Rosen et al. |
| 11,607,327 B2 | 3/2023 | Nae et al. |
| 11,612,385 B2 | 3/2023 | Nae et al. |
| 11,690,976 B2 | 7/2023 | Yacoby et al. |
| 11,744,589 B2 | 9/2023 | Ben-David et al. |
| 11,813,386 B2 * | 11/2023 | Nae .......................... A61B 17/11 |
| 11,850,138 B2 | 12/2023 | Eigler et al. |
| 11,865,282 B2 | 1/2024 | Nae et al. |
| 12,005,214 B2 | 6/2024 | Nitzan et al. |
| 12,115,328 B2 | 10/2024 | Nae et al. |
| 12,186,176 B2 | 1/2025 | Eigler et al. |

(56)                 References Cited

U.S. PATENT DOCUMENTS

| | | | |
|---|---|---|---|
| 12,186,510 | B2 | 1/2025 | Keren |
| 12,226,602 | B2 | 2/2025 | Nae et al. |
| 12,251,529 | B2 | 3/2025 | Nae et al. |
| 12,296,122 | B2 | 5/2025 | Nae et al. |
| 12,303,390 | B2 | 5/2025 | Rottenberg et al. |
| 12,311,134 | B2 | 5/2025 | Eigler et al. |
| 12,349,912 | B2 | 7/2025 | Ben-David et al. |
| 12,369,918 | B2 | 7/2025 | Eigler et al. |
| 12,453,626 | B2 | 10/2025 | Eigler et al. |
| 12,465,485 | B2 | 11/2025 | Nitzan et al. |
| 12,465,488 | B2 | 11/2025 | Rottenberg et al. |
| 12,502,272 | B2 | 12/2025 | Nitzan et al. |
| 2001/0007956 | A1 | 7/2001 | Letac et al. |
| 2001/0020154 | A1 | 9/2001 | Bigus et al. |
| 2001/0021872 | A1 | 9/2001 | Bailey et al. |
| 2002/0042565 | A1 | 4/2002 | Cooper et al. |
| 2002/0051730 | A1 | 5/2002 | Bodnar et al. |
| 2002/0099431 | A1 | 7/2002 | Armstrong et al. |
| 2002/0120277 | A1 | 8/2002 | Hauschild et al. |
| 2002/0165479 | A1 | 11/2002 | Wilk |
| 2002/0165606 | A1 | 11/2002 | Wolf et al. |
| 2002/0169371 | A1 | 11/2002 | Gilderdale |
| 2002/0169377 | A1 | 11/2002 | Khairkhahan et al. |
| 2002/0173742 | A1 | 11/2002 | Keren et al. |
| 2002/0183628 | A1 | 12/2002 | Reich et al. |
| 2003/0028213 | A1 | 2/2003 | Thill et al. |
| 2003/0029457 | A1 | 2/2003 | Callister et al. |
| 2003/0045902 | A1 | 3/2003 | Weadock |
| 2003/0097172 | A1 | 5/2003 | Shalev et al. |
| 2003/0100920 | A1 | 5/2003 | Akin et al. |
| 2003/0125798 | A1 | 7/2003 | Martin |
| 2003/0136417 | A1 | 7/2003 | Fonseca et al. |
| 2003/0139819 | A1 | 7/2003 | Beer et al. |
| 2003/0176914 | A1 | 9/2003 | Rabkin et al. |
| 2003/0208263 | A1 | 11/2003 | Burmeister et al. |
| 2003/0209835 | A1 | 11/2003 | Chun et al. |
| 2003/0216679 | A1 | 11/2003 | Wolf et al. |
| 2003/0216803 | A1 | 11/2003 | Ledergerber |
| 2004/0010219 | A1 | 1/2004 | McCusker et al. |
| 2004/0016514 | A1 | 1/2004 | Nien |
| 2004/0073242 | A1 | 4/2004 | Chanduszko |
| 2004/0077988 | A1 | 4/2004 | Tweden et al. |
| 2004/0087984 | A1 | 5/2004 | Kupiecki et al. |
| 2004/0088045 | A1 | 5/2004 | Cox |
| 2004/0093075 | A1 | 5/2004 | Kuehne |
| 2004/0102797 | A1 | 5/2004 | Golden et al. |
| 2004/0116999 | A1 | 6/2004 | Ledergerber |
| 2004/0138743 | A1 | 7/2004 | Myers et al. |
| 2004/0147869 | A1 | 7/2004 | Wolf et al. |
| 2004/0147871 | A1 | 7/2004 | Burnett |
| 2004/0147886 | A1 | 7/2004 | Bonni |
| 2004/0147969 | A1 | 7/2004 | Mann et al. |
| 2004/0162514 | A1 | 8/2004 | Alferness et al. |
| 2004/0193261 | A1 | 9/2004 | Berreklouw |
| 2004/0210190 | A1 | 10/2004 | Kohler et al. |
| 2004/0210307 | A1 | 10/2004 | Khairkhahan |
| 2004/0225352 | A1 | 11/2004 | Osborne et al. |
| 2004/0249335 | A1 | 12/2004 | Faul et al. |
| 2005/0003327 | A1 | 1/2005 | Elian et al. |
| 2005/0033327 | A1 | 2/2005 | Gainor et al. |
| 2005/0033351 | A1 | 2/2005 | Newton |
| 2005/0065589 | A1 | 3/2005 | Schneider et al. |
| 2005/0125032 | A1 | 6/2005 | Whisenant et al. |
| 2005/0137682 | A1 | 6/2005 | Justino |
| 2005/0148925 | A1* | 7/2005 | Rottenberg ...... A61B 17/00234<br>604/9 |
| 2005/0149097 | A1 | 7/2005 | Regnell et al. |
| 2005/0149166 | A1 | 7/2005 | Schaeffer et al. |
| 2005/0165344 | A1* | 7/2005 | Dobak .................. A61F 2/2476<br>604/8 |
| 2005/0182486 | A1 | 8/2005 | Gabbay |
| 2005/0228480 | A1 | 10/2005 | Douglas et al. |
| 2005/0267524 | A1* | 12/2005 | Chanduszko ...... A61B 17/0057<br>606/213 |
| 2005/0283231 | A1 | 12/2005 | Haug et al. |
| 2005/0288596 | A1 | 12/2005 | Eigler et al. |
| 2005/0288706 | A1 | 12/2005 | Widomski et al. |
| 2005/0288786 | A1 | 12/2005 | Chanduszko |
| 2006/0009800 | A1 | 1/2006 | Christianson et al. |
| 2006/0015002 | A1 | 1/2006 | Moaddeb et al. |
| 2006/0015178 | A1 | 1/2006 | Moaddeb et al. |
| 2006/0025857 | A1 | 2/2006 | Bergheim et al. |
| 2006/0052821 | A1 | 3/2006 | Abbott et al. |
| 2006/0064055 | A1 | 3/2006 | Pile-Spellman et al. |
| 2006/0106449 | A1 | 5/2006 | Ben Muvhar |
| 2006/0111660 | A1 | 5/2006 | Wolf et al. |
| 2006/0111704 | A1 | 5/2006 | Brenneman et al. |
| 2006/0116710 | A1 | 6/2006 | Corcoran et al. |
| 2006/0122522 | A1 | 6/2006 | Chavan et al. |
| 2006/0122647 | A1 | 6/2006 | Callaghan et al. |
| 2006/0167541 | A1 | 7/2006 | Lattouf |
| 2006/0184231 | A1 | 8/2006 | Rucker |
| 2006/0212110 | A1 | 9/2006 | Osborne et al. |
| 2006/0241745 | A1 | 10/2006 | Solem |
| 2006/0256611 | A1 | 11/2006 | Bednorz et al. |
| 2006/0282157 | A1 | 12/2006 | Hill et al. |
| 2007/0010852 | A1 | 1/2007 | Blaeser et al. |
| 2007/0021739 | A1 | 1/2007 | Weber |
| 2007/0043391 | A1 | 2/2007 | Moszner et al. |
| 2007/0043435 | A1 | 2/2007 | Seguin et al. |
| 2007/0073337 | A1 | 3/2007 | Abbott et al. |
| 2007/0093048 | A1 | 4/2007 | Shim |
| 2007/0118207 | A1 | 5/2007 | Amplatz et al. |
| 2007/0129756 | A1 | 6/2007 | Abbott et al. |
| 2007/0129784 | A1 | 6/2007 | Lendlein et al. |
| 2007/0191863 | A1 | 8/2007 | De Juan, Jr. et al. |
| 2007/0193632 | A1 | 8/2007 | Shu |
| 2007/0213813 | A1 | 9/2007 | Von Segesser et al. |
| 2007/0249985 | A1 | 10/2007 | Brenneman et al. |
| 2007/0276413 | A1 | 11/2007 | Nobles |
| 2007/0276414 | A1 | 11/2007 | Nobles |
| 2007/0282157 | A1 | 12/2007 | Rottenberg et al. |
| 2007/0293939 | A1 | 12/2007 | Shrivastava et al. |
| 2007/0299384 | A1 | 12/2007 | Faul et al. |
| 2008/0034836 | A1 | 2/2008 | Eigler et al. |
| 2008/0051829 | A1 | 2/2008 | Eidenschink et al. |
| 2008/0086205 | A1 | 4/2008 | Gordy et al. |
| 2008/0125861 | A1 | 5/2008 | Webler et al. |
| 2008/0171944 | A1 | 7/2008 | Brenneman et al. |
| 2008/0177300 | A1 | 7/2008 | Mas et al. |
| 2008/0221609 | A1 | 9/2008 | McGuckin et al. |
| 2008/0243081 | A1 | 10/2008 | Nance et al. |
| 2008/0262602 | A1 | 10/2008 | Wilk et al. |
| 2008/0264102 | A1 | 10/2008 | Berra |
| 2008/0274011 | A1 | 11/2008 | Flomenblit et al. |
| 2008/0319525 | A1 | 12/2008 | Tieu et al. |
| 2009/0030499 | A1 | 1/2009 | Bebb et al. |
| 2009/0054976 | A1 | 2/2009 | Tuval et al. |
| 2009/0125104 | A1 | 5/2009 | Hoffman |
| 2009/0149947 | A1 | 6/2009 | Frohwitter |
| 2009/0198315 | A1 | 8/2009 | Boudjemline |
| 2009/0248133 | A1 | 10/2009 | Bloom et al. |
| 2009/0264859 | A1 | 10/2009 | Mas |
| 2009/0276040 | A1 | 11/2009 | Rowe et al. |
| 2009/0319037 | A1 | 12/2009 | Rowe et al. |
| 2010/0004740 | A1 | 1/2010 | Seguin et al. |
| 2010/0022940 | A1 | 1/2010 | Thompson |
| 2010/0023046 | A1 | 1/2010 | Heidner et al. |
| 2010/0023047 | A1 | 1/2010 | Simpson |
| 2010/0057192 | A1 | 3/2010 | Celermajer |
| 2010/0069836 | A1 | 3/2010 | Satake |
| 2010/0070022 | A1 | 3/2010 | Kuehling |
| 2010/0081867 | A1 | 4/2010 | Fishler et al. |
| 2010/0100167 | A1 | 4/2010 | Bortlein et al. |
| 2010/0121434 | A1 | 5/2010 | Paul et al. |
| 2010/0125288 | A1 | 5/2010 | Gelfand et al. |
| 2010/0179590 | A1 | 7/2010 | Fortson et al. |
| 2010/0191326 | A1 | 7/2010 | Alkhatib |
| 2010/0249490 | A1 | 9/2010 | Farnan |
| 2010/0249491 | A1 | 9/2010 | Farnan et al. |
| 2010/0249909 | A1 | 9/2010 | McNamara et al. |
| 2010/0249910 | A1 | 9/2010 | McNamara et al. |
| 2010/0249915 | A1 | 9/2010 | Zhang |
| 2010/0256548 | A1 | 10/2010 | McNamara et al. |

(56)  References Cited

U.S. PATENT DOCUMENTS

| | | |
|---|---|---|
| 2010/0256753 A1 | 10/2010 | McNamara et al. |
| 2010/0298632 A1 | 11/2010 | Levine et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0106149 A1 | 5/2011 | Ryan et al. |
| 2011/0112632 A1 | 5/2011 | Chau et al. |
| 2011/0137398 A1 | 6/2011 | Magnuson et al. |
| 2011/0152923 A1 | 6/2011 | Fox |
| 2011/0152994 A1 | 6/2011 | Hendriksen et al. |
| 2011/0190874 A1 | 8/2011 | Celermajer et al. |
| 2011/0213449 A1 | 9/2011 | Ginn et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0218613 A1 | 9/2011 | Leopold et al. |
| 2011/0251675 A1 | 10/2011 | Dwork |
| 2011/0257723 A1 | 10/2011 | McNamara |
| 2011/0264191 A1 | 10/2011 | Rothstein |
| 2011/0264203 A1 | 10/2011 | Dwork et al. |
| 2011/0265908 A1 | 11/2011 | Clerc et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1* | 12/2011 | Nitzan ................ A61M 27/006 604/9 |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0109056 A1 | 5/2012 | Rasmussen |
| 2012/0130301 A1 | 5/2012 | McNamara et al. |
| 2012/0165928 A1 | 6/2012 | Nitzan et al. |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271277 A1 | 10/2012 | Fischell et al. |
| 2012/0271398 A1 | 10/2012 | Essinger et al. |
| 2012/0289815 A1 | 11/2012 | Keast et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0144373 A1 | 6/2013 | Shahriari |
| 2013/0166021 A1 | 6/2013 | Bruchman et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0253342 A1 | 9/2013 | Griswold et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0039599 A1 | 2/2014 | Berreklouw |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2014/0358222 A1 | 12/2014 | Gorman, III et al. |
| 2014/0364941 A1 | 12/2014 | Edmiston et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0294313 A1 | 10/2015 | Kamal et al. |
| 2015/0297346 A1 | 10/2015 | Duffy et al. |
| 2015/0313599 A1 | 11/2015 | Johnson et al. |
| 2015/0335801 A1 | 11/2015 | Farnan et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0045165 A1 | 2/2016 | Braido et al. |
| 2016/0045311 A1 | 2/2016 | McCann et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0151056 A1 | 6/2016 | Lederman et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0028176 A1 | 2/2017 | Dam et al. |
| 2017/0035435 A1 | 2/2017 | Amin et al. |

(56) References Cited

U.S. PATENT DOCUMENTS

| | | |
|---|---|---|
| 2017/0056171 A1 | 3/2017 | Cooper et al. |
| 2017/0072173 A1 | 3/2017 | Van Dam et al. |
| 2017/0106176 A1 | 4/2017 | Taft et al. |
| 2017/0112624 A1 | 4/2017 | Patel |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165062 A1 | 6/2017 | Rothstein |
| 2017/0165532 A1 | 6/2017 | Khan et al. |
| 2017/0196509 A1 | 7/2017 | Hunter |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0028314 A1 | 2/2018 | Ekvall et al. |
| 2018/0085128 A1 | 3/2018 | Bellomo et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0116843 A1 | 5/2018 | Schreck et al. |
| 2018/0125630 A1 | 5/2018 | Hynes et al. |
| 2018/0130988 A1 | 5/2018 | Nishikawa et al. |
| 2018/0153691 A1 | 6/2018 | Anderson et al. |
| 2018/0200496 A1 | 7/2018 | Kratzberg et al. |
| 2018/0235791 A1 | 8/2018 | Kang et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0280668 A1 | 10/2018 | Alaswad |
| 2018/0344994 A1 | 12/2018 | Karavany et al. |
| 2018/0360632 A1 | 12/2018 | Kim |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0076275 A1 | 3/2019 | Kim |
| 2019/0076583 A1 | 3/2019 | Kim |
| 2019/0083076 A1 | 3/2019 | Alanbaei |
| 2019/0091047 A1 | 3/2019 | Walsh |
| 2019/0091438 A1 | 3/2019 | Higgins et al. |
| 2019/0110911 A1 | 4/2019 | Nae et al. |
| 2019/0151122 A1 | 5/2019 | Kim |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0138612 A1 | 5/2020 | Higashi et al. |
| 2020/0188091 A1 | 6/2020 | Lane et al. |
| 2020/0197178 A1 | 6/2020 | Vecchio |
| 2020/0238059 A1 | 7/2020 | Wang et al. |
| 2020/0261224 A1 | 8/2020 | Gross |
| 2020/0261705 A1 | 8/2020 | Nitzan et al. |
| 2020/0268537 A1 | 8/2020 | Reisin et al. |
| 2020/0281611 A1 | 9/2020 | Kelly et al. |
| 2020/0315599 A1 | 10/2020 | Nae et al. |
| 2020/0368505 A1 | 11/2020 | Nae et al. |
| 2021/0022507 A1 | 1/2021 | Williams |
| 2021/0052378 A1 | 2/2021 | Nitzan et al. |
| 2021/0100665 A1* | 4/2021 | Nae ..................... A61F 2/844 |
| 2021/0121179 A1 | 4/2021 | Ben-David et al. |
| 2021/0161637 A1 | 6/2021 | Eigler et al. |
| 2021/0205590 A1 | 7/2021 | Fahey et al. |
| 2021/0338990 A1 | 11/2021 | Eigler et al. |
| 2021/0393421 A1 | 12/2021 | Rosen et al. |
| 2022/0008014 A1 | 1/2022 | Rowe et al. |
| 2022/0015901 A1 | 1/2022 | Dibie |
| 2022/0054266 A1 | 2/2022 | Kovalsky et al. |
| 2022/0125571 A1 | 4/2022 | El Azouzi et al. |
| 2022/0133463 A1 | 5/2022 | Korte |
| 2022/0151784 A1 | 5/2022 | Eigler et al. |
| 2022/0211361 A1 | 7/2022 | Rolando et al. |
| 2022/0211985 A1 | 7/2022 | Eigler et al. |
| 2022/0241565 A1 | 8/2022 | Nae et al. |
| 2022/0290275 A1 | 9/2022 | Born et al. |
| 2022/0304803 A1 | 9/2022 | Guyenot et al. |
| 2022/0313426 A1 | 10/2022 | Gifford, III et al. |
| 2022/0346935 A1 | 11/2022 | Shermer et al. |
| 2024/0139478 A1 | 5/2024 | Robertson et al. |
| 2024/0252791 A1 | 8/2024 | Ortiz Garcia et al. |
| 2025/0262418 A1 | 8/2025 | Nae et al. |
| 2025/0281726 A1 | 9/2025 | Eigler et al. |
| 2025/0331858 A1 | 10/2025 | Ben-David et al. |
| 2025/0352210 A1 | 11/2025 | Eigler et al. |

FOREIGN PATENT DOCUMENTS

| | | |
|---|---|---|
| CN | 101505680 A | 8/2009 |
| CN | 105555204 A | 5/2016 |
| CN | 108451569 A | 8/2018 |
| CN | 113397762 A | 9/2021 |
| DE | 10142998 B4 | 2/2005 |
| DE | 102015122113 A1 | 6/2017 |
| EP | 1808135 A1 | 7/2007 |
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 2702965 A1 | 3/2014 |
| EP | 3400907 A1 | 11/2018 |
| EP | 4458323 A1 | 11/2024 |
| FR | 2827153 A1 | 1/2003 |
| GB | 2468861 A | 9/2010 |
| JP | 2020509812 A | 4/2020 |
| WO | WO-9531945 A1 | 11/1995 |
| WO | WO-9702850 A1 | 1/1997 |
| WO | WO-9727898 A1 | 8/1997 |
| WO | WO-9960941 A1 | 12/1999 |
| WO | WO-0044311 A2 | 8/2000 |
| WO | WO-0050100 A1 | 8/2000 |
| WO | WO-0110314 A2 | 2/2001 |
| WO | WO-0126585 A1 | 4/2001 |
| WO | WO-0191828 A2 | 12/2001 |
| WO | WO-0226281 A1 | 4/2002 |
| WO | WO-02071974 A2 | 9/2002 |
| WO | WO-02087473 A1 | 11/2002 |
| WO | WO-03050320 A1 | 6/2003 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2008070797 A2 | 6/2008 |
| WO | WO-2009029261 A1 | 3/2009 |
| WO | WO-2010128501 A1 | 11/2010 |
| WO | WO-2010129089 A2 | 11/2010 |
| WO | WO-2010139771 A2 | 12/2010 |
| WO | WO-2010139771 A3 | 1/2011 |
| WO | WO-2011062858 A1 | 5/2011 |
| WO | WO-2011062970 A1 | 5/2011 |
| WO | WO-2013028837 A1 | 2/2013 |
| WO | WO-2013096965 A1 | 6/2013 |
| WO | WO-2013172474 A1 | 11/2013 |
| WO | WO-2016178171 A1 | 11/2016 |
| WO | WO-2017031235 A1 | 2/2017 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |

(56) References Cited

FOREIGN PATENT DOCUMENTS

| WO | WO-2019142152 A1 | 7/2019 |
|---|---|---|
| WO | WO-2019179447 A1 | 9/2019 |
| WO | WO-2019212812 A1 | 11/2019 |
| WO | WO-2019218072 A1 | 11/2019 |
| WO | WO-2020123338 A1 | 6/2020 |
| WO | WO-2020163112 A1 | 8/2020 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |
| WO | WO-2021224736 A1 | 11/2021 |
| WO | WO-2022046921 A1 | 3/2022 |
| WO | WO-2022076601 A1 | 4/2022 |
| WO | WO-2022091018 A1 | 5/2022 |
| WO | WO-2022091019 A1 | 5/2022 |
| WO | WO-2022103973 A1 | 5/2022 |
| WO | WO-2023079498 A1 | 5/2023 |
| WO | WO-2024088350 A1 | 5/2024 |
| WO | WO-2024249425 A1 | 12/2024 |
| WO | WO-2025021050 A1 | 1/2025 |
| WO | WO-2025021068 A1 | 1/2025 |
| WO | WO-2025039936 A1 | 2/2025 |
| WO | WO-2025039940 A1 | 2/2025 |

OTHER PUBLICATIONS

U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Jul. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.
U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752 / U.S. Pat. No. 10,940,296, filed Oct. 31, 2017 / Mar. 9, 2021.
U.S. Appl. No. 15/608,948, filed May 30, 2017.
U.S. Appl. No. 15/624,314 / U.S. Pat. No. 10,357,357, filed Jun. 15, 2017 / Jul. 23, 2019.
U.S. Appl. No. 15/650,783 / U.S. Pat. No. 10,639,459, filed Jul. 14, 2017 / May 5, 2020.
U.S. Appl. No. 15/656,936 / U.S. Pat. No. 10,478,594, filed Jul. 21, 2017 / Nov. 19, 2019.

U.S. Appl. No. 15/668,622 / U.S. Pat. No. 10,463,490, filed Aug. 3, 2017 / Nov. 5, 2019.
U.S. Appl. No. 15/798,250 / U.S. Pat. No. 11,109,988, filed Oct. 30, 2017 / Sep. 7, 2021.
U.S. Appl. No. 15/988,888 / U.S. Pat. No. 10,828,151, filed May 24, 2018 / Nov. 10, 2020.
U.S. Appl. No. 16/130,978 / U.S. Pat. No. 10,251,740, filed Sep. 13, 2018 / Apr. 9, 2019.
U.S. Appl. No. 16/130,988 / U.S. Pat. No. 10,925,706, filed Sep. 13, 2018 / Feb. 23, 2021.
U.S. Appl. No. 16/205,213 / U.S. Pat. No. 10,835,394, filed Nov. 29, 2018 / Nov. 17, 2020.
U.S. Appl. No. 16/374,698 / U.S. Pat. No. 11,612,385, filed Apr. 3, 2019 / Mar. 28, 2023.
U.S. Appl. No. 16/395,209 / U.S. Pat. No. 11,135,054, filed Apr. 25, 2019 / Oct. 5, 2021.
U.S. Appl. No. 16/408,419 / U.S. Pat. No. 11,291,807, filed May 9, 2019 / Apr. 5, 2022.
U.S. Appl. No. 16/505,624 / U.S. Pat. No. 11,253,353, filed Jul. 8, 2019 / Feb. 22, 2022.
U.S. Appl. No. 16/672,420 / U.S. Pat. No. 11,266,501, filed Nov. 1, 2019 / Mar. 8, 2022.
U.S. Appl. No. 16/686,013 / U.S. Pat. No. 11,690,976, filed Nov. 15, 2019 / Jul. 4, 2023.
U.S. Appl. No. 16/866,377, filed May 4, 2020.
U.S. Appl. No. 16/875,652 / U.S. Pat. No. 10,898,698, filed May 15, 2020 / Jan. 26, 2021.
U.S. Appl. No. 16/876,640, filed May 18, 2020.
U.S. Appl. No. 16/878,228 / U.S. Pat. No. 10,912,645, filed May 19, 2020 / Feb. 9, 2021.
U.S. Appl. No. 16/963,139 / U.S. Pat. No. 11,744,589, filed Jul. 17, 2020 / Sep. 5, 2023.
U.S. Appl. No. 17/092,063, filed Nov. 6, 2020.
U.S. Appl. No. 17/092,081, filed Nov. 6, 2020.
U.S. Appl. No. 17/095,615 / U.S. Pat. No. 11,304,831, filed Nov. 11, 2020 / Apr. 19, 2022.
U.S. Appl. No. 17/098,251 / U.S. Pat. No. 11,234,702, filed Nov. 13, 2020 / Feb. 1, 2022.
U.S. Appl. No. 17/166,771, filed Feb. 3, 2021.
U.S. Appl. No. 17/175,549, filed Feb. 12, 2021.
U.S. Appl. No. 17/192,612, filed Mar. 4, 2021.
U.S. Appl. No. 17/465,791 / U.S. Pat. No. 11,497,631, filed Sep. 2, 2021 / Nov. 15, 2022.
U.S. Appl. No. 17/490,510, filed Sep. 30, 2021.
U.S. Appl. No. 17/600,079, filed Sep. 29, 2021.
U.S. Appl. No. 17/649,176, filed Jan. 27, 2022.
U.S. Appl. No. 17/649,331, filed Jan. 28, 2022.
U.S. Appl. No. 17/651,409, filed Feb. 16, 2022.
U.S. Appl. No. 17/653,551 / U.S. Pat. No. 11,382,747, filed Mar. 4, 2022 / Jul. 12, 2022.
U.S. Appl. No. 17/656,521, filed Mar. 25, 2022.
U.S. Appl. No. 17/659,312 / U.S. Pat. No. 11,607,327, filed Apr. 14, 2022 / Mar. 21, 2023.
U.S. Appl. No. 17/660,384 / U.S. Pat. No. 11,458,287, filed Apr. 22, 2022 / Oct. 4, 2022.
U.S. Appl. No. 17/805,001, filed Jun. 1, 2022.
U.S. Appl. No. 17/811,476, filed Jul. 8, 2022.
U.S. Appl. No. 17/823,047, filed Aug. 29, 2022.
U.S. Appl. No. 17/997,902, filed Nov. 3, 2022.
U.S. Appl. No. 18/180,068, filed Mar. 7, 2023.
U.S. Appl. No. 18/320,108, filed May 18, 2023.
U.S. Appl. No. 18/458,642, filed Aug. 30, 2023.
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).

(56)                    References Cited

OTHER PUBLICATIONS

Abreu et al., "Doppler ultrasonography of the femoropopliteal segment in patients with venous ulcer," J Vasc Bras., 11(4):277-285 (2012).

Adamson et al., "Ongoing Right Ventricular Hemodynamics in Heart Failure Clinical Value of Measurements Derived From an Implantable Monitoring System," J Am Coll Cardiol., 41(4):565-571 (2003).

Adamson et al., "Wireless Pulmonary Artery Pressure Monitoring Guides Management to Reduce Decompensation in Heart Failure With Preserved Ejection Fraction," Circ Heart Fail., 7:935-944 (2014).

Ambrosy et al. "The Global Health and Economic Burden of Hospitalizations for Heart Failure," J Am Coll Cardiol., 63:1123-1133 (2014).

Aminde et al., "Current diagnostic and treatment strategies for Lutembacher syndrome: the pivotal role of echocardiography," Cardiovasc Diagn Ther., 5(2):122-132 (2015).

Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).

Anderas et al., "Tilted c-axis Thin-Film Bulk Wave Resonant Pressure Sensors with Improved Sensitivity," IEEE Sensors J., 12(8):2653-2654 (2012).

Ando, et al., Left ventricular decompression through a patent foramen ovale in a patient with hypertrophic cardiomyopathy: A case report, Cardiovascular Ultrasound, 2: 1-7 (2004).

Article 34 Amendments dated May 28, 2013 in Int'l PCT Patent Appl. Serial No. PCT/IB2012/001859 (0810).

Article 34 Amendments dated Nov. 27, 2012 in Int'l PCT Patent Appl. Serial No. PCT/IL2011/000958 (0710).

Ataya et al., "A Review of Targeted Pulmonary Arterial Hypertension-Specific Pharmacotherapy," J. Clin. Med., 5(12):114 (2016).

"Atrium Advanta V12, Balloon Expandable Covered Stent, Improving Patient Outcomes with an Endovascular Approach," Brochure, 8 pages, Getinge (2017).

Bannan et al., "Characteristics of Adult Patients with Atrial Septal Defects Presenting with Paradoxical Embolism.," Catheterization and Cardiovascular Interventions, 74:1066-1069 (2009).

Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).

Beemath et al., "Pulmonary Embolism as a Cause of Death in Adults Who Died With Heart Failure," Am J Cardiol., 98:1073-1075 (2006).

Benza et al., "Monitoring Pulmonary Arterial Hypertension Using an Implantable Hemodynamic Sensor," Chest, 156(6):1176-1186 (2019).

Boehm, et al., "Balloon Atrial Septostomy: History and Technique," Images Paeditr. Cardiol., 8(1):8-14 (2006).

Borlaug, et al., Latent Pulmonary Vascular Disease May Alter the Response to Therapeutic Atrial Shunt Device in Heart Failure, Circulation (Mar. 2022).

Braunwald, Heart Disease, Chapter 6, pp. 186.

Bridges, et al., "The Society of Thoracic Surgeons Practice Guideline Series: Transmyocardial Laser Revascularization," Ann Thorac Surg., 77:1494-1502 (2004).

Bristow, et al., "Improvement in cardiac myocyte function by biological effects of medical therapy: a new concept in the treatment of heart failure," European Heart Journal, 16 (Suppl.F):20-31 (1995).

Bruch et al., "Fenestrated Occluders for Treatment of ASD in Elderly Patients with Pulmonary Hypertension and/or Right Heart Failure," J Interven Cardiol., 21(1):44-49 (2008).

Burkhoff et al., "Assessment of systolic and diastolic ventricular properties via pressure-volume analysis: a guide for clinical, translational, and basic researchers," Am J Physiol Heart Circ Physiol., 289:H501-H512 (2005).

Butler et al. "Recognizing Worsening Chronic Heart Failure as an Entity and an End Point in Clinical Trials," JAMA., 312(8):789-790 (2014).

Case, et al., "Relief of High Left-Atrial Pressure in Left-Ventricular Failure," Lancet, (pp. 841-842), Oct. 17, 1964.

Chakko et al., "Clinical, radiographic, and hemodynamic correlations in chronic congestive heart failure: conflicting results may lead to inappropriate care," Am J Medicine, 90:353-359 (1991) (Abstract Only).

Chang et al., "State-of-the-art and recent developments in micro/nanoscale pressure sensors for smart wearable devices and health monitoring systems," Nanotechnology and Precision Engineering, 3:43-52 (2020).

Chen et al., "Continuous wireless pressure monitoring and mapping with ultra-small passive sensors for health monitoring and critical care," Nature Communications, 5(1):1-10 (2014).

Chen et al., "National and Regional Trends in Heart Failure Hospitalization and Mortality Rates for Medicare Beneficiaries, 1998-2008," JAMA, 306(15):1669-1678 (2011).

Chiche et al., "Prevalence of patent foramen ovale and stroke in pulmonary embolism patients," Eur Heart J., 34:P1142 (2013) (Abstract Only).

Chin et al., "The right ventricle in pulmonary hypertension," Coron Artery Dis., 16(1):13-18 (2005) (Abstract Only).

Chun et al., "Lifetime Analysis of Hospitalizations and Survival of Patients Newly Admitted With Heart Failure," Circ Heart Fail., 5:414-421 (2012).

Ciarka et al., "Atrial Septostomy Decreases Sympathetic Overactivity in Pulmonary Arterial Hypertension," Chest, 131(6):p. 1831-1837 (2007) (Abstract Only).

Cleland et al., "The EuroHeart Failure survey programme—a survey on the quality of care among patients with heart failure in Europe—Part 1: patient characteristics and diagnosis," Eur Heart J., 24:442-463 (2003).

Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).

Coats, et al., "Controlled Trial of Physical Training in Chronic Heart Failure: Exercise Performance, Hemodynamics, Ventilation, and Autonomic Function," Circulation, 85: 2119-2131 (1992).

Davies et al., "Abnormal left heart function after operation for atrial septal defect," British Heart Journal, 32:747-753 (1970).

Davies, et al., "Reduced Contraction and Altered Frequency Response of Isolated Ventricular Myocytes From Patients With Heart Failure, Circulation," 92: 2540-2549 (1995).

Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).

Della Lucia et al., "Design, fabrication and characterization of SAW pressure sensors for offshore oil and gas exploration," Sensors and Actuators A: Physical, 222:322-328 (2015).

Drazner et al., "Prognostic Importance of Elevated Jugular Venous Pressure and a Third Heart Sound in Patients with Heart Failure," N Engl J Med., 345(8):574-81 (2001).

Drazner et al., "Relationship between Right and Left-Sided Filling Pressures in 1000 Patients with Advanced Heart Failure," Heart Lung Transplant, 18:1126-1132 (1999).

Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.

Eigler et al., "Cardiac Unloading with an Implantable Interatrial Shunt in Heart Failure: Serial Observations in an Ovine Model of Ischemic Cardiomyopathy," Structural Heart, 1:40-48 (2017).

Eigler, et al., Implantation and Recovery of Temporary Metallic Stents in Canine Coronary Arteries, JACC, 22(4):1207-1213 (1993).

Ennezat, et al., An unusual case of low-flow, low gradient severe aortic stenosis: Left-to-right shunt due to atrial septal defect, Cardiology, 113(2):146-148, (2009).

(56) References Cited

OTHER PUBLICATIONS

Eshaghian et al., "Relation of Loop Diuretic Dose to Mortality in Advanced Heart Failure," Am J Cardiol., 97:1759-1764 (2006).

Ewert, et al., Acute Left Heart Failure After Interventional Occlusion of an Artial Septal Defect, Z Kardiol, 90(5): 362-366 (May 2001).

Ewert, et al., Masked Left Ventricular Restriction in Elderly Patients With Atrial Septal Defects: A Contraindication for Closure?, Catheterization and Cardiovascular Intervention, 52:177-180 (2001).

Extended European Search Report dated Jan. 8, 2015 in EP Patent Appl No. 10772089.8. (0530).

Extended European Search Report dated Mar. 29, 2019 in EP Patent Appl. Serial No. EP16789391 (1830).

Extended European Search Report dated Sep. 19, 2016 in EP Patent Appl. No. 16170281.6 (0731).

Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).

Ferrari et al., "Impact of pulmonary arterial hypertension (PAH) on the lives of patients and carers: results from an international survey," Eur Respir J., 42:26312 (2013) (Abstract Only).

Flachskampf, et al., Influence of Orifice Geometry and Flow Rate on Effective Valve Area: An In Vitro Study, Journal of the American College of Cardiology, 15(5):1173-1180 (Apr. 1990).

Fonarow et al., "Characteristics, Treatments, and Outcomes of Patients With Preserved Systolic Function Hospitalized for Heart Failure," J Am Coll Cardiol., 50(8):768-777 (2007).

Fonarow et al., "Risk Stratification for In-Hospital Mortality in Acutely Decompensated Heart Failure: Classification and Regression Tree Analysis," JAMA, 293(5):572-580 (2005).

Fonarow, G., "The Treatment Targets in Acute Decompensated Heart Failure," Rev Cardiovasc Med., 2:(2):S7-S12 (2001).

Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).

Galie et al., "Pulmonary arterial hypertension: from the kingdom of the near-dead to multiple clinical trial meta-analyses," Eur Heart J., 31:2080-2086 (2010).

Galipeau et al., "Surface acoustic wave microsensors and applications," Smart Materials and Structures, 6(6):658-667 (1997) (Abstract Only).

Geiran, et al., Changes in cardiac dynamics by opening an interventricular shunt in dogs, J. Surg. Res. 48(1):6-12 (1990).

Gelernter-Yaniv, et al., Transcatheter ClosureoOf Left-To-Right Interatrial Shunts to Resolve Hypoxemia, Congenit. Heart Dis. 31(1): 47-53 (Jan. 2008).

Geva et al., "Atrial septal defects," Lancet, 383:1921-32 (2014).

Gewillig, et al., Creation with a stent of an unrestrictive lasting atrial communication, Cardio. Young 12(4): 404-407 (2002).

Gheorghiade et al., "Acute Heart Failure Syndromes, Current State and Framework for Future Research," Circulation, 112:3958-3968 (2005).

Gheorghiade et al., "Effects of Tolvaptan, a Vasopressin Antagonist, in Patients Hospitalized With Worsening Heart Failure a Randomized Controlled Trial," JAMA., 291:1963-1971 (2004).

Go et al. "Heart Disease and Stroke Statistics—2014 Update—A Report From the American Heart Association," Circulation, 128:1-267 (2014).

Greitz, et al., Pulsatile Brain Movement and Associated Hydrodynamics Studied by Magnetic Resonance Phase Imaging, Diagnostic Neuroradiology, 34(5): 370-380 (1992).

Guillevin et al., "Understanding the impact of pulmonary arterial hypertension on patients' and carers' lives," Eur Respir Rev., 22:535-542 (2013).

Guyton et al., "Effect of Elevated Left Atrial Pressure and Decreased Plasma Protein Concentration on the Development of Pulmonary Edema," Circulation Research, 7:643-657 (1959).

Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).

Hoeper et al., "Definitions and Diagnosis of Pulmonary Hypertension," J Am Coll Cardiol., 62(5):D42-D50 (2013).

Hogg et al., "Heart Failure With Preserved Left Ventricular Systolic Function. Epidemiology, Clinical Characteristics, and Prognosis," J Am Coll Cardiol., 43(3):317-327 (2004).

Howell et al., "Congestive heart failure and outpatient risk of venous thromboembolism: A retrospective, case-control study," Journal of Clinical Epidemiology, 54:810-816 (2001).

Huang et al., "Remodeling of the chronic severely failing ischemic sheep heart after coronary microembolization: functional, energetic, structural, and cellular responses," Am J Physiol Heart Circ Physiol., 286:H2141-H2150 (2004).

Humbert et al., "Pulmonary Arterial Hypertension in France—Results from a National Registry," Am J Respir Crit Care Med., 173:1023-1030 (2006).

International Search Report & Written Opinion dated Nov. 7, 2016 in Int'l PCT Patent Appl. Serial No. PCT/IB2016/052561 (1810).

International Search Report & Written Opinion dated May 29, 2018 in Int'l PCT Patent Appl. Serial No. PCT/IB2018/051385 (1310).

International Search Report & Written Opinion dated Feb. 3, 2023 in Int'l PCT Patent Appl. Serial No. PCT/IB2022/060621 (2210).

International Search Report & Written Opinion dated Feb. 6, 2013 in Int'l PCT Patent Appl. No. PCT/IB2012/001859, 12 pages (0810).

International Search Report & Written Opinion dated Feb. 7, 2020 in Int'l PCT Patent Appl. Serial No. PCT/IB2019/060257 (1410).

International Search Report & Written Opinion dated Feb. 9, 2022 in Int'l PCT Patent Appl. Serial No. PCT/IB2021/060473 (2010).

International Search Report & Written Opinion dated Mar. 29, 2023 in Int'l PCT Patent Appl. Serial No. PCT/IB2023/050743 (2410).

International Search Report & Written Opinion dated May 13, 2019 in Int'l PCT Patent Appl. No. PCT/IB2019/050452 (1610).

International Search Report & Written Opinion dated May 17, 2022 in Int'l PCT Patent Appl. Serial No. PCT/IB2022/051177 (2310).

International Search Report & Written Opinion dated May 29, 2018 in Int'l PCT Patent Appl. Serial No. PCTIB2018/051355 (1310).

International Search Report & Written Opinion dated Jul. 14, 2020 in Int'l PCT Patent Appl. Serial No. PCT/IB2020/053832 (1210).

International Search Report & Written Opinion dated Jul. 20, 2020 in Int'l PCT Patent Appl. Serial No. PCT/IB2020/054699 (1710).

International Search Report & Written Opinion dated Jul. 23, 2021 in Int'l PCT Patent Appl. Serial No. PCT/IB2021/053594 (1910).

International Search Report & Written Opinion dated Aug. 12, 2020 in Int'l PCT Patent Appl. Serial No. PCT/IB2020/053118 (1010).

International Search Report & Written Opinion dated Aug. 28, 2012 in Int'l PCT Patent Appl. No. PCT/IL2011/000958 (0710).

International Search Report & Written Opinion dated Sep. 21, 2020 in Int'l PCT Patent Appl. Serial No. PCT/IB2020/054306 (1510).

International Search Report & Written Opinion dated Oct. 11, 2017 in Int'l PCT Patent Appl. Serial No. PCT/IB2017/053188 (1110).

International Search Report & Written Opinion dated Oct. 26, 2007 in Int'l PCT Patent Appl. Serial No. PCT/IB07/50234 (0610).

International Search Report dated Apr. 7, 2008 in Int'l PCT Patent Appl. Serial No. PCT/IL05/00131 (0410).

International Search Report dated Aug. 25, 2010 in Intl PCT Patent Appl. Serial No. PCT/IL2010/000354 (0510).

ISR & Written Opinion dated Feb. 16, 2015 in Int'l PCT Patent Appl. Serial No. PCT/IB2014/001771 (0910).

Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).

Jiang, G., "Design challenges of implantable pressure monitoring system," Frontiers in Neuroscience, 4(29):1-4 (2010).

(56) References Cited

OTHER PUBLICATIONS

Kane et al., "Integration of clinical and hemodynamic parameters in the prediction of long-term survival in patients with pulmonary arterial hypertension," Chest, 139(6):1285-1293 (2011) (Abstract Only).

Kaye et al., "Effects of an Interatrial Shunt on Rest and Exercise Hemodynamics: Results of a Computer Simulation in Heart Failure," Journal of Cardiac Failure, 20(3): 212-221 (2014).

Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).

Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).

Keogh et al., "Interventional and Surgical Modalities of Treatment in Pulmonary Hypertension," J Am Coll Cardiol., 54:S67-77 (2009).

Keren, et al. Methods and Apparatus for Reducing Localized Circulatory System Pressure,., Jan. 7, 2002 (pp. 16).

Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).

Kramer, et al., Controlled Trial of Captopril in Chronic Heart Failure: A Rest and Exercise Hemodynamic Study, Circulation, 67(4): 807-816, 1983.

Kretschmar et al., "Shunt Reduction With a Fenestrated Amplatzer Device," Catheterization and Cardiovascular Interventions, 76:564-571 (2010).

Kropelnicki et al., "CMOS-compatible ruggedized high-temperature Lamb wave pressure sensor," J. Micromech. Microeng., 23:085018 pp. 1-9 (2013).

Krumholz et al., "Patterns of Hospital Performance in Acute Myo-cardial Infarction and Heart Failure 30-Day Mortality and Read-mission," Circ Cardiovasc Qual Outcomes, 2:407-413 (2009).

Kulkarni et al., "Lutembacher's syndrome," J Cardiovasc Did Res., 3(2):179-181 (2012).

Kurzyna et al., "Atrial Septostomy in Treatment of End-Stage Right Heart Failure in Patients With Pulmonary Hypertension," Chest, 131:977-983 (2007).

Lai et al., Bidirectional Shunt Through a Residual Atrial Septal Defect After Percutaneous Transvenous Mitral Commissurotomy, Cadiology, 83(3): 205-207 (1993).

Lammers et al., "Efficacy and Long-Term Patency of Fenerstrated Amplatzer Devices in Children," Catheter Cardiovasc Interv., 70:578-584 (2007).

Lemmer, et al., Surgical Implications of Atrial Septal Defect Com-plicating Aortic Balloon Valvuloplasty, Ann. thorac. Surg, 48(2):295-297 (Aug. 1989).

Lindenfeld et al. "Executive Summary: HFSA 2010 Comprehensive Heart Failure Practice Guideline," J. Cardiac Failure, 16(6):475-539 (2010).

Luo, Yi, *Selective and Regulated RF Heating of Stent Toward Endohyperthermia Treatment of In-Stent Restenosis*, A Thesis Sub-mitted in Partial Fulfillment of the Requirements for the Degree of Master of Applied Science in the Faculty of Graduate and Postdoc-toral Studies (Electrical and Computer Engineering), The Univer-sity of British Columbia, Vancouver, Dec. 2014.

MacDonald et al., "Emboli Enter Penetrating Arteries of Monkey Brain in Relation to Their Size," Stroke, 26:1247-1251 (1995).

Maluli et al., "Atrial Septostomy: A Contemporary Review," Clin. Cardiol., 38(6):395-400 (2015).

Maurer et al., "Rationale and Design of the Left Atrial Pressure Monitoring to Optimize Heart Failure Therapy Study (LAPTOP-HF)," Journal of Cardiac Failure., 21(6): 479-488 (2015).

McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).

McLaughlin et al., "Management of Pulmonary Arterial Hyperten-sion," J Am Coll Cardiol., 65(18):1976-1997 (2015).

McLaughlin et al., "Survival in Primary Pulmonary Hypertension—The Impact of Epoprostenol Therapy.," Circulation, 106:1477-1482 (2002).

Merriam-Webster OnLine Dictionary, Definition of "chamber", printed Dec. 20, 2004.

Mu et al., "Dual mode acoustic wave sensor for precise pressure reading," Applied Physics Letters, 105:113507-1-113507-5 (2014).

Nagaraju et al., "A 400µW Differential FBAR Sensor Interface IC with digital readout," IEEE., pp. 218-221 (2015).

Noordegraaf et al., "The role of the right ventricle in pulmonary arterial hypertension," Eur Respir Rev., 20(122):243-253 (2011).

O'Byrne et al., "The effect of atrial septostomy on the concentration of brain-type natriuretic peptide in patients with idiopathic pulmo-nary arterial hypertension," Cardiology in the Young, 17(5):557-559 (2007) (Abstract Only).

Oktay et al., "The Emerging Epidemic of Heart Failure with Preserved Ejection Fraction," Curr Heart Fail Rep., 10(4):1-17 (2013).

Owan et al., "Trends in Prevalence and Outcome of Heart Failure with Preserved Ejection Fraction," N Engl J Med., 355:251-259 (2006).

Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).

Park Blade Septostomy Catheter Instructions for Use, Cook Medi-cal, 28 pages, Oct. 2015.

Park, et al., Blade Atrial Septostomy: Collaborative Study, Circu-lation, 66(2):258-266 (1982).

Partial Supplemental European Search Report dated Dec. 11, 2018 in EP Patent Appl. Serial No. 16789391.6 (1830).

Peters et al., "Self-fabricated fenestrated Amplatzer occluders for transcatheter closure of atrial septal defect in patients with left ventricular restriction: midterm results," Clin Res Cardiol., 95:88-92 (2006).

Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).

Potkay, J. A., "Long term, implantable blood pressure monitoring systems," Biomed Microdevices, 10:379-392 (2008).

Pretorious et al., "An Implantable Left Atrial Pressure Sensor Lead Designed for Percutaneous Extraction Using Standard Techniques," PACE, 00:1-8 (2013).

Rajeshkumar et al., "Atrial septostomy with a predefined diameter using a novel occlutech atrial flow regulator improves symptoms and cardiac index in patients with severe pulmonary arterial hyper-tension," Catheter Cardiovasc Interv., 1-9 (2017).

Rich et al., "Atrial Septostomy as Palliative Therapy for Refractory Primary Pulmonary Hypertension," Am J Cardiol., 51:1560-1561 (1983).

Ritzema et al., "Direct Left Atrial Pressure Monitoring in Ambu-latory Heart Failure Patients—Initial Experience With a New Per-manent Implantable Device," Circulation, 116:2952-2959 (2007).

Ritzema et al., "Physician-Directed Patient Self-Management of Left Atrial Pressure in Advanced Chronic Heart Failure," Circula-tion, 121:1086-1095 (2010).

Roberts et al., "Integrated microscopy techniques for comprehen-sive pathology evaluation of an implantable left atrial pressure sensor," J Histotechnology, 36(1):17-24 (2013).

Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin. 2018.07.001 (2018).

Rosenquist et al., Atrial Septal Thickness and Area in Normal Heart Specimens and in Those With Ostium Secundum Atrial Septal Defects, J. Clin. Ultrasound, 7:345-348 (1979).

Ross et al., "Interatrial Communication and Left Atrial Hyperten-sion—A Cause of Continuous Murmur," Circulation, 28:853-860 (1963).

(56)                    References Cited

OTHER PUBLICATIONS

Rossignol, et al., Left-to-Right Atrial Shunting: New Hope for Heart Failure, www.thelancet.com, 387:1253-1255 (2016).

Roven, Effect of Compromising Right Ventricular Function in Left Ventricular Failure by Means of Interatrial and Other Shunts 24:209-219 (Aug. 1969).

Salehian, et al., Improvements in Cardiac Form and Function After Transcatheter Closure of Secundum Atrial Septal Defects, Journal of the American College of Cardiology, 45(4):499-504 (2005).

Sandoval et al., "Effect of atrial septostomy on the survival of patients with severe pulmonary arterial hypertension," Eur Respir J., 38:1343-1348 (2011).

Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).

Schiff et al., "Decompensated heart failure: symptoms, patterns of onset, and contributing factors," Am J. Med., 114(8):625-630 (2003) (Abstract Only).

Schmitto, et al., Chronic Heart Failure Induced by Multiple Sequential Coronary Microembolization in sheep, The International Journal of Artificial Organs, 31(4):348-353 (2008).

Schneider et al., "Fate of a Modified Fenestration of Atrial Septal Occluder Device after Transcatheter Closure of Atrial Septal Defects in Elderly Patients," J Interven Cardiol., 24:485-490 (2011).

Scholl et al., "Surface Acoustic Wave Devices for Sensor Applications," Phys Status Solidi Appl Res., 185(1):47-58 (2001) (Abstract Only).

Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).

Setoguchi et al., "Repeated hospitalizations predict mortality in the community population with heart failure," Am Heart J., 154:260-266 (2007).

Shah, et al., Atrial Shunt Device For Heart Failure With Preserved And Mildly Reduced Ejection Fraction (Reduce LAP-HF II): A Randomised, Multicentre, Blinded, Sham-Controlled Trial, The Lancet, 399(10330):1130-1140 (Mar. 2022).

Shah et al., "Heart Failure With Preserved, Borderline, and Reduced Ejection Fraction—5-Year Outcomes," J Am Coll Cardiol., https://doi.org/10.1016/j.jacc.2017.08.074 (2017).

Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).

Sitbon et al., "Selexipag for the Treatment of Pulmonary Arterial Hypertension.," N Engl J Med., 373(26):2522-2533 (2015).

Sitbon et al., "Epoprostenol and pulmonary arterial hypertension: 20 years of clinical experience," Eur Respir Rev., 26:160055:1-14 (2017).

Steimle et al., "Sustained Hemodynamic Efficacy of Therapy Tailored to Reduce Filling Pressures in Survivors With Advanced Heart Failure," Circulation, 96:1165-1172 (1997).

Stevenson et al., "The Limited Reliability of Physical Signs for Estimating Hemodynamics in Chronic Heart Failure," JAMA, 261(6):884-888 (1989) (Abstract Only).

Stormer, et al., Comparative Study of in Vitro Flow Characteristics Between a Human Aortic Valve and a Designed Aortic Valve and Six Corresponding Types of Prosthetic Heart Valves, European Surgical Research 8(2):117-131 (1976).

Stumper, et al., Modified Technique of Stent Fenestration of the Atrial Septum, Heart, 89:1227-1230, (2003).

Su et al., "A film bulk acoustic resonator pressure sensor based on lateral field excitation," International Journal of Distributed Sensor Networks, 14(11):1-8 (2018).

Supplementary European Search Report dated Nov. 13, 2009 in EP Patent Appl. Serial No. 05703174.2 (0430).

Thenappan et al., "Evolving Epidemiology of Pulmonary Arterial Hypertension," Am J Resp Critical Care Med., 186:707-709 (2012).

Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).

Torbicki et al., "Atrial Septostomy," The Right Heart, 305-316 (2014).

Trainor, et al., Comparative Pathology of an Implantable Left Atrial Pressure Sensor, ASAIO Journal, Clinical Cardiovascular/Cardiopulmonary Bypass, 59(5):486-492 (2013).

Troost et al., "A Modified Technique of Stent Fenestration of the Interatrial Septum Improves Patients With Pulmonary Hypertension," Catheterization and Cardiovascular Interventions, 73:173179 (2009).

Troughton et al., "Direct Left Atrial Pressure Monitoring in Severe Heart Failure: Long-Term Sensor Performance," J. of Cardiovasc. Trans. Res., 4:3-13 (2011).

Vank-Noordegraaf et al., "Right Heart Adaptation to Pulmonary Arterial Hypertension—Physiology and Pathobiology," J Am Coll Cardiol., 62(25): D22-33 (2013).

Verel et al., "Comparison of left atrial pressure and wedge pulmonary capillary pressure—Pressure gradients between left atrium and left ventricle," British Heart J., 32:99-102 (1970).

Viaene et al., "Pulmonary oedema after percutaneous ASD-closure," Acta Cardiol., 65(2):257-260 (2010).

Wang et al., "A Low Temperature Drifting Acoustic Wave Pressure Sensor with an Integrated Vacuum Cavity for Absolute Pressure Sensing," Sensors, 20(1788):1-13 (2020).

Wang et al., "Tire Pressure Monitoring System and Wireless Passive Surface Acoustic Wave Sensor," Appl Mech Mater., 536(537):333-337 (2014).

Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).

Webb et al., "Atrial Septal Defects in the Adult Recent Progress and Overview," Circulation, 114:1645-1653 (2006).

Wiedemann, H.R., "Earliest description by Johann Friedrich Meckel, Senior (1750) of what is known today as Lutembacher syndrome (1916)," Am J Med Genet., 53(1):59-64 (1994) (Abstract Only).

Written Opinion of the International Searching Authority dated Apr. 7, 2008 in Int'l PCT Patent Appl. Serial No. PCT/IL05/00131 (0410).

Yantchev et al., "Thin Film Lamb Wave Resonators in Frequency Control and Sensing Applications: A Review," Journal of Micromechanics and Microengineering, 23(4):043001 (2013).

Zhang et al., "Acute left ventricular failure after transcatheter closure of a secundum atrial septal defect in a patient with hypertrophic cardiomyopathy," Chin Med J., 124(4):618-621 (2011).

Zhang et al., "Film bulk acoustic resonator-based high-performance pressure sensor integrated with temperature control system," J Micromech Microeng., 27(4):1-10 (2017).

Zhou, et al., Unidirectional Valve Patch for Repair of Cardiac Septal Defects with Pulmonary Hypertension, Annals of Thoracic Surgeons, 60:1245-1249, (1995).

Extended EP Search Report dated Jan. 24, 2025 in EP Patent Appl. Serial No. 24202131.9 (103002).

Ge, et al., Feasability of a novel implantable device to provide heart failure therapy and left atrial pressure monitoring in a chronic animal study, ESC Congress 2025, (Aug. 29, 2025), available at https://esc365.escardio.org/presentation/306434.

Hibbert, Benjamin et al., Left Atrial to Coronary Sinus Shunting for Treatment of Symptomatic Heart Failure, JACC: Cardiovascular Interventions, vol. 16, No. 11 (Jun. 12, 2023).

Horvay, et al., Development of Nitinol Alloys for Additive Manufacturing, Materials Science and Technology pp. 63-70 (2018).

International Preliminary Report on Patentability_PCT/IB2022/060621 Dated May 2, 2024.

International Search Report & Written Opinion dated Jan. 15, 2025 in Int'l PCT Patent Appl. Serial No. PCT/IB2024/060159 (271001).

(56)     References Cited

OTHER PUBLICATIONS

O'Riordan, Michael, The Hole Story: Interatrial Shunt Companies Are-Mostly-Pushing Ahead, tctmd.com, available at https://www.tctmd.com/news/hole-story-interatrial-shunt-companies-are-mostly-pushing-ahead (Jun. 20, 2024).

Patel et al., Atrial Shunt Device Effects on Cardiac Structure and Function in Heart Failure With Preserved Ejection Fraction, JAMA Cardiology (Apr. 17, 2024).

Pfeiffer, In vivo fluid dynamics of the Ventura interatrial shunt device in patients with heart failure, ESC Heart Failure, DOI: 10.1002/ehf2.14859 (May 22, 2024).

Pocock, et al., Prognostic Modeling of Individual Patient Risk and Mortality Impact of Ischemic and Hemorrhagic Complications, Assessment From the Acute Catheterization and Urgent Intervention Triage Strategy Trial, *Circulation*, 121(1):43-51 (Jan. 2010).

RELIEVE-HF: Does Impact of Interatrial Shunting Differ by HF Type? American College of Cardiology (ACC), available at: https://www.acc.org/Latest-in-Cardiology/Articles/2024/04/02/sat-930am-relieve-hf-acc-2024 (Apr. 6, 2024).

Rodes-Cabau, et al., Interatrial shunt therapy in advanced heart failure: Outcomes from the open-label cohort of the RELIEVE-HF trial, Eur. J. Heart. Fail., 26(4):1078-1089 (Apr. 2024).

Shah, Sanjiv et al.: Supplemental Materials to Atrial shunt device for heart failure with preserved and mildly reduced ejection fraction (Reduce LAP-HF II): a randomised, multicentre, blinded, sham-controlled trial, The Lancet, vol. 399, Issue 10330 p1130-1140, available at: https://www.thelancet.com/journals/lancet/article/PIIS0140-6736(22)00016-2/abstract (Mar. 19, 2022).

Shah, Sanjiv J., RELIEVE-HF Trial: Discussant, ACC.24 (Apr. 6, 2024).

Simard, Trevor et al., Percutaneous Atriotomy for Levoatrial-to-Coronary Sinus Shunting in Symptomatic Heart Failure, JACC: Cardiovascular Interventions, vol. 13, No. 10 (May 25, 2020).

Stone, et al., Supplemental Material-3 to Interatrial Shunt Treatment for Heart Failure: The Randomized RELIEVE-HF Trial, Circulation, 150(24):1931-1943 (Dec. 2024).

Stone, Gregg, A Double-blind, Randomized Placebo-Procedure-Controlled Trial of an Interatrial Shunt in Patients with HFrEF and HFpEF: Principal Results from the RELIEVE-HF Trial, American College of Cardiology (ACC) (Apr. 6, 2024).

Stone, Gregg et al.: Supplemental Material 1—Interatrial Shunt Treatment for Heart Failure: The Randomized RELIEVE-HF Trial, available at: https://www.ahajournals.org/doi/suppl/10.1161/CIRCULATIONAHA.124.070870 (Dec. 10, 2024).

Stone, Gregg et al.: Supplemental Materials 2 to Interatrial Shunt Treatment for Heart Failure: The Randomized RELIEVE-HF Trial, available at: https://www.ahajournals.org/doi/suppl/10.1161/CIRCULATIONAHA.124.070870 (Dec. 10, 2024).

Stone, Gregg W., Predictors of Outcomes After Inter-Atrial Shunt Treatment in HFrEF and HFpEF: The RELIEVE-HF trial, THT 2025 (Feb. 11, 2025).

Stone, Interatrial Shunt Treatment for Heart Failure: The Randomized RELIEVE-HF Trial, Circulation. 2024; 150:1931-1943. DOI: 10.1161/CIRCULATIONAHA.124.070870 (Dec. 10, 2024).

Sullivan, et al., Tutorial in Biostatistics, Presentation of multivariate data for clinical use: The Framingham Study risk score functions, Statistics in Medicine, Statist. Med., 23:1631-1660 (2004).

* cited by examiner

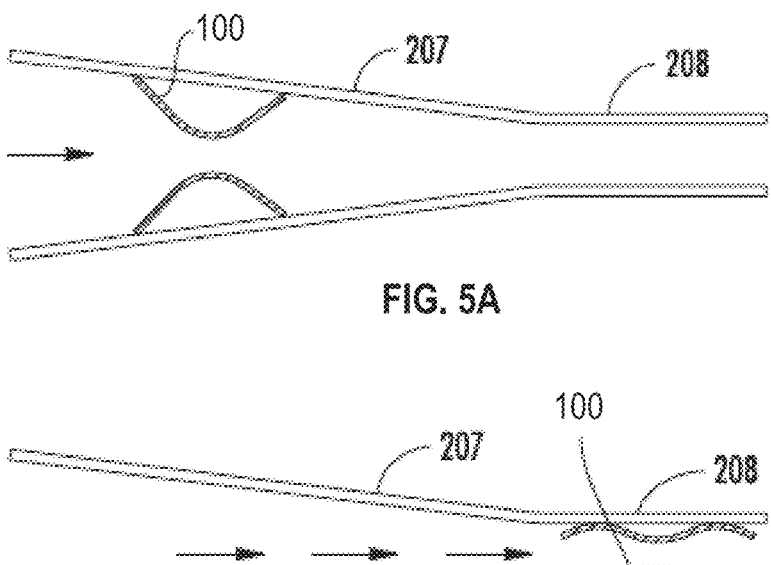
FIG. 5A
FIG. 5B
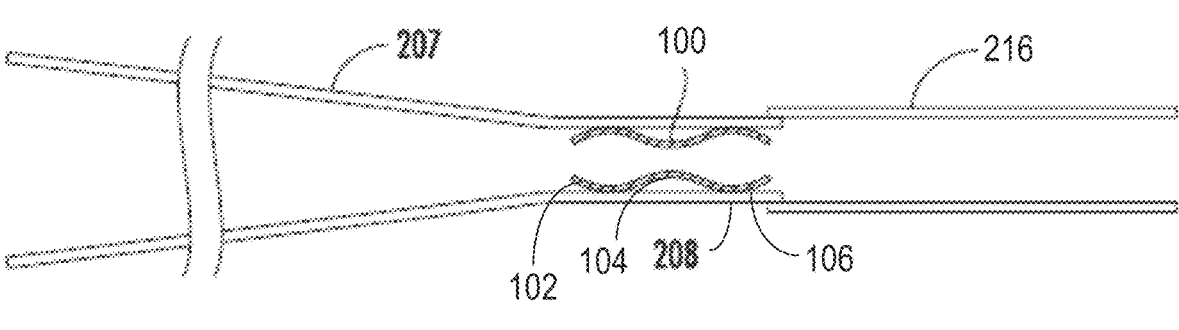
FIG. 5C

| | |
|---|---|
| ⬜ | 1st Layer |
| ⬜ | 2nd Layer |
| ⬜ | Frame |

1600

Deliver shunt to atrial septum in contracted state — 1602

Deploy shunt at atrial septum to expanded state such that neck region is disposed within atrial septum — 1604

Expand neck region of shunt from first diameter to second diameter — 1606

Selectively heat shunt to predetermined temperature to thermally contract neck region to predetermined third diameter — 1608

INTERATRIAL SHUNT WITH EXPANDED NECK REGION

CROSS-REFERENCE TO RELATED APPLICATIONS

This application is a continuation of U.S. patent application Ser. No. 18/300,092, filed Apr. 13, 2023, now U.S. Pat. No. 11,813,386, which claims priority to U.S. Provisional Patent Application No. 63/386,147, filed Dec. 5, 2022, and U.S. Provisional Patent Application No. 63/363,015, filed Apr. 14, 2022, the entire contents of each of which are incorporated herein by reference.

TECHNICAL FIELD

The technology relates to devices for use in the human body, such as percutaneously implanted devices, including devices for regulating pressure within the circulatory system such as interatrial shunts for regulating blood pressure in a heart, and methods for the manufacture of such devices.

BACKGROUND

For a number of medical conditions, there is benefit in adjusting the flow of fluid within the human body, for example, through a passage between two body cavities. Such a passage is typically used in catheterization procedures where the catheter is delivered through a patient's vasculature. In some catheterization procedures, there is a benefit in moving from one cavity to another cavity by creating a passage. For example, such a passage may be formed between the right side of the heart and the left side of the heart, e.g., between the right atrium toward the left atrium, where clinical procedures are done on the left side of the heart using an entry from the right side of the heart. Such clinical procedures include, e.g., arrhythmia ablation procedures in the left atrium and mitral valve repair activities.

In addition, a passage may be created and maintained in a heart wall between two heart chambers for housing a shunt for redistributing blood from one heart chamber to another to address pathologies such as heart failure (HF), myocardial infarction (MI), and pulmonary arterial hypertension (PAH). HF is the physiological state in which cardiac output is insufficient to meet the needs of the body or to do so only at a higher filling pressure. There are many underlying causes of HF, including MI, coronary artery disease, valvular disease, hypertension (such as PAH), and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

HF is generally classified as either systolic heart failure ("SHF") or diastolic heart failure ("DHF"). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction ("HFrEF"). A patient with HFrEF may usually have a larger left ventricle because of a phenomenon called "cardiac remodeling" that occurs secondarily to the higher ventricular pressures.

In DHF, the heart generally contracts well, with a normal ejection fraction, but is stiffer, or less compliant, than a healthy heart would be when relaxing and filling with blood. Such patients are said to have heart failure with preserved ejection fraction ("HFpEF"). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, neprilysin inhibitors, beta blockers, mineralocorticoid antagonists and sodium-glucose co-transporter-2 (SGLT2) inhibitors. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, mechanical circulatory support (MCS) devices such as mechanical pumps are used to reduce the load on the heart by performing all or part of the pumping function normally done by the heart. Chronic left ventricular assist devices ("LVAD"), the total artificial heart, and cardiac transplantation are used as measures of last resort. However, such assist devices typically are intended to improve the pumping capacity of the heart, to increase cardiac output to levels compatible with normal life, and to sustain the patient until a donor heart for transplantation becomes available. This usage of MCS is also known as "bridge to transplant" therapy". As the supply of donor hearts for transplantation is insufficient for the demand, more often MCS is the only therapeutic option—also known as "destination therapy." Such mechanical devices enable propulsion of significant volumes of blood (liters/min) but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having balloon-expandable lobed or conical portions joined by a shape-memory constricted region, which limits flow through the stent. The constricted region may be adjusted in vivo, and in addition may be heated to recover a maximum degree of constriction. Ruiz is silent on the treatment of HF or the reduction of left atrial pressure.

U.S. Patent Publication No. 2013/0178784 to McNamara describes an adjustable pressure relief shunt that may be expanded, e.g., via an inflation balloon. A tubular body of the shunt may be plastically deformed in vivo, such that the size of the shunt may be repeatedly adjusted by a variety of mechanisms, for example, elastically wound springs or a series of pawls and one-way mechanical ramps, responsive to measurements of the patient's physiological parameters. A key drawback to the approach described in that patent is the hysteresis effect, i.e., non-reversible changes in the underlying crystalline structure that occur when the shunt is permanently deformed. Importantly, such plastic deformation may lead to stress and fatigue-related fracture of the device. Another drawback of the system is that expanding or reducing the encapsulated shunt after tissue has adhered to the shunt over time can result in trauma to the atrial septum.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome ("HLHS"). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium ("LA") to the right atrium ("RA"), the pressure in the left atrium is lowered or prevented from elevating as high as it would otherwise (left atrial decompression). Such an accomplishment would be expected to prevent, relieve, or limit the symptoms, signs, and syndromes associated of pulmonary congestion. These include severe shortness of breath, pulmonary edema, hypoxia, the need for acute hospitalization, mechanical ventilation, and death.

Shunt flow is generally governed by the pressure gradient between the atria and the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is generally placed from an entrance site in the femoral vein, across the interatrial septum in the region of fossa ovalis ("FO"), which is the central and thinnest region of the interatrial septum. The FO in adults is typically 15-20 mm in its major axis dimension and <3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty type balloon across the FO. This is the same general location where a congenital secundum atrial septal defect ("ASD") would be located.

U.S. Patent Publication No. 2005/0165344 to Dobak, III describes apparatus for treating heart failure that includes a tubular conduit having an emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

In addition, following implantation of a shunt device within a heart wall, tissue ingrowth including an endothelial layer or neointima layer typically forms on the device, thereby inhibiting thrombogenicity of the shunt device. Shunt adjustments following tissue ingrowth at the atrial septum could present risks if the shunt is pulled away from the ingrown tissue at the atrial septum during the adjustments. Additionally, or alternatively, anchoring in an atrial septum with a relatively large hole, for example, caused by a transseptal intervention such as MitraClip® insertion, could present challenges with shunt securement. As such, there is a need for an interatrial shunt that is safely adjustable and/or can securely anchor within relatively large septal holes.

SUMMARY

Described herein are apparatus and methods for making and using improved interatrial shunts to improve treatment and outcomes for patients with cardiovascular and cardiopulmonary disorders, including heart failure (HF) and pulmonary arterial hypertension (PAH). The interatrial shunts may be particularly well-suited for in vivo adjustments of the size of the flow path through the shunt and/or for use in a relatively large hole in the septum (e.g., post-transseptal intervention).

The device may be designed to shunt blood between a patient's first atrium and second atrium to treat a medical condition. The device may include an encapsulated shunt comprising a first flared end region, a second flared end region, and a neck region disposed therebetween. The encapsulated shunt may be formed from a frame encapsulated in biocompatible material, such as ePTFE, such that it defines a passageway to permit blood to flow from the first atrium to the second atrium via the passageway. The device may further include a bridge extending from a first outer surface of the first flared end region to a second outer surface of the second flared end region. The bridge may be formed of biocompatible material and configured to engage the patient's atrial septum.

The bridge may be configured to engage the patient's atrial septum, rather than the encapsulated shunt itself such that, when the device is adjusted in vivo, the bridge may be configured to remain the same outer diameter while only the inner diameter of the shunt is modified. The bridge preferably is designed to prevent dehiscence and to mitigate the tissue trauma that can result from such adjustments. The bridge may further be configured to maintain contact with the septal tissue such that leakage or bypass flow around the outer surface of the shunt is minimized. In addition, the bridge may be used with encapsulated shunts that are not adjustable in vivo. For example, incorporating the bridge of biocompatible material to the encapsulated shunt increases the outer diameter of the device, thus permitting implantation of the device in enlarged septal holes, without affecting the inner diameter of the device and fluid flow rate throughout the device.

In accordance with another aspect of the present disclosure, a shunt for implantation within an atrial septum to treat a heart condition is provided. The shunt may include a single, metallic frame comprising a proximal end region, a distal end region, and a middle region disposed therebetween. The proximal and distal end regions each may be configured to self-expand upon deployment such that the middle region is positioned in an opening in the atrial septum. Moreover, the single, metallic frame may be heat treated such that the middle region is adjustable in vivo between a first diameter and a second diameter larger than the first diameter, and the middle region may be selectively thermally contractible from the second diameter to a third diameter larger than the first diameter. For example, the middle region may be heat treated to exhibit a martensitic finish temperature and an austenitic finish temperature greater than the martensitic finish temperature, such that the middle region may be selectively thermally contractible by being heated to a temperature between the martensitic finish temperature and the austenitic finish temperature.

The middle region may be malleable at body temperature and may comprise NITINOL having an austenitic finish temperature between 45-60° C. The proximal and distal end regions may be superelastic and may comprise NITINOL having an austenitic finish temperature between 5-20° C. Moreover, the middle region may be heat treated to exhibit different shape memory properties than the proximal and distal end regions. In addition, the middle region may comprise a plastically deformable material, such that the middle region may be configured to be expanded in vivo via mechanical expansion. The proximal and distal end regions and the middle region may define a diabolo-shaped shunt.

The system further may include a biocompatible material coating the proximal end region, the distal end region, and the middle region to define a passageway to permit blood to flow through the atrial septum via the shunt. The cross-sectional flow area in the passageway may be smallest at the middle region. Further, the passageway may be sized and shaped to permit a sufficient amount of blood to flow through the atrial septum via the shunt to treat pulmonary artery hypertension. Additionally or alternatively, the passageway may be sized and shaped to permit a sufficient amount of blood to flow through the atrial septum via the shunt to treat heart failure. In some embodiments, the system further may include a bridge extending from a first outer surface of the proximal end region to a second outer surface of the distal end region. The bridge may be formed of biocompatible material and configured to engage the atrial septum. Moreover, the bridge may define an outer diameter larger than the second diameter. For example, the bridge may extend to form a gap between an inner surface of the bridge and an outer surface at the middle region, such that, when the middle region is expanded in vivo, the gap may be configured to decrease in size and the outer diameter may be configured to remain the same diameter. Additionally or alternatively, the bridge may extend to form a gap between an inner surface of the bridge and an outer surface at the middle region, such that, when the middle region is contracted in vivo, the gap is configured to increase in size and the outer diameter is configured to remain in contact with the septum.

In accordance with another aspect of the present disclosure, a system for treating a heart condition comprising the shunt is provided. For example, the system may further include a catheter configured to inject heated fluid to the shunt in vivo to heat the shunt in vivo to selectively thermally contract the middle region from the second diameter to the third diameter. For example, the heated fluid may have an initial fluid temperature selected to reach a target fluid temperature at the shunt in vivo based on at least one of an injection rate of the heated fluid or a size of the catheter to thereby heat at least the middle region of the shunt to a target shunt temperature. Moreover, the catheter may comprise a temperature sensor disposed on a distal tip of the catheter, the temperature sensor configured to generate a signal indicative of a temperature of heated fluid delivered within the shunt. The catheter may be sized and shaped to inject heated fluid at an injection rate selected to minimize dilution and washout of the heated fluid in vivo. In some embodiments, the system may include an inflatable balloon configured to be disposed adjacent to the distal end region in an expanded state to block the flow of blood through the shunt during injection of the heated fluid to minimize dilution and washout of the heated fluid in vivo.

In addition, the system further may include a power injector fluidic ally coupled to the catheter to inject heated fluid through the catheter. The power injector may be operatively coupled to the temperature sensor and programmed to adjust at least one of a rate or duration of heated fluid injection through the catheter responsive to the signal. The power injector may be programmed to automatically terminate injection of heated fluid through the catheter when the temperature of the heated fluid delivered within the shunt reaches a predetermined temperature sufficient to selectively thermally contract the middle region of the shunt to the third diameter. Moreover, the power injector may be programmed to modulate the rate of heated fluid injection through the catheter to maintain the temperature of the heated fluid delivered within the shunt for a predetermined time period.

In accordance with yet another aspect of the present invention, a method for treating a heart condition is provided. The method may include: delivering a shunt to an opening in the atrial septum in a contracted state, the shunt comprising a frame having proximal and distal end regions and a middle region disposed therebetween, the frame heat treated such that the middle region is adjustable in vivo between a first diameter and a second diameter larger than the first diameter; deploying the shunt within the opening to an expanded state wherein the proximal end region self-expands within a first atrium, the distal end region self-expands within a second atrium, and the middle region is disposed at the atrial septum; expanding the middle region of the shunt from the first diameter to the second diameter in vivo; and selectively thermally contracting the middle region of the shunt in vivo from the second diameter to a third diameter larger than the first diameter.

Expanding the middle region of the shunt may comprise mechanically expanding the middle region of the shunt. Moreover, selectively thermally contracting the middle region of the shunt may comprise heating the middle region to a temperature between the martensitic finish temperature and the austenitic finish temperature, e.g., by injecting heated fluid to the shunt in vivo via a catheter to heat at least the middle region of the shunt. The method further may include measuring a temperature of heated fluid delivered within the shunt via a temperature sensor disposed at a distal tip of the catheter, and adjusting at least one of a rate or duration of heated fluid injection through the catheter based on the measured temperature of the heated fluid delivered within the shunt. In addition, the method may include automatically terminating injection of heated fluid through the catheter when the temperature of heated fluid delivered within the shunt reaches a predetermined temperature sufficient to selectively thermally contract the middle region of the shunt to the third diameter, and/or modulating the rate of heated fluid injection through the catheter to maintain the temperature of the heated fluid delivered within the shunt for a predetermined time period. The method further may include expanding an inflatable balloon adjacent to the distal end region of the shunt to an expanded state to block blood flow through the shunt during injection of the heated fluid to minimize dilution and washout of the heated fluid in vivo. Moreover, the method may include permitting a sufficient amount of blood to flow through the atrial septum via the shunt to treat pulmonary artery hypertension and/or heart failure.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

FIGS. 5A-5E are side views sequentially illustrating a technique of depositing a first graft portion on a shunt.

DETAILED DESCRIPTION

Figure 1A:
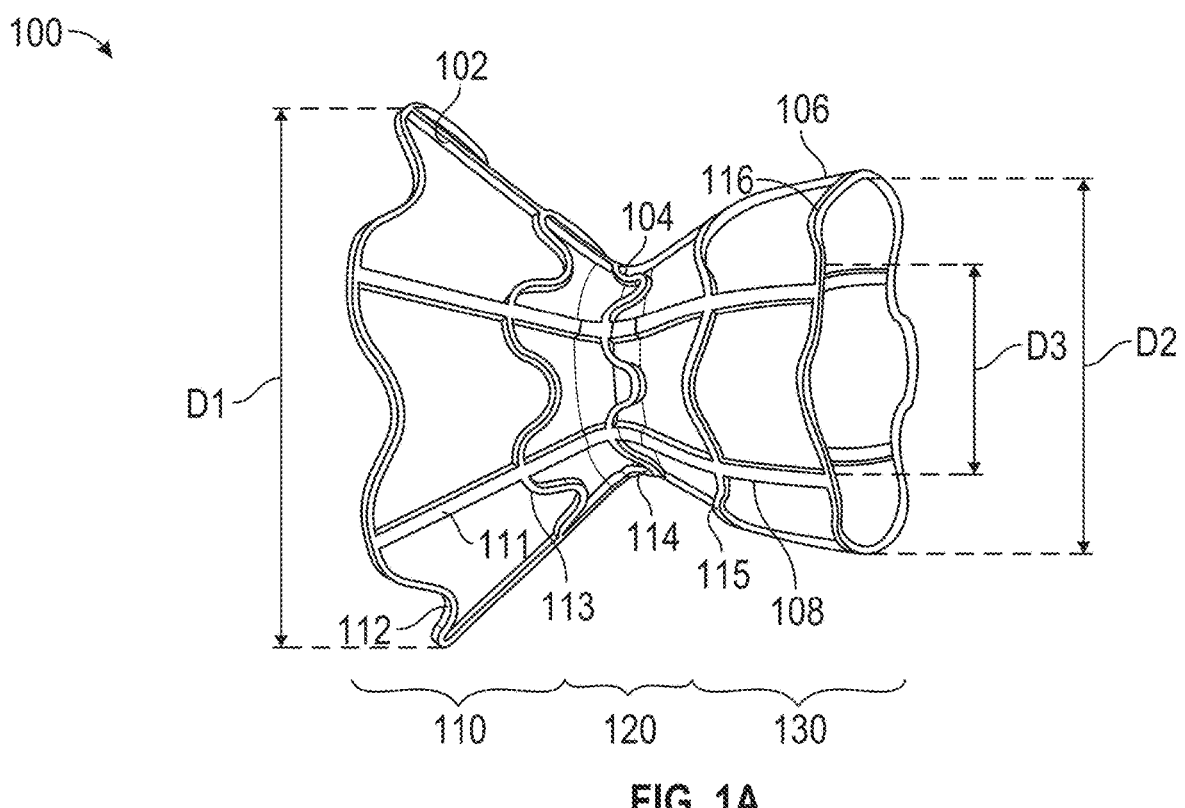
FIGS. 1A and 1B are a side views of an hourglass shaped shunt with and without a bridge constructed in accordance with the methods of the present invention.

Described herein are apparatus and methods for making and using improved interatrial shunts to improve treatment and outcomes for patients with cardiovascular and cardiopulmonary disorders, such as pulmonary artery hypertension (PAH) or heart failure (HF). In some aspects, the devices have dimensions that can be reduced and increased in vivo.

The present devices may be permanently or temporarily implantable in a human body and include one or more components which can be adjusted for size, larger or smaller, after implantation. The need for such adjustable devices may arise, for example, in the treatment of pulmonary artery hypertension (PAH) or heart failure (HF). In PAH, placing a shunt in the interatrial septum allows excessive blood pressure in the right atrium to be relieved by allowing some blood to flow from the right atrium to the left atrium through an orifice. In HF, placing a shunt in the interatrial septum allows excessive blood pressure in the left atrium to be relieved by allowing some blood to flow from the left atrium into the right atrium through an orifice. In both PAH and HF, interatrial shunting has been shown to effectively reduce symptoms and increase exercise tolerance. Interatrial shunting also may reduce the need for hospitalization and even improve life expectancy.

However, if the orifice of the interatrial shunt is too small, too little blood may be transferred and the shunt may be relatively ineffective and provide little or no clinical benefit. In contradistinction, shunting too much blood ("over-shunting") through too large of an orifice may lead to severe or even fatal complications over time. For example, in PAH patients, over-shunting may result in systemic oxygen desaturation and its sequalae including cyanosis, polycythemia with increased blood viscosity, end organ ischemia, and potentially death. In HF patients, over-shunting may result in pulmonary hypertension, right ventricular failure, and potentially death.

At present, there is no known way to predict the response of a given patient to a particular shunt orifice size. As is previously known, a shunt orifice may be increased in vivo, for example by dilating a suitably designed shunt by expanding an inflatable balloon catheter or other similar mechanically expansive means within the shunt, providing however, that the shunt is made from a malleable material and will remain expanded due to plastic deformation or some other physical property, whereby when the balloon or other expansive means is removed, the amount of elastic spring back or recoil will be low enough so that the desired increment in orifice size is achieved. One drawback of this approach is that the orifice size can only be increased. If the shunt starts out too large or is made too large by balloon dilatation but the patient needs a smaller shunt, there is no way to go back to a smaller size orifice except by providing another, smaller shunt or placing a smaller shunt within the lumen of original shunt. This technique is known as "shunt-in-shunt." As such, finding a suitable shunt orifice size for a given patient has been a trial and error process in which the shunt orifice size is selected according to the patient's response, which may be observed for a period of time which may be as short as a few minutes or as long as many months, and the shunt orifice size increased (e.g., by balloon dilatation) or reduced (by providing a new, smaller shunt) depending on the patient's response. As such, opportunities to increase or reduce the size of the shunt are very limited and may not be repeatable. Furthermore, the extent to which an inflatable balloon catheter can expand a shunt orifice may be limited by the maximum size of the balloon. Thus, what is needed is a means to repeatedly and non-traumatically adjust the orifice size of shunts, and other implantable devices, in vivo, and in both directions, bigger or smaller.

In some examples, the devices provided herein may incorporate technology with adjustable cross-sectional flow areas that may be easily reduced in vivo and/or expanded in vivo, in any order, as clinically necessary. Examples of interatrial shunts with adjustable cross-sectional flow areas are described in U.S. Pat. No. 9,724,499 to Rottenberg et al., U.S. Pat. No. 10,898,698 to Eigler et al., WO 2021/224736, and U.S. Patent App. Pub. No. 2021/0121179 to Ben-David et al., each assigned to the assignee of the present application, the entire contents of each of which are incorporated herein by reference. Some examples of the present devices include a self-expanding superelastic (austenitic phase) material as well as a malleable shape-memory (martensitic phase) material. When the device is implanted in the human body, e.g., by transporting the device in a compressed state within a sheath to a desired location and then removing the sheath, the self-expanding superelastic material may automatically deploy to its desired size, while the malleable shape-memory material initially may remain in a reduced size state. The cross sectional area of the malleable shape-memory material then may be expanded and reduced in vivo as desired so as to obtain a cross sectional area that is suitable for treating the patient, e.g., by providing a suitable fluid flow rate therethrough, or so as to appropriately fixate the device within the patient while allowing for repositioning to improve effectiveness of the treatment. A wide variety of devices may be prepared using components respectively including self-expanding superelastic materials and malleable shape-memory materials, such as exemplified herein.

One complication that can arise when adjusting the dimension of the shunt over time is tissue trauma to the atrial septum. The encapsulated shunt may be designed to promote tissue ingrowth and endothelialization and therefore expanding or reducing the encapsulated shunt after tissue has adhered to the encapsulated shunt over time can result in trauma to the atrial septum. Provided herein are devices for adjusting the dimensions of the shunt without disturbing the septal tissue surrounding the device. In particular, the device may include a bridge formed of biocompatible material that extends between the outer surfaces of first and second flared end regions, creating a gap between the bridge and a neck region of the encapsulated shunt. The bridge may be configured to engage the patient's atrial septum, rather than the encapsulated shunt itself such that, when the device is adjusted in vivo, the bridge may be configured to remain the same outer diameter while only the inner diameter of the shunt is modified. Accordingly, the bridge prevents dehiscence that may result when the device is adjusted in vivo. Further, the bridge may mitigate any bypass flow that may flow around the outside of the device after the diameter of the neck region is reduced in vivo.

The bridge described above could also be used with encapsulated shunts that are not adjustable in vivo. Patients who may benefit from an interatrial shunt also may have required or will require a prior transeptal procedure resulting in a hole in the septal wall. Alternatively, the patient may have septal defect that is predilated larger than the delivery system required to implant the device described here. Incorporating the bridge of biocompatible material to the encapsulated shunt increases the outer diameter of the device, thus permitting implantation of the device in the enlarged septal hole, without affecting the inner diameter of the device and fluid flow rate throughout the device.

In some examples, the present devices may be or include hourglass or "diabolo" shaped shunts, which optionally are encapsulated with biocompatible material, and which may be used for treating subjects suffering from disorders for which regulating fluid flow may be useful, such as CHF or PAH. In some examples, the hourglass shaped shunts may be specifically configured to be lodged securely in the atrial septum, for example in an opening through the fossa ovalis, to allow blood flow from the left atrium to the right when blood pressure in the left atrium exceeds that of the right atrium, or blood flow from the right atrium to the left when blood pressure in the right atrium exceeds that of the left atrium. As provided herein and described in greater detail in the above-incorporated PCT application WO 2021/224736, the internal dimension of the hourglass shaped shunt suitably may be adjusted in vivo, for example, so as to adjust the flow of fluid therethrough, e.g., so as to adjust the flow of fluid between the left atrium and the right atrium through the atrial septum.

Figure 1B:
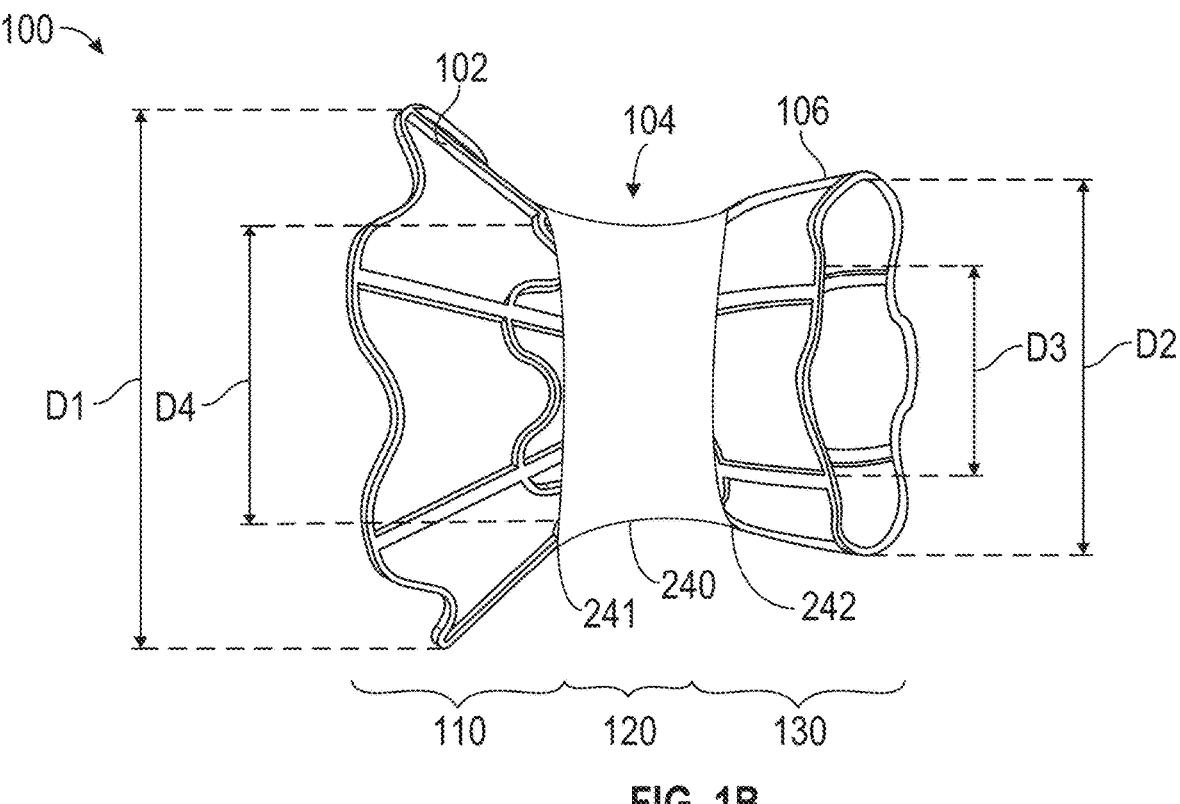
Figure 1D:
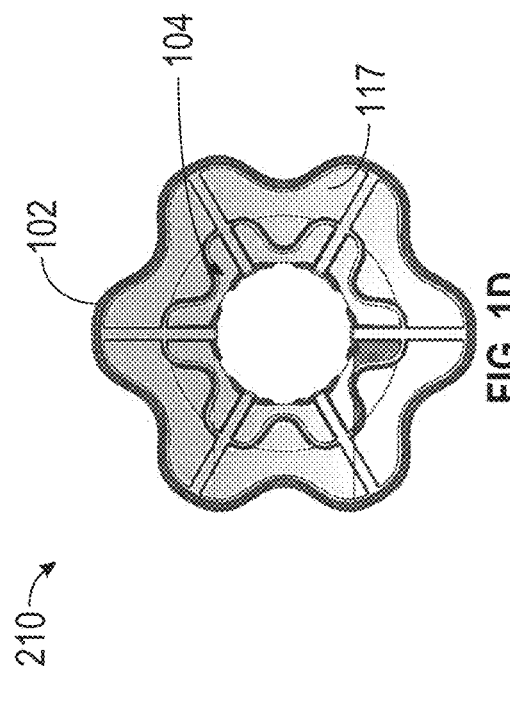
FIGS. 1C-1F are side, cross-sectional, and perspective views of the device of FIG. 1B.
Figure 1F:
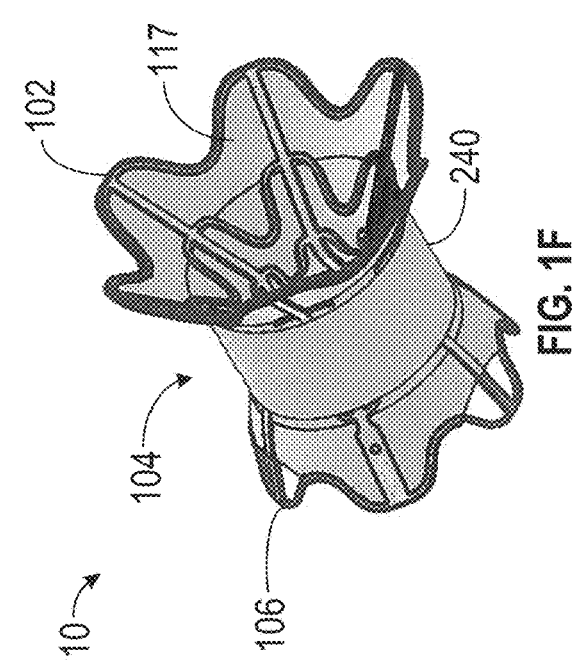

Referring now to FIGS. 1A and 1B, shunt 100 with and without a bridge is illustrated. Shunt 100 is hourglass or "diabolo" shaped and may include first component 110, second component 120, and third component 130, which are fluidically coupled to one another. In some embodiments, shunt 100 has an internal dimension that can be reduced and increased in vivo. First component 110 may include a first self-expanding superelastic material, second component 120 may include a malleable shape-memory material, and third component 130 may include a second self-expanding superelastic material. The malleable shape-memory material of second component 120 may have a first cross sectional area (or diameter) permitting a first rate of fluid flow through the second component, may be expandable to a second cross sectional area (or diameter) permitting a second rate of fluid flow through the second component, and may be contractible to a third cross sectional area (or diameter permitting a third rate of fluid flow through the second component. The overall rate of fluid flow through device 100 also may depend on the cross sectional areas (or diameters) of first component 110 and third component 130.

Shunt 100 may additionally or alternatively be constructed as described in U.S. Pat. Nos. 9,707,382, 9,980,815 and 10,639,459 to Nitzan et al., U.S. Pat. Nos. 10,076,403, 10,251,740 and 11,291,807 to Eigler et al., and U.S. Pat. No. 10,835,394 to Nae et al., each assigned to the assignee of the present application, the entire contents of each of which are incorporated herein by reference.

First component 110 may include any suitable number of rings, e.g., rings 112, 113, which are formed of or include the first self-expanding material, and which optionally may be sinusoidal. Second component 120 may include any suitable number of rings, e.g., ring 114, which is formed of or includes the malleable shape-memory material, and which optionally may be sinusoidal. Third component 130 may include any suitable number of rings, e.g., rings 115, 116, which are formed of or include the third self-expanding material, and which optionally may be sinusoidal. Struts 111, 108 may join the rings of first component 110, second component 120, and third component 130 to one another.

First component 110 may provide a first flared end region 102, third component 130 may provide a second end flared region 106, and second component 120 may provide a neck region 104 disposed between the first and second flared end regions. The inlet and outlet of device 100 may include flanges 102, 106, and the neck 104 may include flexible longitudinal struts 111, 108 and a sinusoidal ring 114. The flexible longitudinal struts 111, 108 may allow the flanges to fully expand upon deployment; and sinusoidal ring 114 may have sufficient strength to maintain its diameter when balloon dilated or heat contracted.

In the non-limiting example shown in FIG. 1A, first flared end region 102 has first end region dimension D1, second flared end region 106 has second end region dimension D2, and neck region 104 has neck dimension D3 which may be increased or reduced in a manner such as described with reference to second component 120 illustrated in FIGS.

3A-3D. As shown in FIG. 1A, neck region 104 of shunt 100 may be significantly narrower than flared end regions 102 and 106, e.g., may have a smaller cross sectional area and a smaller dimension than do flared end regions 102 and 106. Also shown in FIG. 1A, shunt 100 may be asymmetric. For example, shunt 100 may be asymmetric to take advantage of the natural features of the atrial septum of the heart as well as the left and right atrium cavities. Alternatively, hourglass shaped shunt 100 may be symmetric with the first end region dimension D1 being equal to the second end region dimension D2. First flared end region 102 and second flared end region 106 also may have either straight or curved profiles or both. For example, strut 111 has a straight profile and strut 108 has a curved profile. Additionally, first flared end region 102 and second flared end region 106 may assume any angular position consistent with the hour-glass configuration.

Device 100 optionally may be manufactured from a single tube of material that is laser-cut to define a plurality of struts and connecting members, e.g., a plurality of sinusoidal rings connected by longitudinally extending struts. The sinusoidal rings and longitudinal struts may be laser cut to form an integral piece of unitary construction, and different regions of the piece may be heat treated differently than one another to produce components having different austenitic finish temperatures (Afs) than one another in a manner such as described elsewhere herein. Alternatively, the sinusoidal rings of first component 110, second component 120, and third component 130 may be separately defined to form different pieces of material with suitable Afs that are subsequently coupled together to form device 100. Device 100 may also be electropolished to reduce thrombogenicity.

In some examples, the first self-expanding superelastic material of first component 110, the malleable shape-memory material of second component 120, and the second self-expanding superelastic material of third component 130 may include different materials than one another, or may include the same material as one another but having different phases than one another. For example, first component 110, second component 120, and third component 130 independently may include one or more materials selected from the group consisting of nickel titanium (NiTi), also known as NITINOL, other shape memory alloys, self-expanding materials, superelastic materials, polymers, and the like. In one non-limiting example, first component 110 and third component 130 each may include a NITINOL alloy having an austenitic finish temperature (Af) that is sufficiently below body temperature that the material is in an austenitic, superelastic phase while in the human body. In one non-limiting example, the self-expanding superelastic material of first component 110 and third component 130 includes NITINOL having an Af of less than 37° C. For example, the Af of the NITINOL of the self-expanding superelastic material may be between 5-20° C. First component 110, second component 120, and third component 130 optionally may be integrally formed from a common frame with one another. For example, first component 110, second component 120, and third component 130 may be initially cut and processed as a single unit from the same tubing, sheet, or other suitable configuration of frame as one another. Portions of that common frame may be heat treated differently than one another so as to define first component 110, second component 120, and third component 130, e.g., in a manner similar to that described in the above-incorporated PCT application WO 2021/224736.

Second component 120 may include a NITINOL alloy having an austenitic phase transition temperature Af that is slightly above body temperature such that the material remains in its martensitic, malleable shape-memory phase while in the body unless and until it is heated to its Af, for example by the injection of warm or hot saline (or other fluid) into the fluid within or flowing through second component 120, or by applying heat through electrical energy such as with an RF energy source. In one non-limiting example, the malleable shape-memory material of second component 120 includes NITINOL having an austenitic finish temperature (At) of greater than 37° C. For example, the Af of the NITINOL of the malleable shape-memory material of second component 120 may be between 45-65° C., e.g., from 50-55° C. In some examples, the warm or hot saline (or other fluid) may be injected sufficiently close to second component 120 to heat that component to or above its Af, using a side-hole catheter positioned through device 100. Optionally, an expandable balloon may be disposed on the distal end of the side-hole catheter and inflated at the distal opening of the shunt such that blood flow within the shunt is blocked during delivery of the saline. In a similar example, an expandable balloon may be disposed proximal to the distal end of the side-hole catheter and inflated at the proximal opening of the shunt, again such that blood flow within the shunt is blocked during delivery of the saline. In yet another example, the warm or hot saline may be injected through a distal end of a central lumen of a catheter that is positioned adjacent to or proximal to second component 120. Preferably, the distal end of the catheter comprises a larger hole than the side holes described above, such that heated saline may be delivered more rapidly. Optionally, a separate balloon catheter may be inserted through device 100 such that the balloon is distal to the catheter for delivering saline. Before injecting the saline through the distal end of the catheter, the balloon may be expanded at the distal opening of device 100 to block blood flow during delivery of saline, which may increase the effectiveness of the heating. Use of separate catheters for delivering saline and blocking blood flow may permit the saline to heat the stent more quickly while the expanded balloon is kept in place.

In other examples, a pair of electrodes may be brought into contact with device 100, e.g., via a catheter, and actuated at an appropriate voltage and frequency to heat component 120 to or above its Af. In still other examples, any other suitable means of locally applying heat to device 100, such as a laser, magnetic inductance, electrical resistance, or the like, may be used. Heating device 100 using electrical resistance may include contacting the device with a pair of electrodes, e.g., via a catheter, and passing a current through the device that causes heating of the device. Heating device 100 using a laser may include irradiating the device with light from a laser that may be introduced by a catheter. Heating device 100 using magnetic inductance may include passing an alternating magnetic field through the device that induces eddy currents inside the device which heat the device. Note that in blood vessels having a particularly high rate of blood flow (e.g., 2-5 L/min), such as the aorta or internal iliac artery, it may be useful to heat device 100 using direct heating methods, such as using electrical energy (e.g., direct current (DC), radio frequency (RF)), a laser, magnetic inductance, electrical resistance, non-contact radiofrequency (RF), dielectric heating, or conductive heating such as local probe heating, instead of saline, before sufficiently heating the device.

Alternatively, device 100 may include a single NITINOL alloy that has been heat treated to produce a lower Af in regions respectively corresponding to first component 110 and third component 130, and that has been heat treated to produce a higher Af in a region corresponding to second component 120. The malleable shape-memory material of second component 120 may be expandable and contractible using any suitable technique. For example, the malleable shape-memory material of second component 120 may be mechanically expanded, e.g., using balloon dilatation such as known in the art. Additionally, or alternatively, malleable shape-memory material of second component 120 may be thermally contracted, e.g., using saline at a temperature at or above the Af of that material, or otherwise heated such as with RF energy or the use of a laser, magnetic inductance, electrical resistance, or the like in a manner such as described above.

The first, second, and third components may be coupled, e.g., fluidically coupled, to one another using any suitable manner(s) of joining. For example, any malleable shape-memory material optionally and independently may be joined to any self-expanding superelastic material by welding. Additionally, or alternatively, any malleable shape-memory material optionally and independently may be joined to any self-expanding superelastic material using an encapsulant which may cover at least a portion of at least one of the components, and which may join such components to one another. Additionally, or alternatively, any shape-memory material and any self-expanding superelastic material may be integrally formed from a common frame with one another.

Encapsulants may include any suitable biocompatible material, such as a polymer or a natural material. Examples of polymers suitable for use as an encapsulant include expanded polytetrafluoroethylene (ePTFE), silicone, polycarbonate urethane, DACRON (polyethylene terephthalate), Ultra High Molecular Weight Polyethylene (UHMWPE), and polyurethane. Examples of natural materials suitable for use as an encapsulant include pericardial tissue, e.g., from an equine, bovine, or porcine source, or human tissue such as human placenta or other human tissues. The biocompatible material is preferably smooth so as to inhibit thrombus formation, and optionally may be impregnated with carbon so as to promote tissue ingrowth. Alternatively, to promote tissue ingrowth and endothelization, the biocompatible material may form a mesh-like structure. The present devices may be encapsulated with a biocompatible material in a manner similar to that described in U.S. Pat. No. 11,304,831 to Nae et al., entitled "Systems and Methods for Making Encapsulated Hourglass Shaped Stents," the entire contents of which are incorporated by reference herein. Additional methods for encapsulating the shunt are described in U.S. Pat. No. 10,835,394 to Nae et al., U.S. Pat. No. 11,109,988 to Rosen et al., U.S. Pat. No. 9,034,034 to Nitzan et al., U.S. Pat. No. 9,980,815 to Nitzan et al., and U.S. Pat. No. 10,076,403 to Eigler, the entire contents of each of which are incorporated by reference herein.

In one example, the device is encapsulated with ePTFE. It will be understood by those skilled in the art that ePTFE materials have a characteristic microstructure consisting of nodes and fibrils, with the fibrils orientation being substantially parallel to the axis of longitudinal expansion. Expanded polytetrafluoroethylene materials may be made by ram extruding a compressed billet of particulate polytetrafluoroethylene and extrusion lubricant through an extrusion die to form sheet or tubular extrudates. The extrudate is then longitudinally expanded to form the node-fibril microstructure and heated to a temperature at or above the crystalline melt point of polytetrafluoroethylene, i.e., 327° C., for a period of time sufficient to sinter the ePTFE material. Heating may take place in a vacuum chamber to prevent or inhibit oxidation of the device. Alternatively, heating may take place in a nitrogen rich environment. A furnace may be used to heat the encapsulated device. Alternatively, or additionally, a mandrel upon which the encapsulated device rests may be used to heat the encapsulated device.

Referring now to FIG. 1B, the device shown in FIG. 1A is modified to add a bridge at neck region 104, which is configured to engage a patient's atrial septum. Device 100 is preferably encapsulated with graft material to create a shunt-graft assembly and a passageway to permit blood to flow; this graft material has been omitted from FIG. 1B to better illustrate the location of bridge 240. Bridge 240 may be made of a biocompatible material, such as a polymer or a natural material as described above, and may be the same material as the material used to encapsulate the frame or may be a different material. Preferably, the biocompatible material of the bridge is one that encourages tissue adherence such that contact with the septal wall is maintained if the inner diameter of the shunt is decreased. Maintaining contact with the septal wall helps prevent any fluid bypass around the outside of the device. The biocompatible material may be configured to promote tissue ingrowth over the entire bridge or over only a portion of the bridge. For example, holes may be placed at the location of bridge 240 that is configured to engage the atrial septum while the remainder of bridge 240 remains whole such that tissue ingrowth is not encouraged on the flared end regions. This configuration may be beneficial for the embodiment shown in FIGS. 12A-12D, wherein the biocompatible material of bridge 240 extends up the flared end regions and along the interior of the encapsulated shunt.

In addition, or alternatively, bridge 240 may be made of a different biocompatible material than the biocompatible material used to encapsulate the shunt. For example, the shunt may be encapsulated with a biocompatible material, such as ePTFE, having a sufficiently small pore size such that tissue ingrowth is mitigated and the bridge may be made of a biocompatible material having a larger pore size that is designed to encourage tissue ingrowth. Generally, the larger the pore size of the biocompatible material, the greater the adherence of tissue to the biocompatible material. In addition to encouraging tissue ingrowth, greater porosity permits the exchange of fluids in and out of the gap between the outer surface of neck region 104 and bridge 240. For example, bridge 240 may be made of ePTFE that has a larger intermodal distance (e.g., approximately 60-200 μm) than the ePTFE that encapsulates the shunt.

Alternatively, bridge 240 may be made of woven Dacron to further encourage tissue ingrowth. The Dacron may be securely attached to the encapsulated shunt using stitches rather than the method described below. Because Dacron is bulkier than ePTFE, the cross-section of the device in the collapsed or crimped configuration may be increased, which may mean that a larger diameter sheath may be required for delivery of the device. Additional materials that may be used to promote tissue ingrowth include using a mesh-like structure, electrospun fabrics, or silicone.

Bridge 240 may have first end 241 and second end 242 and may be shaped and sized such that first end 241 is disposed approximately half way up first flared end region 102 and second end 242 is disposed approximately half way up second flared end region 106. Alternatively, first end 241 and second end 242 may extend further up first flared end region 102 and second flared end region 106 or may be attached nearer neck region 104. Bridge 240 may be stretched such that a gap is created between the outer surface of neck region 104 and the inner surface of bridge 240. The gap may be widest at the narrowest point of the outer surface of neck region 104.

As described above, the encapsulated shunt may be adjusted in vivo to increase or decrease the neck dimension and thereby adjust the fluid flow rate through the shunt. Because the encapsulated shunt may be designed to promote tissue ingrowth and endothelialization, tissue may adhere to the shunt over time. Adjustments of the encapsulated shunt to increase or decrease the dimensions can therefore result in trauma to the atrial septum. Bridge 240 is designed to prevent dehiscence and to mitigate the tissue trauma that can result from such adjustments. Bridge 240 is configured to engage with the atrial septum and defines outer diameter D4. Preferably, outer diameter D4 is larger than neck dimension D3. In one embodiment, outer diameter D4 may be 7-9 mm and neck dimension D3 may be 4.5-5.5 mm. When the device is adjusted in vivo, bridge 240 may be configured to remain the same outer diameter D4 while only the neck dimension D3 of the shunt and the size of the gap is modified. Due to the creation of a gap between neck region 104 and bridge 240, neck dimension D3 may be decreased or increased up to outer diameter D4 causing an increase or decrease in the size of the gap, without disturbing the septal tissue contacting and surrounding bridge 240 and while maintaining contact with the septal tissue such that leakage or bypass flow around the outer surface of the shunt is minimized.

Bridge 240 could also be used with encapsulated shunts that are not adjustable in vivo. In particular, incorporating bridge 240 into an encapsulated shunt may be beneficial for patients who have an enlarged hole prior to implantation of the device, for example, from a prior transseptal procedure, or have a septal defect that is predilated larger than the delivery system required to implant the device described herein. For example, for a patient with severe mitral regurgitation and poor left ventricular function, it may be clinically desirable to first perform a repair procedure on the mitral valve, e.g. MitraClip® of mitral annuloplasty by the percutaneous transseptal approach, followed by interatrial shunt placement. These mitral valve procedures currently use a 23 Fr I.D. (~8 mm outer diameter) guiding catheter to cross the foramen ovalis. After mitral repair, a shunt with an outer minimal diameter matching the larger aperture defect caused by the prior procedure may be implanted, wherein the conduit as a smaller diameter desirable for shunting (e.g. 5.0 to 6.5 mm). Likewise, such shunts advantageously may be used where, during the transseptal procedure, the fossa ovalis has been torn, thus creating a larger aperture defect than required for the embodiment shown in FIG. 1A.

Incorporating the bridge of biocompatible material to the encapsulated shunt increases the outer diameter of the device, thus permitting implantation of the device in the enlarged septal hole, without affecting the inner diameter and fluid flow rate throughout the device. Further, bridge 240 permits the inner diameter of the encapsulated shunt to be temporarily increased, for example, during a separate transseptal procedure after implantation of the device, without disturbing the outer diameter of the neck region, thus minimizing the risk of tears to the septal tissue.

Figure 1C:
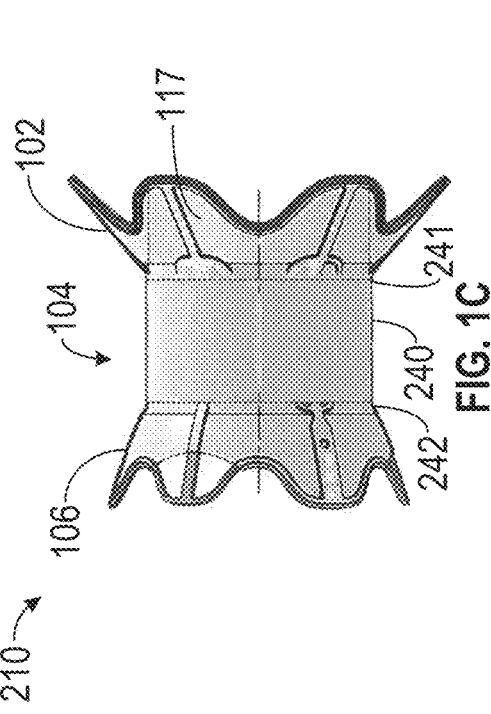
Figure 1E:
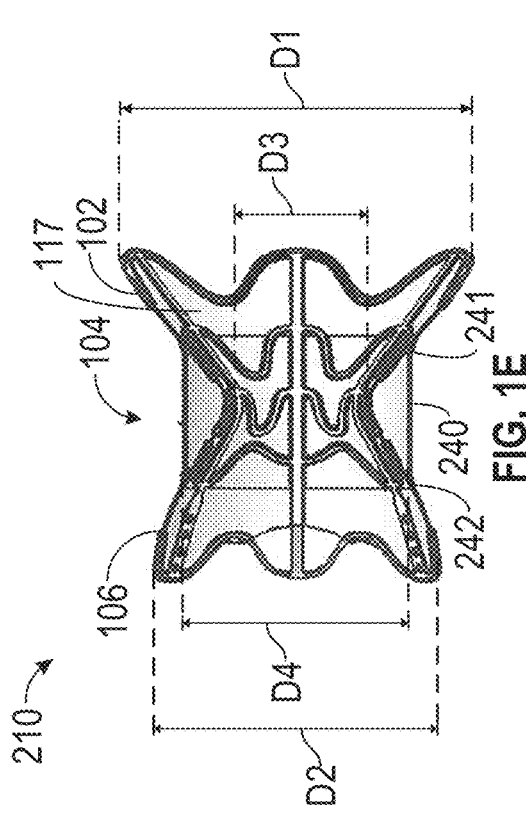

Referring now to FIGS. 1C, 1D, 1E, and 1F, additional side, front, side cross-sectional, and perspective views are shown, respectively. FIG. 1C shows shunt 100 encapsulated with biocompatible material 117 to create shunt-graft assembly 210 and to define a flow path through shunt-graft assembly 210. As shown in FIG. 1E, neck region 104 defines the inner diameter, neck dimension D3, of the passageway through which blood flows. Bridge 240 surrounds the entire neck region 104 to define outer diameter D4.

Figure 2A:
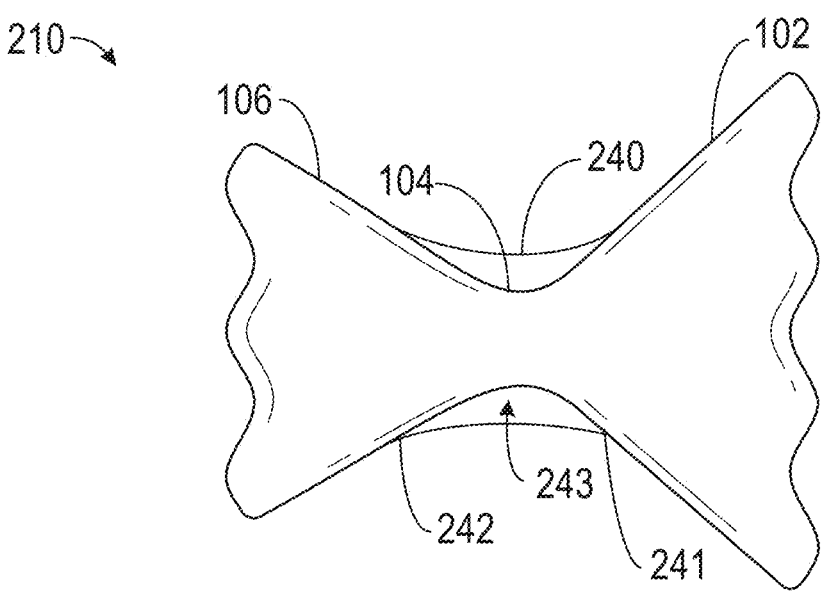
FIGS. 2A and 2B are cross-sectional side views of the device of FIG. 1B.
Figure 2B:
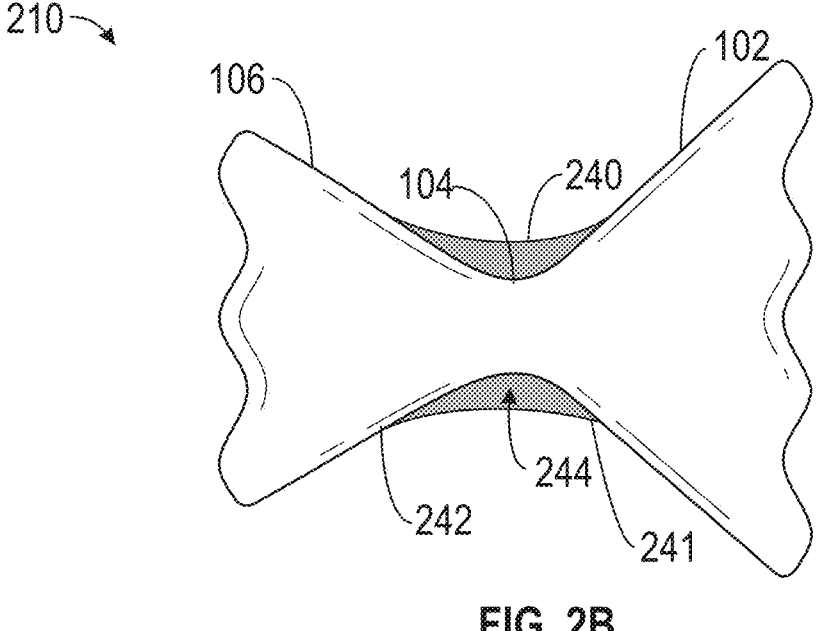

Referring now to FIGS. 2A and 2B, cross-sectional side views of the device of FIG. 1B showing an unfilled and a filled gap between the bridge and the encapsulated shunt. Bridge 240 is attached at first end 241 to first flared end region 102 and is attached at second end 242 at second flared end region 106. Exemplary methods of attaching bridge 240 to the encapsulated shunt is described further below with respect to FIGS. 11A-11D and 12A-12D. Preferably, bridge 240 is stretched such that a gap is created between neck region 104 and bridge 240. Gap 243 may be filled with a flexible biocompatible material or a liquid biocompatible material, such as a hydrogel. Alternatively, gap 243 may be filled with bodily fluids upon delivery and implantation of shunt-graft 210. This embodiment is advantageous where the dimensions of the shunt are configured to be adjusted in vivo. Specifically, gap 243 may be increased or decreased during such adjustments while the outer diameter of the neck region that contacts the atrial septum (e.g., the bridge) remains the same, thus minimizing any tissue trauma. For example, bridge 240 may be made of ePTFE having holes such that when shunt-graft assembly 210 expands, the biocompatible material disposed within gap 243 is configured to permeate through bridge 240.

As shown in FIG. 2B, the gap between bridge 240 and the encapsulated shunt may be filled with a biocompatible material, such as a polymer or a natural material that is not flexible such that the gap remains the same size even if the dimensions of shunt-graft assembly 210 are adjusted. This embodiment may be beneficial where the device is designed to be implanted into an enlarged septal hole and the device is not configured to be adjusted in vivo. In particular, because the inner diameter of the device may not be adjusted, the dimensions of gap 244 do not need to be adjustable. Accordingly, gap 244 may be filled with a solid material or a low durometer material such as a hydrogel, which may increase the stability of the device and make the bridge more robust.

Figure 3A:
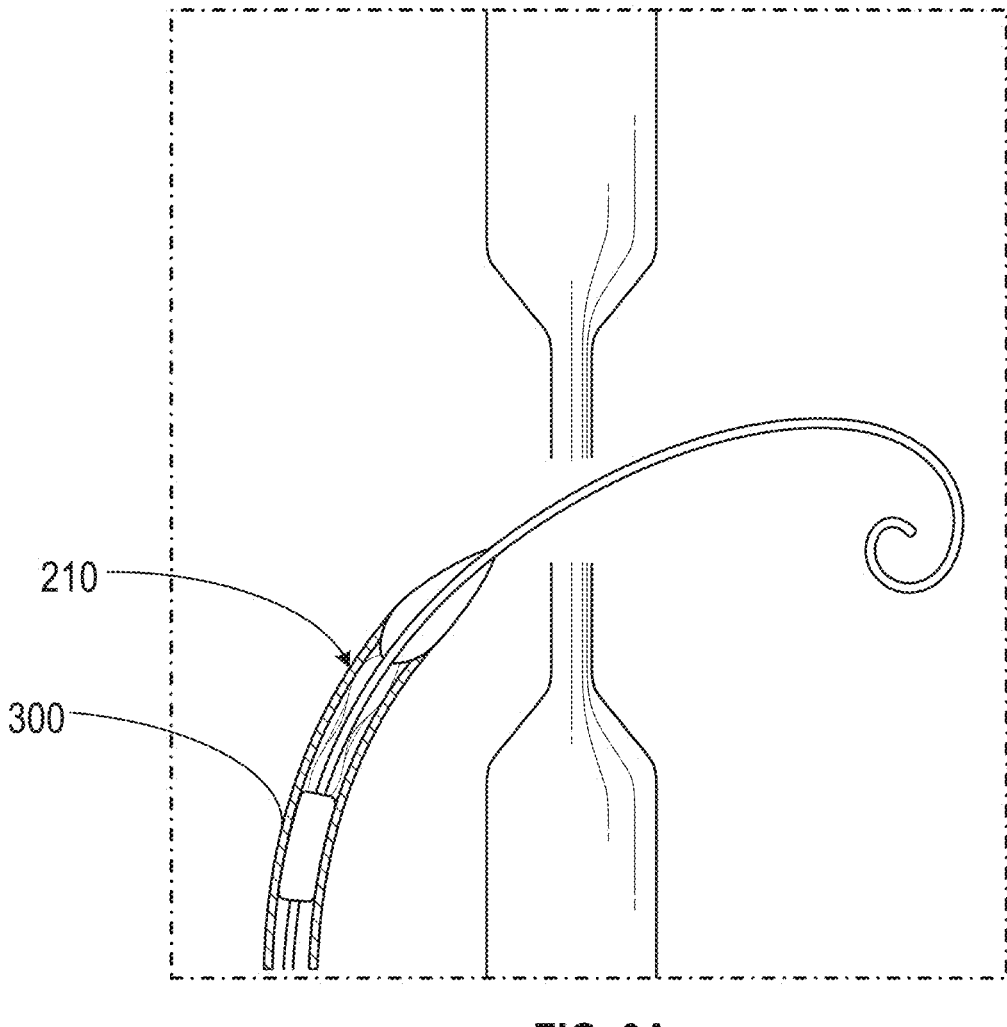
FIGS. 3A-3E illustrate example steps for using the device of FIG. 1B in the human body.
Figures 3B, 3C:
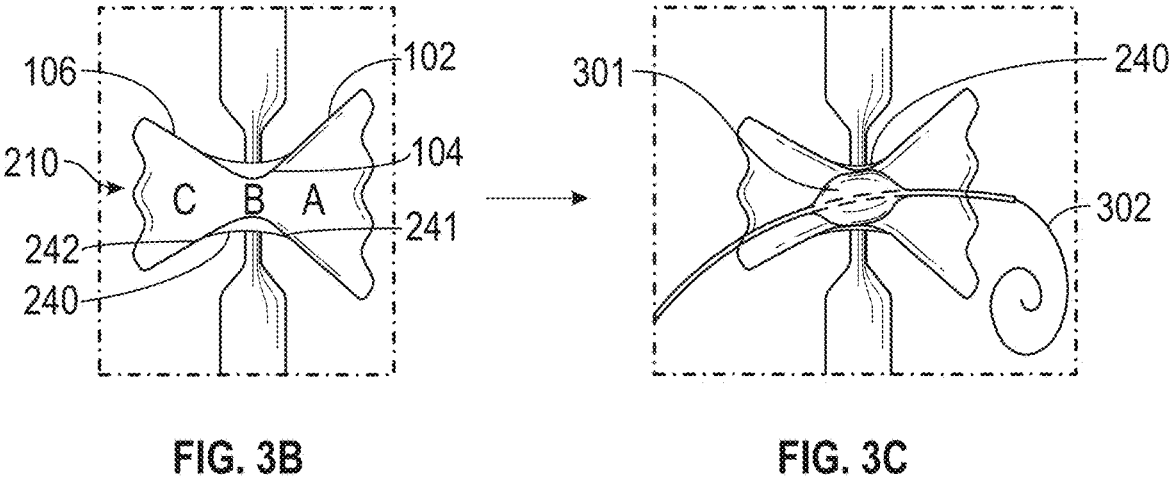

FIGS. 3A-3E schematically illustrate example steps for using the device of FIG. 1B in the human body. Shunt-graft assembly 210 may be crimped to a cylindrical shape, for example by pushing it through a conical loading device. In one non-limiting example, shunt-graft assembly 210 may be crimped to an outer dimension of about 4.6 mm, the inside dimension of a 14F Cook sheath. For example, FIG. 3A illustrates shunt-graft assembly 210 disposed within sheath 300. As will be understood by one of skill in the art, shunt-graft assembly 210 may be crimped to a smaller or larger outer dimension if a different size Cook sheath is used. In addition, a layer of hydrogel may be placed with gap 244 between bridge 240 and shunt-graft assembly 210, which may affect the crimped dimension. The delivery catheter and sheath 300 may be designed as described in U.S. Pat. No. 9,713,696 to Yacoby et al. and U.S. Patent Publication No. 2020/0315599 to Nae et al., entitled "Systems and Methods for Delivering Implantable Devices across an Atrial Septum," each assigned to the assignee of the present application, the entire contents of each of which are incorporated by reference herein. The sheath may be percutaneously placed through a blood vessel to a desired location in the human body. As the crimped shunt is pushed out of sheath 300, the self-expanding superelastic flared end regions spring open to their set configuration, while the malleable shape-memory central neck region remains constrained at or near its crimped dimension, e.g., in a manner such as illustrated in FIG. 3B in which bridge 240, disposed over neck region 104 (designated "B" and corresponding to second component 120), engages an opening in the human body. Depending on the desired direction of blood flow through shunt-graft assembly 210, first flared end region 102 and second flared end region 106 (designated "A" or "C" and corresponding to first component 110 or third component 130) provides an inlet and the other of the flared ends (designated "C" or "A" and corresponding to third component 130 or first component 110) provides an outlet. For example, bridge 240 may engage an opening created through a fossa ovalis of an interatrial septum between a right atrium and a left atrium, one of the flared ends extends into the right atrium, and the other flared end extends into the left atrium. In some configurations, the flared end in the right atrium is an inlet and the flared end in the left atrium is an outlet, whereas in other configurations, the flared end in the left atrium is an inlet and the flared end in the right atrium is an outlet. As used herein, "inlet" means component with ingress of blood flow, and "outlet" means component with outgress (egress) of blood flow. The particular components that respectively may be used to provide ingress and outgress (egress) of blood flow may be selected based on the condition being treated. For example, in HF, the inlet may be on the left atrial (LA) side, where blood flow from LA to right atrium (RA), and LA decompression, are desirable. In contradistinction, in PAH, the interatrial pressure gradient is reversed causing R to L flow and RA decompression, and the inlet is on the RA side.

The cross sectional area (and dimension) of the orifice provided by the malleable shape-memory central neck region may be increased or reduced so as to adjust the flow of fluid through shunt-graft assembly 210. For example, in a manner such as illustrated in FIG. 3C, the neck region may be expanded by balloon dilatation using balloon 301 (e.g., a 12 mm diameter balloon), which may be fed through the orifice using a wire 302. Preferably, balloon 301 expands the neck region only to a threshold outer diameter, defined by bridge 240, such that expansion of the neck region does not affect the outer diameter of the device or disturb the septal tissue surrounding bridge 240. For example, bridge 240 may be sized and shaped to define an outer diameter of 7-14 mm and balloon 301 may be configured to expand the neck region up to 9 mm.

Figures 3D, 3E:
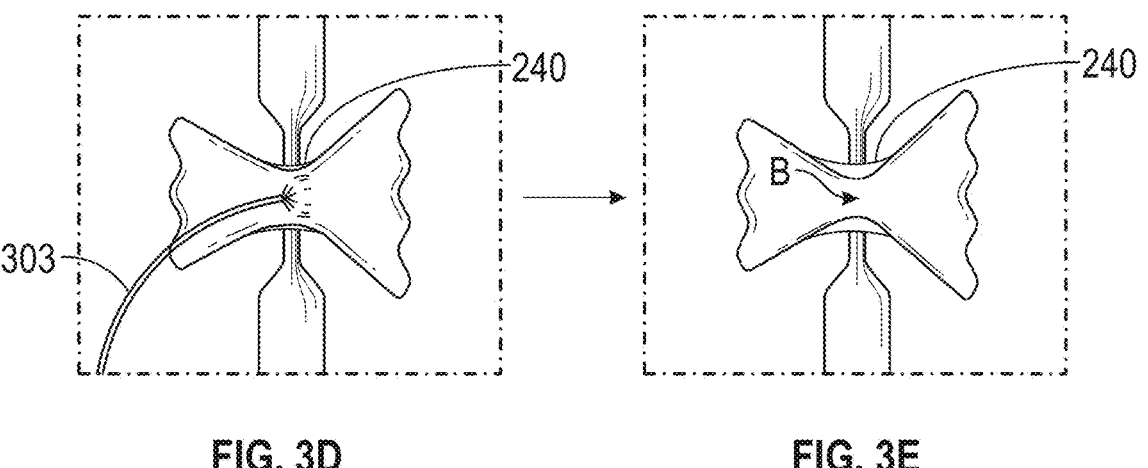

Additionally, in a manner such as illustrated in FIG. 3D and as described above, the neck region may be contracted by injecting, via a distal end of catheter 303, a bolus of hot saline having a temperature above the Af of the malleable shape-memory material (e.g., at 45-65° C.), which may cause the neck region to return to its heat-set dimension, which may be different from its crimped dimension and preferably is 4.5-5.5 mm. FIG. 3D illustrates one method of heating the neck region, but other methods may be used. For example, the saline may be injected via side-holes in catheter 303. Further, a second balloon catheter may be inserted through shunt-graft assembly 210 such that the balloon is distal to the location the saline is delivered and the balloon may be expanded to block blood flow through shunt-graft assembly 210 during delivery of the saline. In other examples, a pair of electrodes may be positioned to contact shunt-graft assembly, e.g., via catheter 303, and actuated at an appropriate voltage and frequency to heat the neck region to or above its Af. In still other examples, other suitable means of locally applying heat to device 100, such as a laser, magnetic inductance, electrical resistance, or the like, may be used. Preferably, the return of the neck region to its heat-set dimension does not affect the outer diameter of bridge 240, as illustrated in FIG. 3E.

For example, heat from the saline may cause the malleable shape-memory material to transition to an austenitic phase, contracting the neck region back to its crimped (or otherwise heat set) dimension, following which the neck region cools to body temperature and transitions back to its martensitic phase. The saline may be delivered in any suitable manner, for example by a flexible catheter having one or more apertures (e.g., one end hole, one side hole, or multiple side-holes) through which hot saline may flow and that may be placed within the neck region, for example, over a guidewire through the neck region. In one non-limiting example, the neck region may have its crimped inner dimension, typically 1-2 mm, at a first time, such as when initially deployed in a manner such as illustrated in FIG. 3B. The neck region then may be expanded using balloon dilatation to any desired larger dimension between the crimped dimension and the outer diameter of bridge 240 at a second time. The neck region then may be contracted using hot saline to its heat-set dimension at a third time. The heat-set dimension is determined by the size of the jig used in a heat-setting step during manufacture and may be approximately the same as, may be smaller than, or may be larger than the dimension of the neck region in the crimped state. The heat-set dimension may be greater than the dimension of the catheter used to deliver hot saline, and greater than the deflated dimension of the dilation balloon, but smaller than or equal to the smallest anticipated desired final shunt dimension, for example 4 mm. The neck region then again may be expanded using balloon dilatation to any desired larger dimension between 4 mm and the outer diameter of bridge 240 at a second time. Any suitable number of expansions and contractions may be applied to the neck region, at any desired time or at separate times than one another, so as to provide a suitable, and customized, flow of fluid through the device for each given patient.

It will be appreciated that what constitutes a suitable flow of fluid for a given patient also may change over time, and that the present devices suitably may be adjusted so as to provide that flow of fluid as appropriate, or so as to suitably fixate the devices within a lumen. It will also be appreciated that the self-expanding superelastic components are not affected by the injection of hot saline, and so will retain their initial full expanded dimension while the shape-memory component (in this example the neck region) is being adjusted. Furthermore, any suitable method for heating the shape memory materials may be used besides or in addition to hot saline, e.g., RF heating or the use of a laser, magnetic inductance, electrical resistance, or the like in a manner such as described with reference to FIG. 1A.

Figure 4B:
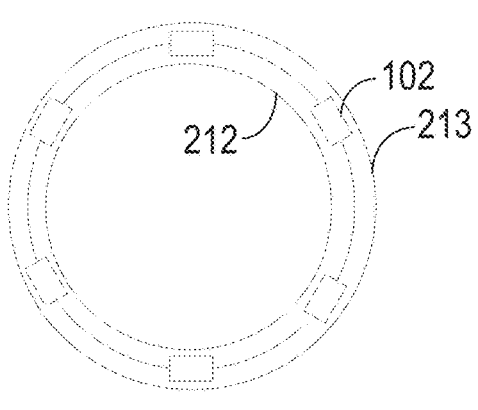
FIGS. 4A-4D illustrate the structure of a shunt-graft assembly having two and three layer regions.
Figure 4A:
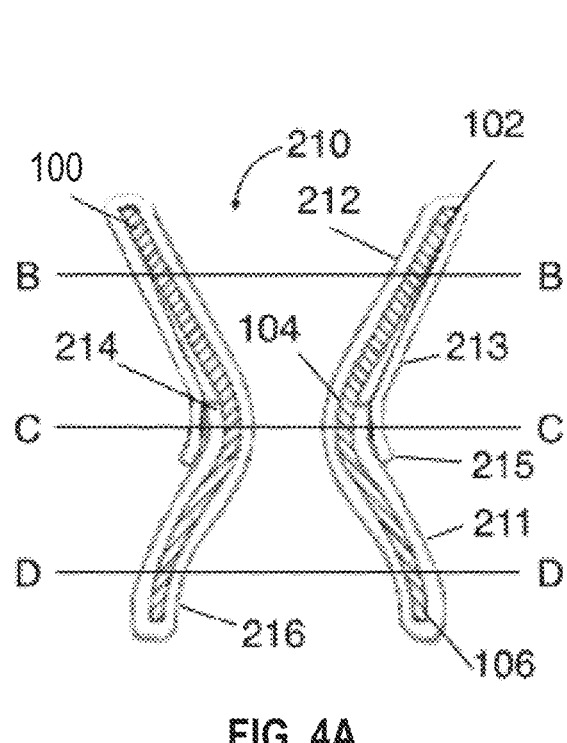

Referring now to FIGS. 4A-D, a method of encapsulating the shunt in a biocompatible material is described, and is further described in U.S. Pat. No. 11,304,831. Preferably, shunt 100 is at least partially covered with biocompatible material to create shunt-graft assembly 210. For example, shunt 100 may be covered with a single tube of biocompatible material, as shown in FIG. 4A, to create shunt-graft assembly 210 having varying layers of biocompatible material (e.g., two-to-three layers of biocompatible material). Graft tube 216, which is a tube of biocompatible material, has first graft portion 211, second graft portion 212, and third graft portion 213. Graft tube 216 has a length that is longer that the length of shunt 100 and preferably greater than twice the length of shunt 100. First graft portion 211 begins at first end 214 of graft tube 216 and extends to second graft portion 212. Second graft portion 212 extends between first graft portion 211 and third graft portion 213 and is continuously joined to first graft portion 211 and third graft portion 213. Third graft portion 213 ends at second end 215 of graft tube 216. FIGS. 5A-10B illustrate an exemplary approach for depositing graft tube 216 on shunt 100 in the configuration shown in FIGS. 4A-D.

Figure 4C:
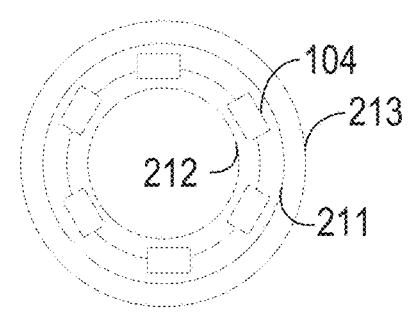
Figure 4D:
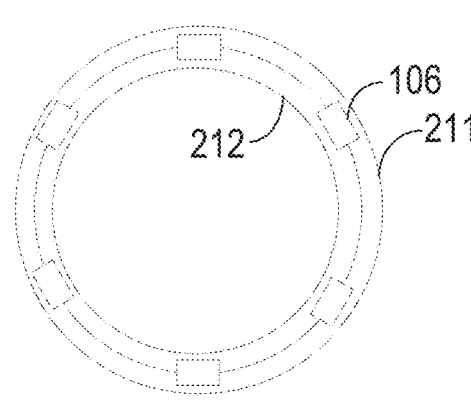

The cross sections of shunt-graft assembly 210 illustrated in FIG. 4A (cross-sections B, C, and D) are illustrated in FIGS. 4B, 4C, and 4D, respectively. The thickness of the graft material is increased in the cross-sectional views in order to better illustrate the different layers of graft material over shunt 100. As will be understood by one of skill in the art, the different cross-sections of the flared end regions and the neck region may be greater than or less than the cross-sections shown in FIGS. 4B-4D. Preferably, each graft layer is less than the thickness of shunt 100 such that encapsulating shunt 100 only minimally increases the dimensions of the flared end regions and the neck region. Referring now to FIG. 4B, cross-section B of shunt-graft assembly 210 is illustrated. As is shown in FIG. 4B, first flared end region 102 of shunt 100 may be covered on the outer surface and the inner surface by graft tube 216. Specifically, first flared end region 102 may be covered on the outer surface by third graft portion 213 and on the inner surface (i.e., on the interior of first flared end region 102) by second graft portion 212. Accordingly, shunt 100 may be covered at first flared end region 102 by two layers of biocompatible material.

Referring now to FIG. 4C, cross-section C of shunt-graft assembly 210 is illustrated. As is shown in FIG. 4C, neck region 104 of shunt 100 may be covered by two layers of biocompatible material on the outer surface and one layer of biocompatible material on the inner surface of neck region 104. Specifically, neck region 104 may be first covered on the outer surface by first graft portion 211, which is covered by third graft portion 213. On the inner surface (i.e., on the interior of neck region 104), shunt 100 may be covered by second graft portion 212. Accordingly, shunt 100 of the shunt-graft assembly 210 may be covered at neck region 104 by three layers of biocompatible material.

Referring now to FIG. 4D, cross-section D of shunt-graft assembly 210 is illustrated. As is shown in FIG. 4D, second flared end region 106 of shunt 100 is covered on the outer surface and the inner surface by graft tube 216. Specifically, second flared end region 106 may be covered on the outer surface by first graft portion 211 and on the inner surface (i.e., on the interior of second flared end region 106) by second graft portion 212. Accordingly, shunt 100 of shunt-graft assembly 210 may be covered at second flared end region 106 by two layers of biocompatible material.

The layers of biocompatible material may be securely bonded together to form a monolithic layer of biocompatible material. For example, first graft portion 211, second graft portion 212, and third graft portion 213 may be sintered together to form a strong, smooth, substantially continuous coating that covers the inner and outer surfaces of the stent. Portions of the coating may then be removed as desired from selected portions of the stent using laser-cutting or mechanical cutting, for example.

FIGS. 5A-10D generally illustrate an exemplary method of making shunt-graft assembly 210, as depicted in FIGS. 4A-4D. Referring now to FIG. 5A, to deposit the first graft portion upon the neck region and the second flared end region, the process may start by crimping shunt 100. For example, shunt 100 may be placed within funnel 207 and advanced within funnel 207 towards a reduced section of funnel 207. The reduced section preferably is the diameter of the neck region of the stent or slightly larger. However, it is understood that shunt 100 may be reduced to different diameters. Shunt 100 may be advanced by a dedicated pusher tool like the one described in U.S. Pat. No. 9,713,696 to Yacoby. Shunt 100 may be constructed in a manner that, upon reduction caused by funnel 207, the shape of shunt 100 morphs such that the first and second flared end regions are tapered and eventually turned inward toward a longitudinal axis of shunt 100, resulting in shunt 100 having a substantially reduced cross-sectional diameter. It is understood that shunt 100 may alternatively be compressed into a compressed state using any well-known compressing or crimping techniques.

As is shown in FIGS. 5B and 5C, funnel 207 may have or may be coupled to introducer tube 208 extending from the narrow side of the funnel 207 which may receive shunt 100 after shunt 100 has been fully restricted by funnel 207. Introducer tube 208 may have a diameter smaller than that of the graft tube. Alternatively, the first end of the graft tube may be expanded to a diameter larger than that of introducer tube 208 using well-known expansion techniques (e.g., applying heat to the graft tube). Introducer tube 208 may thus be inserted into first end 214 of graft tube 216, as is illustrated in FIG. 5C, and shunt 100 having the reduced diameter, may be partially advanced out of introducer tube 208 and into graft tube 216, such that second flared end region 106 and neck region 104 are advanced into graft tube 216.

Figure 5D:
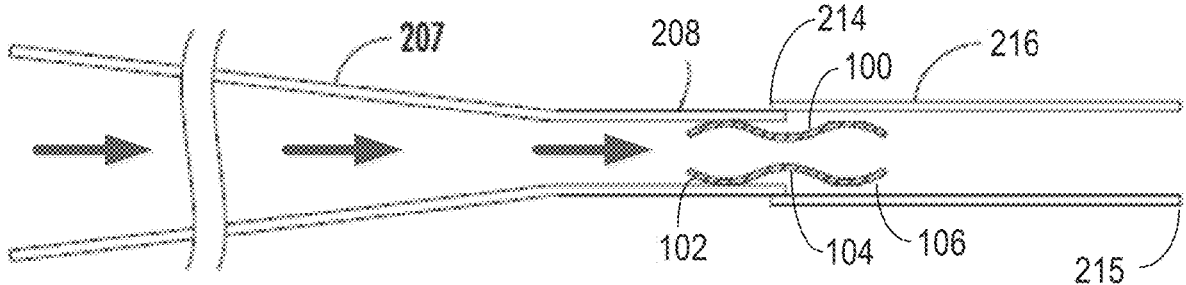

Referring now to FIG. 5D, second flared end region 106 and neck region 104 of shunt 100 are illustrated after having been advanced from introducer tube 208 and into graft tube 216 thereby releasing compressive force on second flared end region 106 and neck region 104, if any. Upon the removal of inward radial force from introducer tube 208, at least second flared end region 106 of shunt 100 may expand radially to a diameter larger than the diameter of graft tube 216, thereby engaging graft tube 216 along the outer surface of second flared end region 106 and neck region 104 in a manner that causes graft tube 216 to expand in an unstressed and unwrinkled fashion. To increase the elasticity of graft tube 216 to permit shunt 100 to expand to its expanded state, heat may be applied to both graft tube 216 and shunt 100. For example, heated air may be directed at graft tube 216 and shunt 100. In an alternative approach, shunt 100 may be cooled below its martensite-to-austenite transformation temperature, such that it becomes martensite. Graft tube 216 may be loaded onto second flared end region 106 and neck region 104 in this contracted state and permitted to slowly expand as shunt 100 warms to room temperature or an elevated temperature in a manner that causes graft tube 216 to expand in an unstressed and unwrinkled fashion.

Figure 5E:
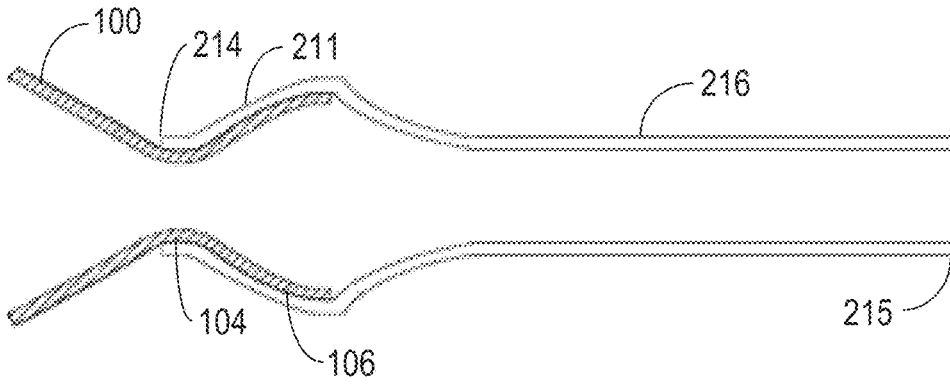

Referring now to FIG. 5E, after depositing first graft portion 211 of graft tube 216 upon second flared end region 106 and neck region 104, shunt 100 may be completely ejected from introducer tube 208, thereby releasing any compressive force on first flared end region 102. Upon being ejected from introducer tube 208, and/or in response to an expandable, shunt 100 may expand and return to the expanded state illustrated in FIG. 5E.

Graft tube 216 may be cut or otherwise manufactured to be the length required to extend along shunt 100 starting at the outer surface of neck region 104 adjacent to first flared end region 102, along the outer surface of neck region 104 and second flared end region 106, along the inner surface of shunt 100 and over the outer surface of first flared end region 102 and neck region 104, terminating at the neck region adjacent to second flared end region 106. Alternatively, graft tube 216 may be longer than desired and may be cut using well-known cutting techniques (e.g., micro-scissors, material cutting guillotine or laser-cutting machine) to achieve the desired length after the approach described with respect to FIGS. 5A-10D has been performed.

Figure 6A:
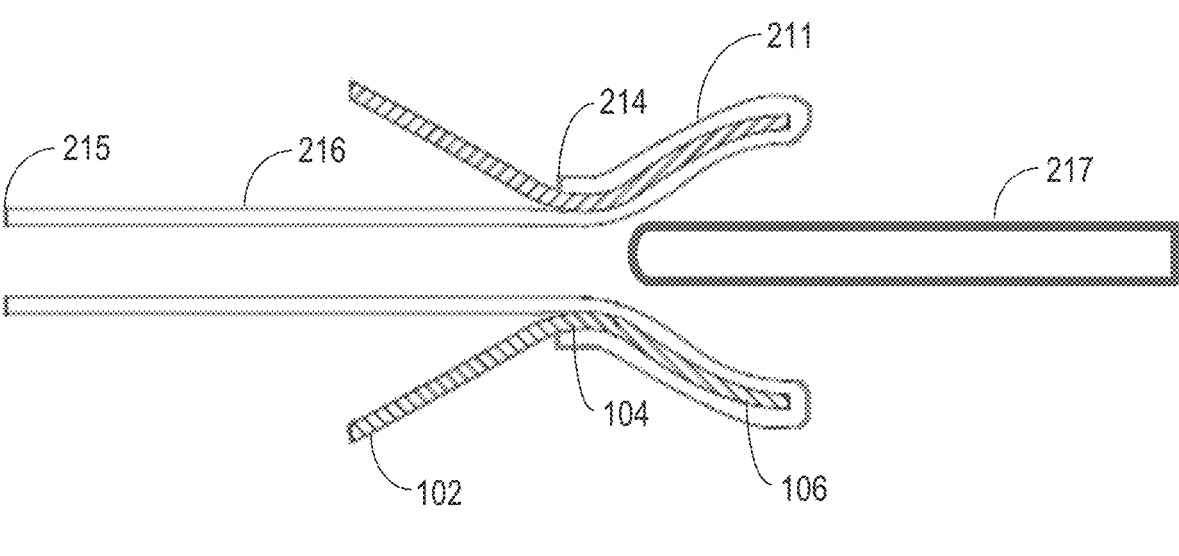
FIGS. 6A and 6B are side views sequentially illustrating a technique of depositing a second graft portion on a shunt.

Referring now to FIG. 6A, to deposit graft tube 216 along the inner surface of shunt 100, graft tube 216 may be guided through the interior of shunt, as shown in FIG. 6A. As shown in FIGS. 6A, graft tube 216 may be everted at one end and guided through an interior of shunt 100 such that the everted portion of graft tube 216 is positioned within the interior of shunt 100. To facilitate this process plunger 217, which may be any tool having a long shaft and a width or diameter less than the inner diameter of neck region 104 in the expanded state, may be used to push graft tube 216 through the interior of shunt 100. In this manner, first graft portion 211 may extend along an outer surface of second flared end region 106, curve around the end of second flared end region 106 and travel along the interior of shunt 100 and out an opposing side of shunt 100.

Figure 6B:
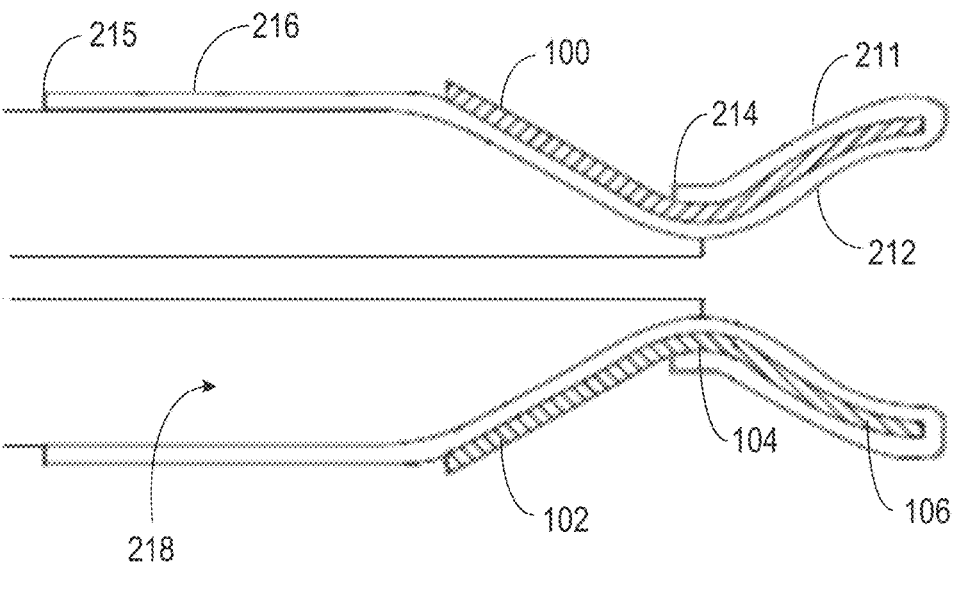

Referring to FIG. 6B, to engage remaining portion of second graft portion 212 with the inner surface of shunt 100, first mandrel portion 218 may be engaged with shunt 100 and second graft portion 212. Having an end-shape formed to correspond to the interior of first flared end region 102, first mandrel portion 218 may be gently advanced within second end 215 of graft tube 216 and shunt 100 until first mandrel portion 218 takes up nearly the entire space within first flared end region 102. This process may involve guiding first flared end region 102 onto first mandrel portion 218 while simultaneously guiding second end 215 of graft tube 216 over first mandrel portion 218 such that second end 215 of the graft tube 216 extends along first mandrel portion 218 in a manner that is tight fitting and free from wrinkles. When first flared end region 102 is properly mounted upon first mandrel portion 218, second end 215 of graft tube 216 will extend beyond the first flared end region 102, as is shown in FIG. 6B. In this manner, second graft portion 212 may be partially engaged with shunt 100 along an inner surface of shunt 100.

Figure 7A:
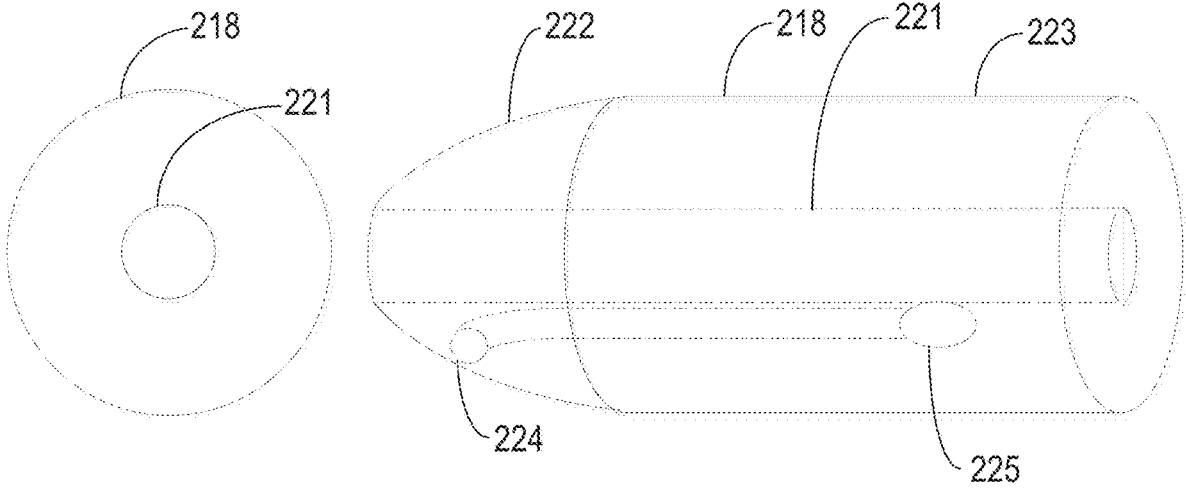
FIGS. 7A and 7B illustrates the mandrel assembly including a first mandrel portion illustrated in FIG. 7A and a second mandrel portion illustrated in FIG. 7B.
Figure 7B:
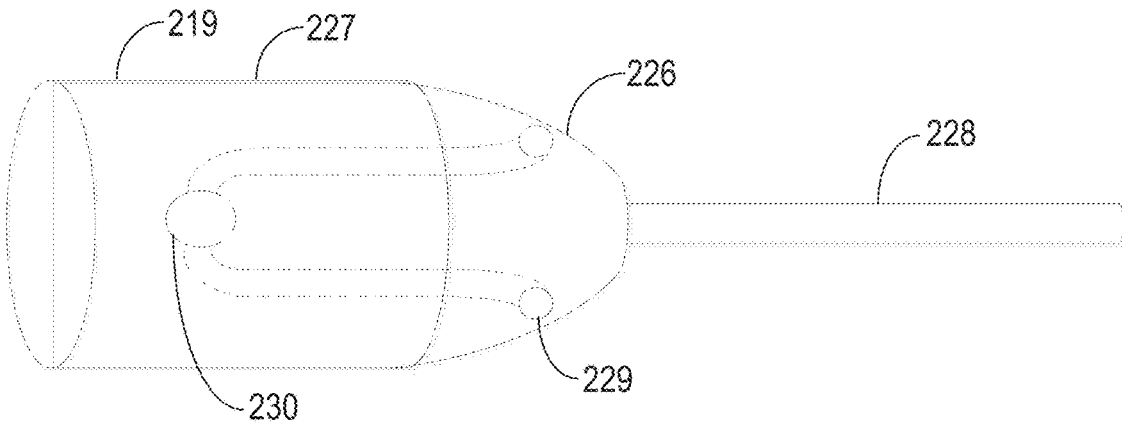
Figures 8A, 8B, 8C:
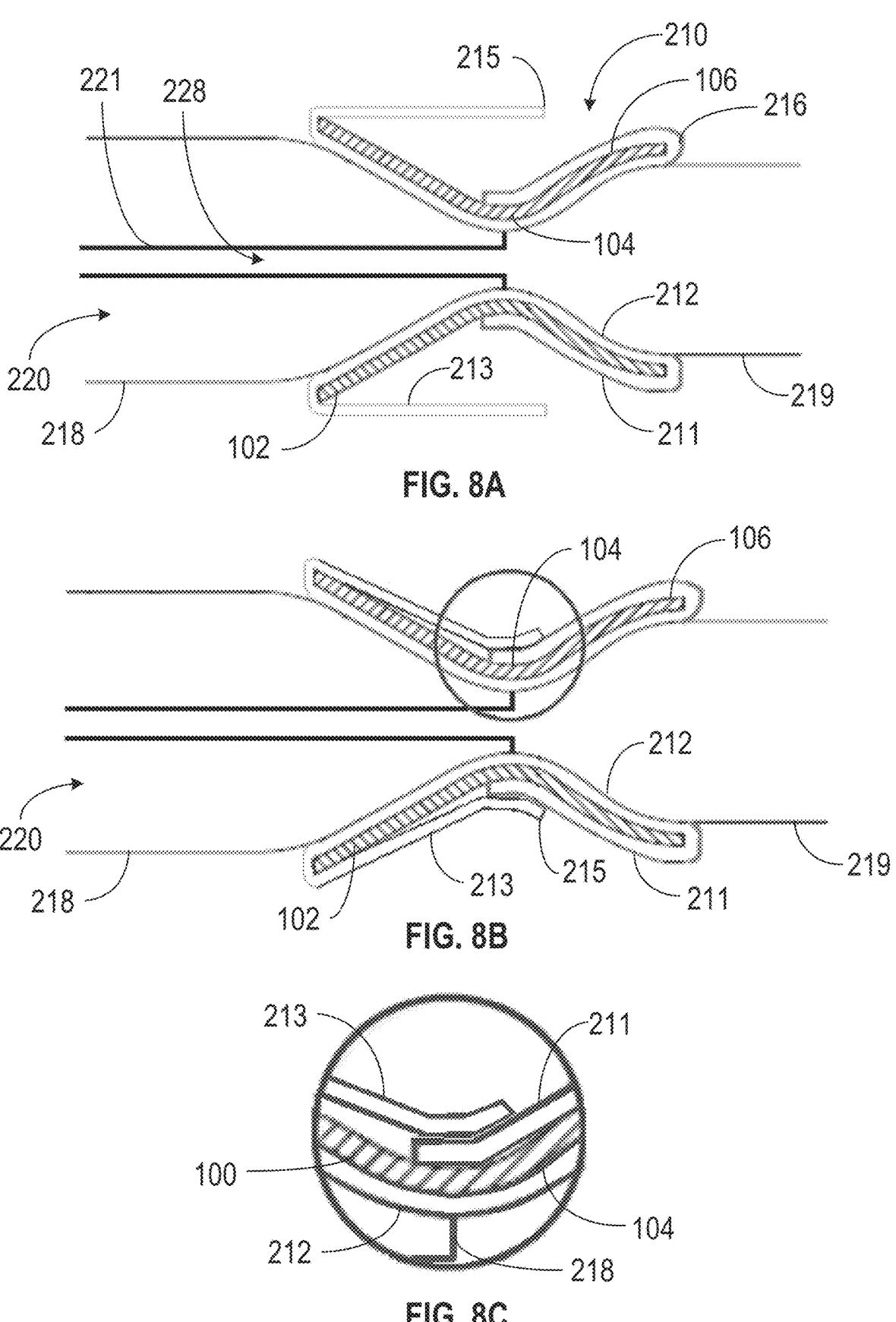
FIGS. 8A-8C are side views and a close-up view illustrating a technique of depositing a third graft portion on a shunt.

Referring now to FIGS. 7A and 7B, first mandrel portion 218 (FIG. 7A) and second mandrel portion 219 (FIG. 7B) are illustrated. As is illustrated in FIGS. 8A and 8B, first mandrel portion 218 and second mandrel portion 219 may be removably coupled to form mandrel assembly 220. Referring now to FIG. 7A, a side view and head-on view of first mandrel portion 218 is illustrated. First mandrel portion 218 may have first retention portion 222 and first body portion 223, where first retention portion 222 extends from first body portion 223. First retention portion 222 is designed to engage with shunt-graft assembly 210 and have a similar shape as the first flared end region and/or the neck region only with slightly smaller dimensions. First body portion 223 may have a cylindrical shape. It is understood that first mandrel portion may alternatively only have first retention portion 222. First mandrel portion 218 may have receiving portion 221 sized and configured to receive protruding portion 228 of second mandrel portion 219. Receiving portion 221 may extend the entire length of first mandrel portion 218 or may alternatively only extend a portion of first mandrel portion 218.

First mandrel portion 218 may also, optionally, have one or more ventilation holes 224 in first retention portion 222. Ventilation holes 224 may extend through an exterior surface of first retention portion 222 and may tunnel through the interior of first retention portion 222 and first body portion 223 to ventilation inlet 225 which may extend through the surface of first body portion 223. Ventilation holes 224 are preferably in the range of 0.1-2 mm in size, though it is understood that ventilation holes of different sizes may be beneficial. Ventilation holes 224 may facilitate release of stent-graft assembly 210 after the heat treatment is applied, as explained below with respect to FIGS. 10A and 10B. Specifically, after the encapsulated stent is tightly compressed against mandrel assembly 220, and the air between the encapsulated stent and mandrel assembly 220 is vacated, there may exist a suction force making it difficult to remove the encapsulated stent. Ventilation inlet 225 may permit air to flow through ventilation inlet to ventilation holes 224 to eliminate or reduce the suction effect. It is understood that multiple ventilation holes may communicate with one or more ventilation inlets.

Referring now to FIG. 7B, second mandrel portion 219 is illustrated. Second mandrel portion 219 may have second retention portion 226 and second body portion 227, where second retention portion 226 extends from second body portion 227. Second retention portion 226 is designed to engage with shunt-graft assembly 210 and may have a similar shape as the second flared end region and/or the neck region only with slightly smaller dimensions. Second body portion 227 may have a cylindrical shape. It is understood that second mandrel portion may alternatively only have second retention portion 226.

Second mandrel portion 219 has protruding portion 228 sized and shaped to be received by receiving portion 221 of first mandrel portion 218. Protruding portion 228 may be, for example, a shaft that extends from second retention portion 226. Protruding portion may be coaxial with second mandrel portion 219 and may be designed to extend part of the length, the entire length or more than the length of first mandrel portion 218. Like first mandrel portion 218, second mandrel portion 219 may, optionally, include one or more ventilation holes 229 and one or more ventilation inlets 230.

Referring now to FIG. 8A, to constrain shunt-graft assembly 210 on mandrel assembly 220, second mandrel portion 219 is removably coupled with first mandrel portion 218 by engaging protruding portion 228 with receiving portion 221. Second mandrel portion 219 may be gently advanced within second flared end region 106 of shunt-graft assembly 210 toward first mandrel portion 218 until second mandrel portion 219 takes up nearly the entire space within second flared end region 106 and protruding portion 228 is fully received by receiving portion 221. In this manner, second graft portion 212 may be fully engaged with second flared end region 106.

Protruding portion 228 may be designed to engage with receiving portion 221 such that protruding portion 228 and engagement portion are releasably locked together. Alternatively, protruding portion 228 may be design to friction fit within receiving portion 221. For example, protruding portion may be designed with a gradually increasing diameter that may result in a friction fit with receiving portion 221. In this example, first mandrel portion 218 and second mandrel portion 219 may be released by forcibly pulling first mandrel portion 218 and second mandrel portion 219 apart. It is understood that first mandrel portion 218 and second mandrel portion 219 may be releasably locked together or otherwise friction fit together using various other well-known techniques. It is further understood that protruding portion 228 may instead extend from first mandrel portion 218 and receiving portion 221 may instead be formed within second mandrel portion 219.

As is shown in FIG. 8A, after engaging second mandrel portion 219 with first mandrel portion 218, and thus constraining shunt-graft assembly 210 on mandrel assembly 220, third graft portion 213 may be separated from the surface of first mandrel portion 218. For example, forceps may be used to grasp second end 215 of graft tube 216 and gently pull second end 215 over first flared end region 102 and over neck region 104. In this manner, graft tube 216 may be everted and guided over first flared end region 102 and over neck region 104. Alternatively, other well-known techniques may be used for separating third graft portion 213 from first mandrel portion 218 and depositing third graft portion 213 over first flared end region 102 and neck region 104.

Referring now to FIG. 8B, third graft portion 213 may gently be compressed against first flared end region 102 and neck region 104 in a manner that reduces or eliminates wrinkles. For example, second end 215 may be manually stretched using forceps toward neck region 104 and gently permitted to make contact with first flared end region 102 and the portion of first graft portion 211 in contact with neck region 104.

By placing third graft portion 213 over first flared end region 102 and neck region 104, graft tube 216 will be deposited over shunt 100 such that graft tube 216 covers shunt 100 in the manner depicted in FIGS. 4A-4D. As is shown in FIG. 8C, depositing graft tube 216 over shunt 100 in the foregoing manner results in three biocompatible layers of graft material covering neck region 104 of shunt 100. Specifically, as is shown in FIG. 8C, neck region 104 of shunt 100 is covered on an inner surface by second graft portion 212 and is covered on an outer surface by first graft portion 211 and third graft portion 213. In FIG. 8C, third graft portion 213 overlaps first graft portion 211 at neck region 104. As is shown in FIGS. 4B and 4D, first flared end region 102 and second flared end region 106 of shunt 100 may only be covered by two layers of biocompatible material. In this manner, second graft portion 212 may extend through a lumen of shunt 100 through the first end of first flared end region 102, through neck region 104, and to the end of second flared end region 106; first graft portion 211 extends along an outer surface of second flared end region 106 and neck region 104; and third graft portion 213 extends along an outer surface of first flared end region 102 and neck region 104, overlapping, at least partially, and joining with first graft portion 211.

It is understood that graft tube 216 may be deposited upon shunt 100 to form shunt-graft assembly 210 having the same three-layer structure at the neck region 104 and two-layer structure at first flared end region 102 and second flared end region 106 using different approaches than the approach detailed in FIGS. 5A-8C. It is further understood that a three-layer structure may be deposited upon shunt 100 in a similar manner but resulting in the three-layer structure occurring over first flared end region 102, second flared end region 106, and/or neck region 104. In another example, a similar approach may be used to create shunt-graft assembly having one region with four layers of biocompatible material and other regions with two layers of biocompatible material. These and other methods and embodiments are further described in U.S. Pat. No. 11,304,831.

Referring now to FIGS. 9A-9D, to securely bond first graft portion 211, second graft portion 212, and third graft portion 213 to shunt 100 and one another, pressure and heat may be applied to shunt-graft assembly 210 to achieve sintering. As explained above, sintering results in strong, smooth, substantially continuous coating that covers the inner and outer surfaces of the stent. Sintering may be achieved by first covering shunt-graft assembly 210 with a flexible sleeve (e.g., flexible clamshell 231 shown in FIG. 9A), applying compressor 232 (shown in FIG. 10A), and/or applying heat. In this manner, the first graft portion, second graft portion, and third graft portion may be bonded to one another through through-wall openings in shunt 100. Accordingly, third graft portion and second graft portion may be sintered together and joined.

The flexible sleeve may be tubular and also may be elastic and biocompatible. For example, the flexible sleeve may be flexible clamshell 231 illustrated in FIG. 9A. Flexible clamshell 231 is preferably made from biocompatible silicone but may alternatively be other biocompatible materials having elastic properties. Flexible clamshell 231 is hollow and may have a consistent thickness. Alternatively, flexible clamshell 231 may have varying thickness at different points or in different sections. Flexible clamshell 231 has first end 235 and second end 236 which may come together in a neutral position. Alternatively, in a neutral position, there may exist a longitudinal void between first end 235 and second end 236. Flexible clamshell 231 is designed such that first end 235 and second end 236 may be separated by pulling first end 235 and second end 236 in opposing directions.

Figure 9A:
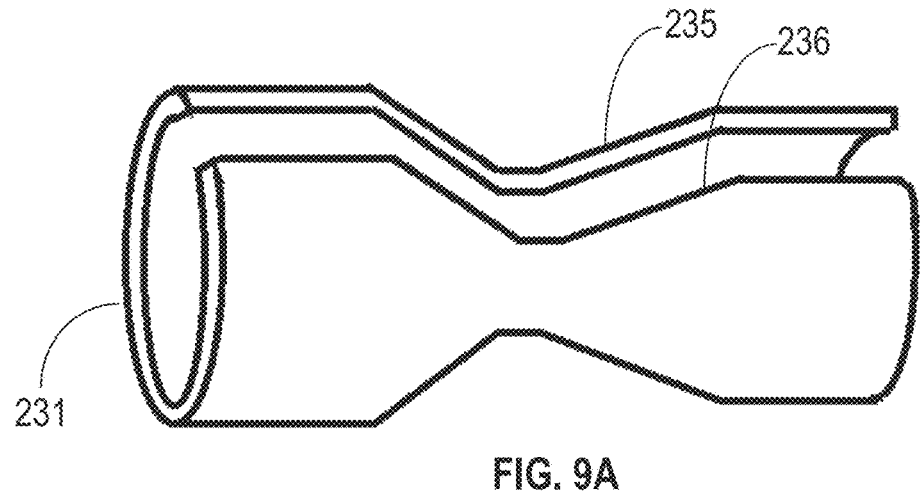
FIGS. 9A and 9B illustrate a perspective view of the flexible sleeve and a side view of the flexible sleeve mounted on the shunt-graft assembly.
Figure 9B:
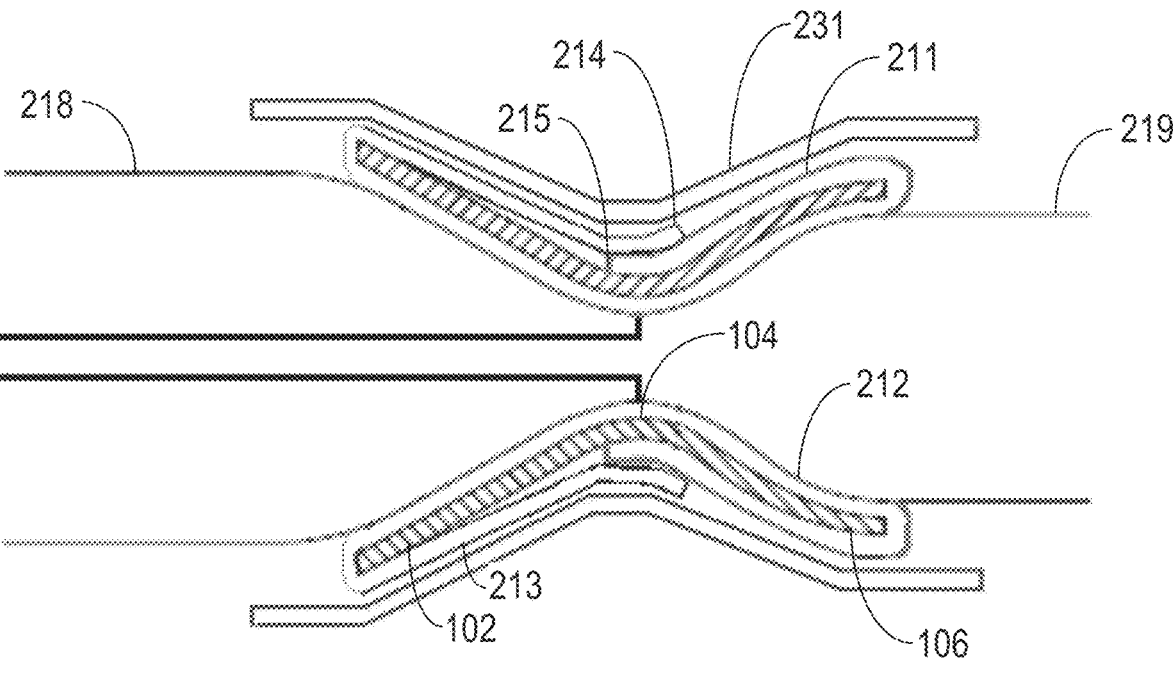

Referring now to FIG. 9B, first end 235 and second end 236 may be pulled in opposing directions to create a longitudinal void such that, while shunt-graft assembly 210 is positioned upon mandrel assembly 220, first end 235 and second end 236 may pulled over shunt-graft assembly 210. In this manner, flexible clamshell 231 either entirely or nearly entirely covers shunt-graft assembly 210. Flexible clamshell 231 may be sized such that flexible clamshell 231 fits tightly over shunt-graft assembly 210, as is illustrated in FIG. 9B. It is understood that a thin metallic layer may be deposited over shunt-graft assembly 210 prior to covering shunt-graft assembly 210 in clamshell 231 such that the thin the metallic layer may be sandwiched between shunt-graft assembly 210 and flexible clamshell 231 and may serve as a barrier between shunt-graft assembly 210 and flexible clamshell 231. This barrier may help prevent contaminants from clamshell 231 from transferring to shunt-graft assembly 210. In one example, the thin metallic layer may be aluminum foil. In other examples, the thin metallic layer may be titanium, tantalum, or stainless steel, though it is understood that other metals or alloys may be used. This process has been observed to enhance the compression and sintering process. Where the stent-graft assembly is wrapped with tape such as TFE or ePTFE tape, the tape may similarly prevent contaminants from transferring to the shunt-graft assembly.

Flexible clamshell 231 may be sized such that when positioned over shunt-graft assembly 210, flexible clamshell 231 applies a compressive force on shunt-graft assembly 210. Flexible clamshell 231 may be sized and configured to optimize the conformance of graft tube 216 to shunt 100 to minimize gaps between layers of graft tube 216 adjacent to struts of shunt 100. The degree of pressure that flexible clamshell 231 applies to shunt-graft assembly 210 may alter the internodal distance (IND) of the graft material once sintered, described in more detail below. The extent to which flexible clamshell 231 covers, or does not cover, shunt-graft assembly 210 also may alter the internodal distance. It is understood that internodal distance is related to tissue ingrowth and that the compressive force applied by flexible clamshell 231 may be altered to achieve the desired internodal distance. Alternatively, any compressive force applied by flexible clamshell 231 may be negligible. Additional compression force on shunt-graft assembly 210 may optionally be achieved by first wrapping shunt-graft assembly 210 and/or flexible clamshell 231 with tape such as TFE or ePTFE tape. For example, shunt-graft assembly 210 covered by flexible clamshell 231 may be placed in a helical winding wrapping machine which tension wraps the shunt-graft assembly 210 and flexible clamshell 231 with at least one overlapping layer of tape, explained in more detail above.

Figures 10A, 10B:
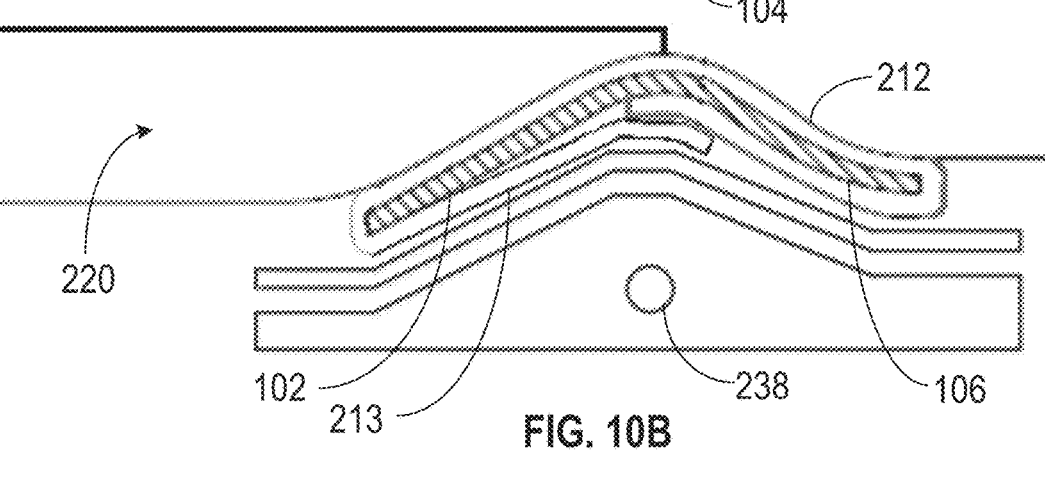
FIGS. 10A and 10B illustrate a perspective view of a compression shell and a side view of the compression shell mounted on the flexible sleeve and shunt-graft assembly.

Referring now to FIGS. 10A and 10B, compressor 232 is illustrated. Compressor 232 has first half 233 and second half 234 and further includes couplers 237 for removably coupling first half 233 to second half 234. Couplers 237 may involve a screw with a locking nut or any other well-known technique for removably locking two components together. First half 233 and second half 234 may include receiving portions 238 that are sized and configured to receive couplers 237. First half 233 and second half 234 have an interior indentation configured to receive shunt-graft assembly 210 covered by flexible clamshell such that the interior indentation of each of first half 233 and second half 234, when removably coupled together, has the shape of shunt-graft assembly 210 covered by flexible clamshell 231. Alternatively, the interior indentation of each of first half 233 and second half 234, when removably coupled together, has the shape of the mandrel assembly 220, except with slightly larger radial dimensions.

First half 233 and second half 234 are rigid and preferably are stainless steel though it is understood that first half 233 and second half 234 may be other rigid materials. First half 233 and second half 234 may be designed such that first half 233 and second half 234 are positioned a constant distance from shunt-graft assembly 210 when first half 233 and second half 234 are coupled together. Alternatively, the distance from shunt-graft assembly 210 or the mandrel assembly 220 may vary at different regions of first half 233 and second half 234. First half 233 and second half 234 may be designed with a wall thickness between an interior surface of first half 233 and second half 234 and an exterior surface of first half 233 and second half 234 that permits a desired degree of heat transfer. For example, first half 233 and second half 234 may have a wall thickness that is thin to increase the amount of heat transfer to the stent-graft assembly. A thinner wall thickness may result in shorter sintering times, which may improve production rates. Further, shorter sintering times lessen the effect of sintering on the transformation temperatures (e.g., Austenitic Finish (At)) of the Nitinol frame.

Referring now to FIG. 10B, compressor 232 may be attached to clamshell 231 covering shunt-graft assembly 210 while shunt-graft assembly 210 is mounted upon mandrel assembly 220. Specifically, first half 233 may be positioned over a first half portion of shunt-graft assembly 210 and clamshell 231 and second half 234 may be positioned over a second half portion of clamshell 231 and shunt-graft assembly 210 such that first half 233 and second half 234 entirely or nearly entirely cover flexible clamshell 231. Once receiving portions 238 of first half 233 and second half 234 are aligned, couplers 237 may be inserted into receiving portions 238 to removably couple first half 233 to second half 234 over clamshell 231. Couplers 237 may be tightened to increase the compressive force applied to shunt-graft assembly 210. It is understood that the compressive force applied by couplers 237 may alter the internodal distance of the graft material once sintered. It is further understood that couplers 237 may be tightened to a certain degree to achieve a desired internodal distance.

Upon coupling first half 233 to second half 234 around flexible clamshell 231, compressor 232 will have been positioned over flexible clamshell 231, flexible clamshell

231 will have been positioned over shunt-graft assembly 210, and shunt-graft assembly 210 will have been positioned over mandrel assembly 220, as is illustrated in FIG. 10B, forming sintering assembly 239. Upon coupling first half 233 to second half 234, compressor 232 applies a compressive force upon flexible clamshell 231 and shunt-graft assembly 210, thereby compressing shunt-graft assembly 210 against mandrel assembly 220. Flexible clamshell 231, due to its elastic properties, may facilitate even distribution of compressive force against shunt-graft assembly 210. Shunt 100 may comprise a plurality of through-wall openings. The force exerted by wrapping tape and/or compressor 232 compresses shunt-graft assembly 210 against mandrel assembly 220, thereby causing the graft layers to come into intimate contact through interstices of shunt 100.

It may be desirable for compressor 232 to apply uniform compressive force. Alternatively, it may be desirable to vary the compressive force applied to shunt-graft assembly 210 at certain points along shunt-graft assembly 210. For example, flexible clamshell 231 may have varying thickness and/or length, permitting compressor 232 to distribute varying degrees of compressive force upon shunt-graft assembly according to the wall thickness and geometry of flexible clamshell 231. Additionally, the distance from the interior walls to the surface of shunt-graft assembly 210 may vary at certain points along first half 233 and/or second half 234. For example, a region of an interior wall of first half 233 having a distance to shunt-graft assembly 210 less than the rest of first half 233 may apply a greater compression force on shunt-graft assembly 210. Varying compressive force applied to shunt-graft assembly 210 may reduce or increase conformance between first graft portion 211, second graft portion 212, and third graft portion 213. In an alternative embodiment, compressor 232 may be designed such that it only applies a compression force at neck region 104.

To form a monolithic layer of biocompatible material, first graft portion 211, second graft portion 212, and third graft portion 213 of graft tube 216 may be securely bonded together by applying heat to sintering assembly 239. For example, sintering assembly 239 may be heated by placing sintering assembly 239 into a radiant heat furnace, which may be preheated. Sintering may be performed as discussed in more detail in U.S. Pat. No. 11,304,831. The heated assembly may then be allowed to cool for a period of time sufficient to permit manual handling of the assembly. After cooling, first half 233 and second half 234 of compressor 232 may be decoupled and removed from flexible clamshell 231. Next, helical wrap, if any, may be unwound and discarded. Flexible clamshell 231 may be removed and encapsulated stent may then be concentrically rotated about the axis of the mandrel to release any adhesion between the second graft portion 212 and mandrel assembly 220. The encapsulated stent, still on mandrel assembly 220, may then be placed into a laser-trimming fixture to trim excess graft materials away, in any. In addition, the graft material of the encapsulated stent may be trimmed at various locations along the stent such as near one of the stent ends to permit coupling to delivery device, for example, as shown in FIG. 1C.

The resulting structure shown in FIG. 4A-4D and created using the approach described with respect to FIGS. 5A-10B is beneficial in that biocompatible material does not terminate at either end of shunt-graft assembly 210 but instead terminates at neck region 104 of shunt 100. The inventors have discovered that biocompatible material that extends beyond a stent at either end is known to result in thrombus formation when implanted and could also cause interference with attachment to a delivery catheter. The reduction in graft overhang at the edges also improves fluid dynamics at the inlet and outlet of the encapsulated stent. As an added benefit, the resulting triple-layer structure at neck region 104 has been observed by the inventors to further inhibit tissue ingrowth. It is understood that the foregoing method described with respect to FIGS. 5A-10B helps prevent gaps between biocompatible layers at the flared end regions, which might result in extensive tissue ingrowth, and also helps minimize microscopic surface thinning defects (MSTDs), which could result in attracting platelet thrombi. Applicants understand that the approach described with respect to FIGS. 5A-10B provides a high yield and highly reproducible manufacturing process.

Applicants have further observed that heating sintering assembly 239 including a flexible clamshell comprised of silicone, as described herein, results in small fragments and/or molecular portions of silicone being deposited upon graft tube 216 and/or becoming impregnated in graft tube 216. It has been observed by the Applicant that the fragments and/or molecular portions of silicone deposited on and/or impregnated in graft tube 216 may further reduce tissue ingrowth when the encapsulated stent is implanted.

Referring now to FIGS. 11A-11D, a first embodiment of a shunt-graft assembly of FIGS. 4A-4D further including the bridge described above is illustrated. Shunt 100 may be covered with a single tube of biocompatible material, as shown in FIG. 4A, to create shunt-graft assembly 210 having varying layers of biocompatible material (e.g., two-to-three layers of biocompatible material). For example, graft tube 216 may be deposited over shunt 100 such that second graft portion 212 extends through a lumen of shunt 100 through the first end of first flared end region 102, through neck region 104, and to the end of second flared end region 106; first graft portion 211 extends along an outer surface of second flared end region 106 and neck region 104; and third graft portion 213 extends along an outer surface of first flared end region 102 and neck region 104, overlapping, at least partially, and joining with first graft portion 211. After depositing graft tube 216 onto shunt 100, bridge 240 may be deposited onto shunt-graft assembly 210.

Bridge 240 may be a single tube of biocompatible material similar to the material of graft tube 216. As described with reference to FIG. 1B, the biocompatible material of bridge 240 preferably is one that encourages tissue adherence such that contact with the septal wall is maintained if the inner diameter of the shunt is decreased. The biocompatible material may be configured to promote tissue ingrowth over the entire bridge or over only a portion of the bridge. For example, holes may be placed at the location of bridge 240 that is configured to engage the atrial septum while the remainder of bridge 240 remains whole such that tissue ingrowth is not encouraged on the flared end regions. Such addition of holes or other processing to promote tissue ingrowth or encourage adhesion may be performed on the biocompatible material prior to or after the shunt is assembled. In addition, or alternatively, bridge 240 may be made of a different biocompatible material than the biocompatible material used to encapsulate the shunt. For example, the shunt may be encapsulated with a biocompatible material, such as ePTFE, having a sufficiently small pore size such that tissue ingrowth is mitigated and the bridge may be made of a biocompatible material having a larger pore size that is designed to encourage tissue ingrowth. Alternatively, bridge 240 may be made of woven Dacron, a mesh-like structure, electrospun fabrics, or silicone to further encourage tissue ingrowth. As described further above, if woven Dacron is used to form the bridge, the Dacron may be securely attached to the encapsulated shunt using stitches rather than the method described below. In some embodiments, the shunt may be encapsulated with ePTFE having a thickness of 0.002" and an internodal distance of <=30 microns. Clowes et al., Rapid Transmural Capillary Ingrowth Provides a Source of Intimal Endothelium and Smooth Muscle in Porous PTFE Prostheses, Arterial Graft Failure, Vol. 123, No. 2, pages 220-230 (May 1986) describes that ePTFE with IND<=30 microns exhibits low porosity and Applicant's studies have shown that tissue ingrowth is inhibited within shunts encapsulated with ePTFE with IND=30 microns. On the other hand, bridge 240 may have a thickness of 0.002" or 0.005" and a pore size to augment cellular and collagen transmural infiltration into the potential space between bridge 240 and other layers of ePTFE. This can be done using a larger pore size ePTFE (for example with an ePTFE material having IND ranging from 60 to 200 microns). Alternatively, transmural infiltration may be encouraged by creating a pattern or plurality of perforations of similar dimension into bridge 240 fabricated from conventional low-porosity (IND<=30 microns), either before or after its application to the shunt. Such dedicated perforation process may be performed using, e.g., an energy source such as laser, RF, etc., or a mechanical source e.g. punch, or any other technique know to those skilled in the art of thin materials processing. In some embodiments, the frame encapsulation material is intended to block tissue ingrowth, whereas the bridge encapsulation material would be more elastic to support the significant expansion/contraction in diameter, without damaging the Fossa Ovalis or the frame encapsulation material. In some embodiments, the gap 243 between the bridge 240 and the neck region 104 increases as the shunt neck region 104 is contracted. Bridge 240 may be configured to remain engaged with the patient's atrial septum when the neck region is contracted. In some embodiments, the biocompatible material of bridge 240 has a porosity (as measured by, e.g., its internodal distance) greater than the porosity of the biocompatible material of the encapsulation of the shunt frame. As such, the internodal distance of the bridge material may be selected to permit tissue ingrowth while the internodal distance of the encapsulation material is selected to inhibit tissue ingrowth. In some embodiments, the internodal distance of the bridge is greater than 30 microns (e.g., in a range of 45-200 microns) while the internodal distance of the encapsulation is less than or equal to 30 microns. In one embodiment, the internodal distance of the bridge is 60 microns while the internodal distance of the encapsulation is 30 microns. The biocompatible material of the bridge and the biocompatible material of the encapsulation may be expanded polytetrafluoroethylene (ePTFE).

Bridge 240 may have a length shorter than shunt-graft assembly 210 and a diameter greater than the diameter of neck region 104. Preferably, bridge 240 is shaped and sized such that, after depositing bridge 240 over neck region 104, first end 241 extends approximately half way up first flared end region 102, second end 242 extends approximately half way up second flared end region 106, and gap 243 is created between neck region 104 and bridge 240.

Figures 11A, 11B, 11C, 11D, 11E, 11F:
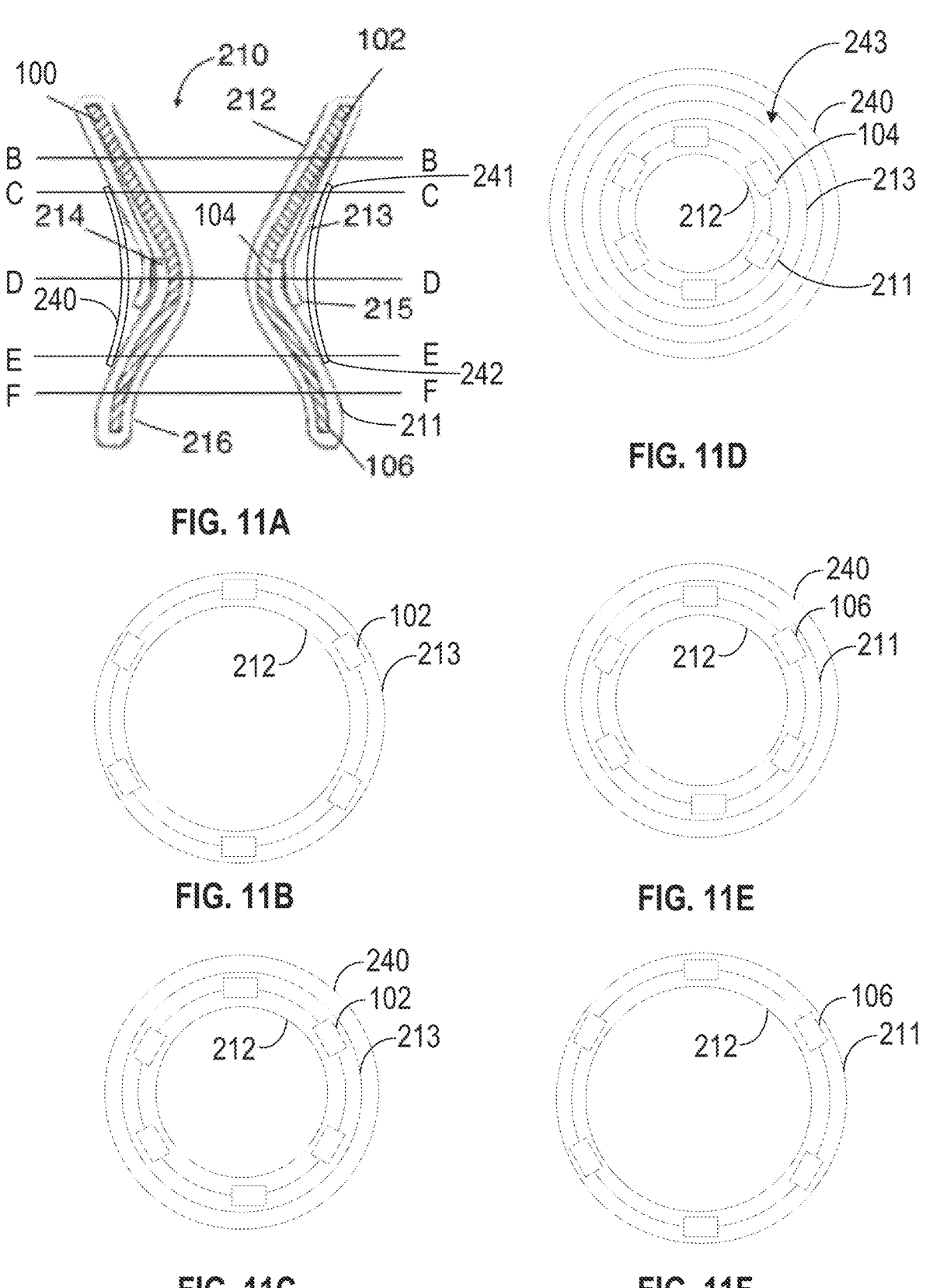
FIGS. 11A-11F illustrate a first embodiment of a shunt-graft assembly of FIGS. 4A-4D having a bridge.

The cross sections of shunt-graft assembly 210 illustrated in FIG. 11A (cross-sections B, C, D, E, and F) are illustrated in FIGS. 11B, 11C, 11D, 11E, and 11F, respectively. The thickness of the graft material is exaggerated in the cross-sectional views in order to better illustrate the different layers of graft material over shunt 100. As will be understood by one of skill in the art, the different cross-sections of the flared end regions and the neck region may be greater than or less than the cross-sections shown in FIGS. 11B-11F. Referring now to FIG. 11B, cross-section B of shunt-graft assembly 210 is illustrated. As is shown in FIG. 11B, first flared end region 102 of shunt 100 may be covered on the outer surface and the inner surface by graft tube 216. Specifically, first flared end region 102 may be covered on the outer surface by third graft portion 213 and on the inner surface (i.e., on the interior of first flared end region 102) by second graft portion 212. Accordingly, shunt 100 may be covered at first flared end region 102 by two layers of biocompatible material. From the location where first end 241 of bridge 240 is coupled to third graft portion 213 and to neck region 104, first flared end region 102 may be covered by three layers of biocompatible material, for example as shown in FIG. 11C.

Referring now to FIG. 11D, cross-section D of shunt-graft assembly 210 is illustrated. As is shown in FIG. 11D, neck region 104 of shunt 100 may be covered by three layers of biocompatible material on the outer surface and one layer of biocompatible material on the inner surface of neck region 104. Specifically, neck region 104 may be first covered on the outer surface by first graft portion 211, which is covered by third graft portion 213. Further, neck region 104 may be covered by bridge 240 and gap 243 may extend between third graft portion 213 and bridge 240. On the inner surface (i.e., on the interior of neck region 104), shunt 100 may be covered by second graft portion 212. Accordingly, shunt 100 of the shunt-graft assembly 210 may be covered at neck region 104 by four layers of biocompatible material.

Referring now to FIG. 11F, cross-section F of shunt-graft assembly 210 is illustrated. As is shown in FIG. 11F, second flared end region 106 of shunt 100 is covered on the outer surface and the inner surface by graft tube 216. Specifically, second flared end region 106 may be covered on the outer surface by first graft portion 211 and on the inner surface (i.e., on the interior of second flared end region 106) by second graft portion 212. Accordingly, shunt 100 of shunt-graft assembly 210 may be covered at second flared end region 106 by two layers of biocompatible material. From the location where second end 242 of bridge 240 is coupled to first graft portion 211 and to neck region 104, second flared end region 106 may be covered by three layers of biocompatible material, for example as shown in FIG. 11E.

Bridge 240 may be deposited on shunt-graft assembly 210 in a manner similar to the method described in FIGS. 5A-10D. Preferably, bridge 240 is incorporated to the device after graft tube 216 is sintered to shunt 100 to form a monolithic layer of biocompatible material, thereby ensuring graft tube 216 remains in the proper location while bridge 240 is deposited on shunt-graft assembly 210. For example, shunt-graft assembly 210 may be placed within a funnel and advanced towards a reduced section of the funnel. Shunt-graft assembly 210 may then be inserted into an introducer tube, which may have a smaller diameter than the diameter of bridge 240. The introducer tube may then be inserted into first end 241 of bridge 240 and may be advanced partially out second end 242. Shunt-graft assembly 210 may then be advanced out of the introducer tube such that second flared end 106 extends past second end 242 and first flared end 102 extends in the opposite direction past first end 241. Bridge 240 may then be positioned over neck region 104 such that first end 241 is disposed approximately half way up first flared end region 102, second end 242 is disposed approximately half way up second flared end region 106, and gap 243 is disposed between neck region 104 and bridge 240. Gap 243 may be created by manually stretching (e.g., using forceps) first end 241 toward first flared end region 102 and second end 242 toward second flared end region 106.

To securely bond first end 241 to third graft portion 213 and second end 242 to first graft portion 211, pressure may be applied to shunt-graft assembly 210 to achieve sintering. Additionally or alternatively, gap 243 may be filled with a biocompatible material, as shown in FIG. 2B. For example, a biocompatible material may be deposited on shunt-graft assembly 210 at the neck region either before or after bridge 240 is deposited over neck region 104.

FIGS. 12A-12D illustrate another embodiment of a shunt-graft assembly of FIGS. 4A-4D further including the bridge described above is illustrated. As described above, shunt 100 may be encapsulated to create shunt-graft assembly 210 having varying layers of biocompatible material, such as two layers over first flared end region 102 and second flared end region 106 and three layers over neck region 104. After depositing graft tube 216 onto shunt 100, bridge 240 may be deposited onto shunt-graft assembly 210.

Bridge 240 may be created using second graft tube 245, which may be a single tube of biocompatible material similar to the material of graft tube 216. Second graft tube 245 may have a length that is greater than two times the length of shunt 100 and a diameter greater than the diameter of neck region 104. Second graft tube 245 may comprise fourth graft portion 246, fifth graft portion 247, and sixth graft portion 248. Preferably, fourth graft portion 246 extends over neck region 104 to create bridge 240.

Figure 12B:
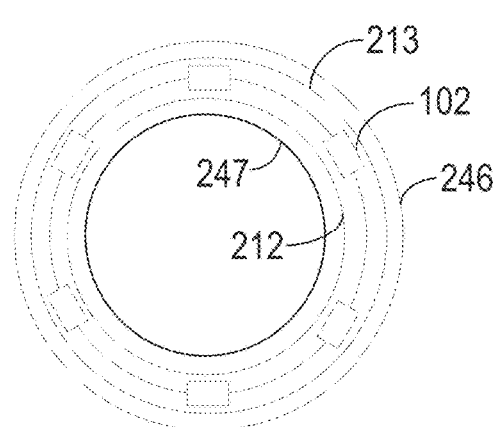
FIGS. 12A-12D illustrate a second embodiment of a shunt-graft assembly of FIGS. 4A-4D having a bridge.
Figure 12A:
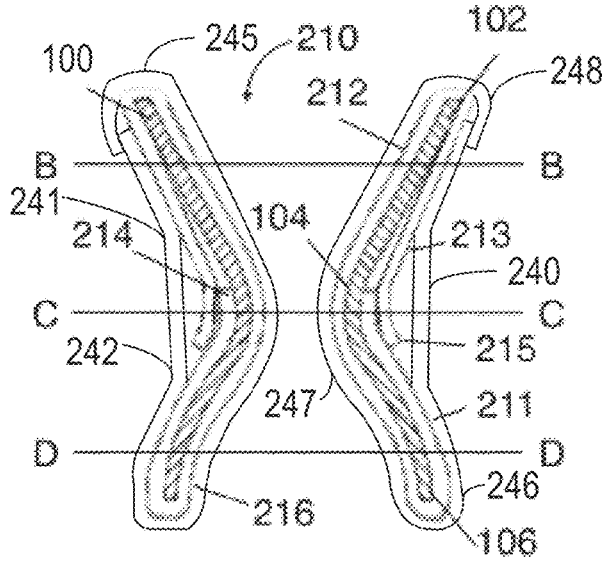
Figure 12A:
Figure 12C:
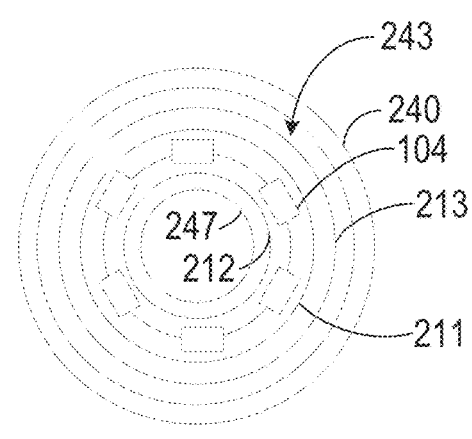
Figure 12D:
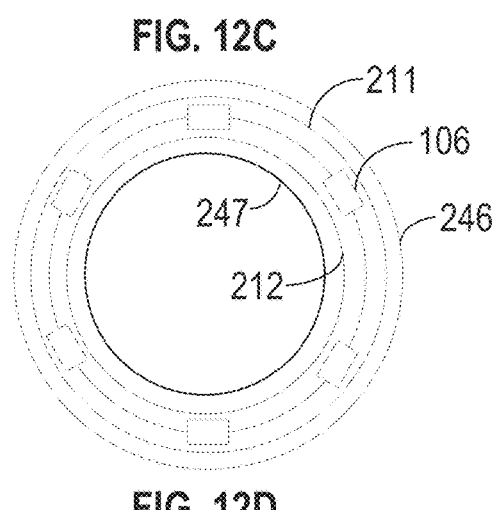

The cross sections of shunt-graft assembly 210 illustrated in FIG. 12A (cross-sections B, C, and D) are illustrated in FIGS. 12B, 12C, and 12D, respectively. The thickness of the graft material is increased in the cross-sectional views in order to better illustrate the different layers of graft material over shunt 100. As will be understood by one of skill in the art, the different cross-sections of the flared end regions and the neck region may be greater than or less than the cross-sections shown in FIGS. 12B-12D. Referring now to FIG. 12B, cross-section B of shunt-graft assembly 210 is illustrated. As is shown in FIG. 12B, first flared end region 102 of shunt 100 may be covered on the outer surface and the inner surface by graft tube 216. Specifically, first flared end region 102 may be covered on the outer surface by third graft portion 213 of graft tube 216 and on the inner surface (i.e., on the interior of first flared end region 102) by second graft portion 212 of graft tube 216. Further, second graft tube 245, having fourth, fifth, and sixth graft portions 246, 247, and 248, may be deposited over graft tube 216. Specifically, first flared end region 102 may be covered on the outer surface by fourth graft portion 246 of second graft tube 245, which may extend over third graft portion 213 of graft tube 216, and on the inner surface by fifth graft portion 247 of second graft tube 245, which may extend over second graft portion 212 of graft tube 216. At some portions of first flared end region 102, sixth graft portion 248 of second graft tube 245 may be deposited such that it overlaps fourth graft portion 246. Accordingly, shunt 100 may be covered at first flared end region 102 by four or five layers of biocompatible material. As understood by one of skill in the art, the fourth graft portion 246 may instead overlap sixth graft portion 248 on second flared end region 106, such that first flared end region 102 is covered only by four layers of biocompatible material.

Referring now to FIG. 12C, cross-section C of shunt-graft assembly 210 is illustrated. As is shown in FIG. 12C, neck region 104 of shunt 100 may be covered by three layers of biocompatible material on the outer surface and two layers of biocompatible material on the inner surface of neck region 104. Specifically, neck region 104 may be first covered on the outer surface by first graft portion 211 of graft tube 216, which is covered by third graft portion 213 of graft tube 216. Further, neck region 104 may be covered by bridge 240 (which may be a section of fourth graft portion 246 of second graft tube 245) and gap 243 may extend between third graft portion 213 of graft tube 216 and bridge 240. On the inner surface (i.e., on the interior of neck region 104), shunt 100 may be covered by second graft portion 212 of graft tube 216 and fifth graft portion 247 of second graft tube 245. Accordingly, shunt 100 of the shunt-graft assembly 210 may be covered at neck region 104 by five layers of biocompatible material.

Referring now to FIG. 12D, cross-section D of shunt-graft assembly 210 is illustrated. As is shown in FIG. 12D, second flared end region 106 of shunt 100 is covered on the outer surface and the inner surface by graft tube 216. Specifically, second flared end region 106 may be covered on the outer surface by first graft portion 211 of graft tube 216 and on the inner surface (i.e., on the interior of second flared end region 106) by second graft portion 212 of graft tube 216. Further, second graft tube 245 may be deposited over graft tube 216. Specifically, second flared end region 106 may be covered on the outer surface by fourth graft portion 246 of second graft tube 245, which may extend over first graft portion 211 of graft tube 216, and on the inner surface by fifth graft portion 247 of second graft tube 245, which may extend over second graft portion 212 of graft tube 216. Accordingly, shunt 100 of shunt-graft assembly 210 may be covered at second flared end region 106 by four layers of biocompatible material.

Bridge 240 may be deposited on shunt-graft assembly 210 in a manner similar to the method described in FIGS. 5A-10D. For example, shunt-graft assembly 210 may be placed within a funnel and advanced towards a reduced section of the funnel. Shunt-graft assembly 210 may then be inserted into an introducer tube, which may have a smaller diameter than the diameter of bridge 240. The introducer tube may then be inserted into a first end of bridge 240 such that all of second flared end region 106 and neck region 104 and a portion of first flared end region 102 are advanced into second graft tube 245. Upon removal of the introducer tube, first flared end region 102 and second flared end region 106 may expand radially to a diameter larger than the diameter of second graft tube 245, thereby engaging second graft tube 245 along the outer surface of the flared end regions in a manner that causes second graft tube 245 to expand in an unstressed and unwrinkled fashion. Preferably second graft tube 245 has a diameter larger than the dimeter of neck region 104, such that bridge 240 is created, with gap 243 between encapsulated neck region 104 and second graft tube 245. Bridge 240 may have first end 241, which may be disposed approximately half way up first flared end region 102, and second end 242, which may be disposed approximately half way up second flared end region 106.

After depositing fourth graft portion 246 of second graft tube 245 upon second flared end region 106, neck region 104, and a portion of flared end region 102, second graft tube 245 may be everted at one end and guided through an interior of shunt 100, using a plunger or other tool as described above. A mandrel similar to first mandrel portion 217 and second mandrel portion 219, described above and shown in FIGS. 7A and 7B, may be used to ensure fifth graft portion 247 is properly engaged with the inner surfaces of first flared end region 102, neck region 104, and second flared end region 106.

After depositing fifth graft portion 247 of second graft tube 245 upon the interior of shunt 100, forceps may be used to grasp the second end of second graft tube 245 and gentry pull the second end over first flared end region 102, thereby depositing sixth graft portion 248. Preferably, sixth graft portion 248 is deposited over first flared end region 102 such that it partially overlaps fourth graft portion 246, as shown in FIG. 12A.

After depositing sixth graft portion 248 of second graft tube 245 upon first flared end region, a flexible sleeve similar to flexible sleeve 231, described above and shown in FIG. 9A, may be positioned on the mandrel. Preferably, the flexible sleeve has a shape configured to receive shunt-graft assembly 210 including bridge 240 and the neck region of the flexible sleeve has a diameter corresponding to the diameter of bridge 240, such that gap 243 is not reduced. A compressor similar to compressor 232, described above and shown in FIG. 10A, may be positioned over the flexible sleeve. Preferably, compressor has a first half and a second half, each having an interior indentation sized and configured to receive the flexible sleeve.

To securely bond second graft tube 245 to graft tube 216, pressure may be applied to shunt-graft assembly 210 to achieve sintering, as described above. Preferably, heating the sintering assembly causes fourth graft portion 246, fifth graft portion 247, and sixth graft portion 248 to become sintered to shunt-graft assembly 210, except in neck region 104, such that gap 243, which may be unbonded, is created between neck region 104 and bridge 240. Additionally or alternatively, gap 243 may be filled with a biocompatible material, as shown in FIG. 2B. For example, a biocompatible material may be deposited on shunt-graft assembly 210 at the neck region either before or after fourth graft portion 246 of second graft tube 245 is deposited over neck region 104.

Figure 13:
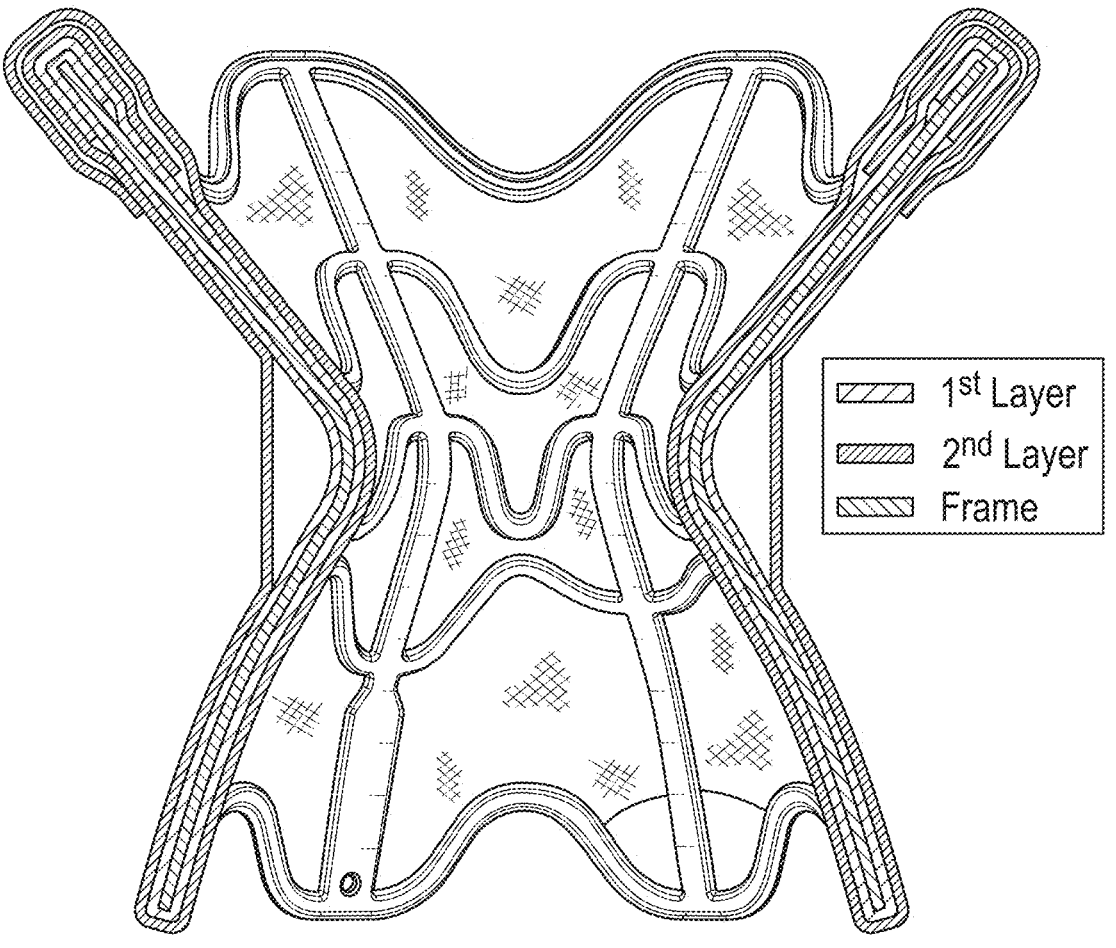
FIG. 13 illustrates another embodiment of a shunt-graft assembly having a bridge.

FIG. 13 illustrates another embodiment of a shunt-graft assembly including the bridge described above. In this embodiment, a single tube of biocompatible material may be used to encapsulate the frame and form the bridge. For example, the single tube may be wrapped twice, starting with one end at a location, e.g., the neck or near the end of one flange of the frame, using three eversions to lay down two complete wraps. In FIG. 13, the first complete wrap "1st Layer" is shown in blue, and the second wrap "2nd Layer", is shown in pink. In some embodiments, the neck region is sintered prior to the last eversion of the 2nd layer. In such embodiments, after the neck is sintered there will be 3 layers of material at the neck, pink and blue inside and only blue outside, all of which may be sintered together. The final end of the tube could then be everted and pulled back over the shunt. This layer will form the bridge described herein. In some embodiment, the bridge will not be sintered to the other layers at the smallest diameter portion of the neck so that the bridge remains free in the neck area. The bridge will be sintered at its ends where the ends contact the first layer of the wrap, shown in blue. By varying the gap in sintering at the neck the length and height of the bridge can be chosen.

Figure 14A:
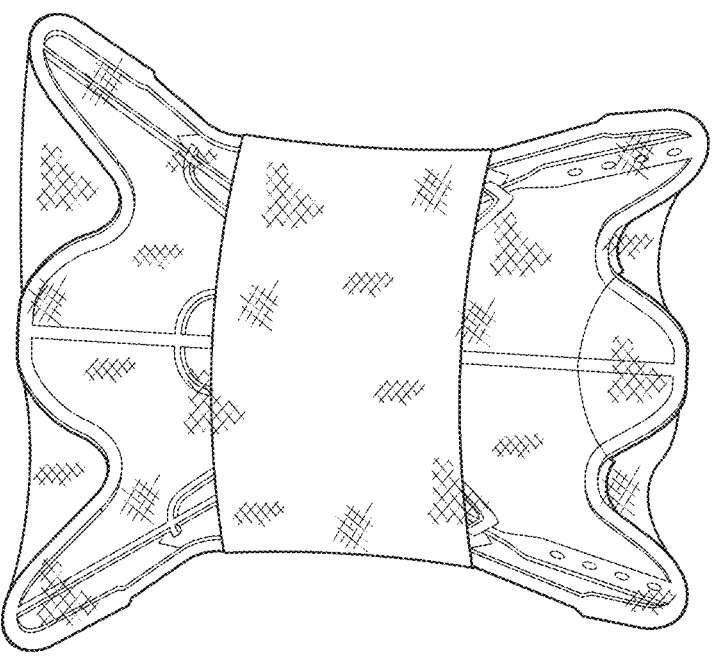
FIGS. 14A-14B illustrate images of the encapsulated stent of FIGS. 12A-12D.
Figure 14B:
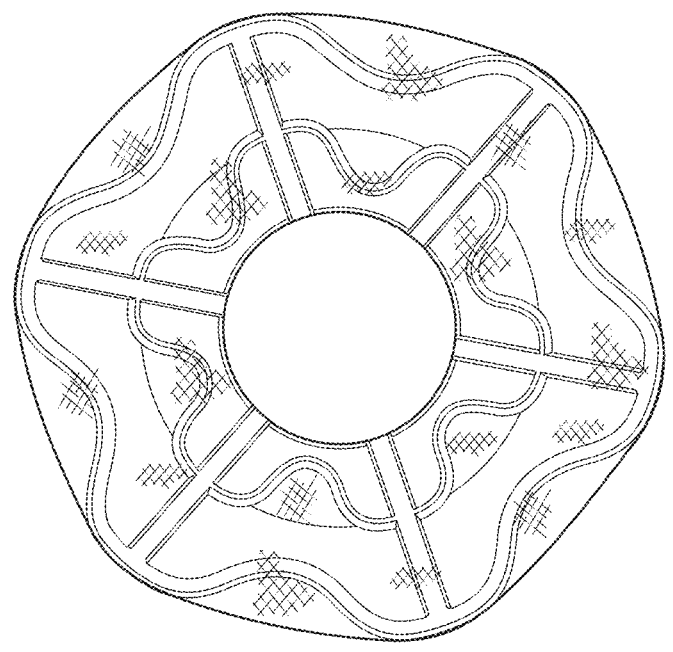

Referring now to FIGS. 14A and 14B, images of an exemplary encapsulated stent formed using the methods described in FIGS. 7A-10B and 12A-12D is shown. Specifically, FIG. 14A shows the first flared end region, the second flared end region, and the neck region of the encapsulated stent, with a bridge surrounding the neck region to create a larger outer diameter, the bridge configured to engage with the atrial septum. FIG. 14B shows the first flared end region and the neck region, which defines an inner diameter (or neck dimension) of the passageway through which blood flows.

As described above, the neck region of the interatrial shunt may be expanded and/or contracted in vivo so as to provide a suitable, and customized, flow of fluid through the device for each given patient, e.g., as further described in U.S. Pat. No. 10,898,698. Specifically, the frame of the shunt devices described herein, e.g., a metallic frame, may be heat treated during manufacture, such that the neck region of the shunt may be malleable at body temperature, e.g., mechanically expandable, and contracted when heated to a temperature above its martensitic finish temperature (MO. Moreover, the shunt device may be heat treated such that the neck region may be contracted from an expanded state by variable degrees, e.g., selected increments, depending on the temperature to which the frame of the shunt device is raised to. For example, the shunt orifice at the neck region of the shunt device may be expanded from a first diameter to a second diameter larger than the first diameter in vivo, e.g., via mechanical expansion by a balloon catheter, and thermally contracted in vivo from the second diameter to a third diameter larger than the first diameter by heating the frame of the shunt device to a predetermined temperature that is above its martensitic finish temperature (MO, but below its austenitic finish temperature (At). Accordingly, the multiphase shunt devices described herein may be contracted to a desired diameter that is larger than its heat-set austenitic configuration without having to be fully contracted, e.g., by heating the shunt device to a temperature above its austenitic finish temperature (At), and subsequently mechanically expanded to the desired diameter.

Figure 15:
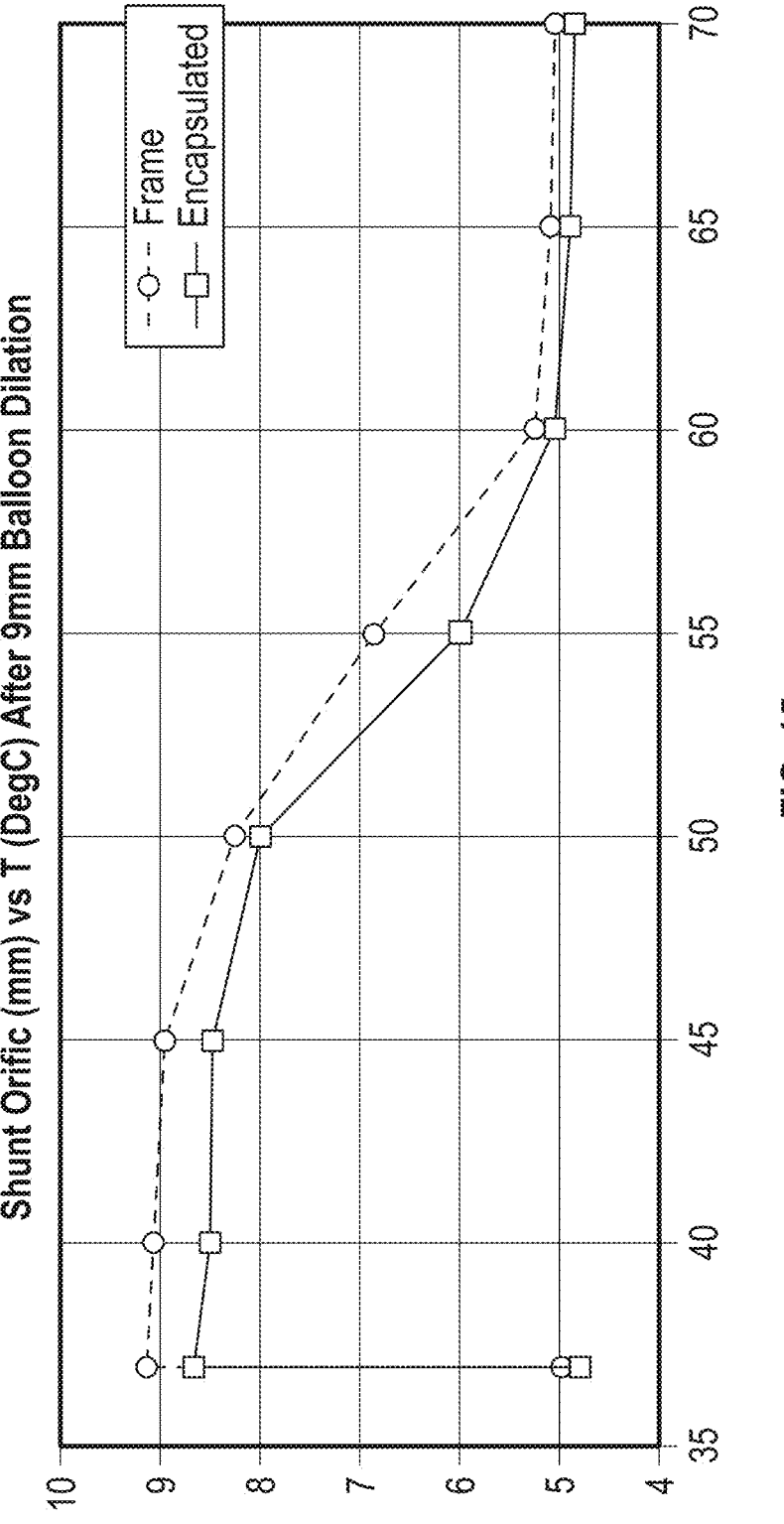
FIG. 15 is a graph illustrating incremental thermal contraction of the shunt orifice in accordance with the principles of the present disclosure.

Referring now to FIG. 15, a graph illustrating exemplary gradual, incremental contractions of the shunt orifices of a bare frame shunt device and an encapsulated shunt device, respectively, is provided. With reference to Table 1 copied below, as shown in FIG. 15, during a baseline phase of the respective shunt devices, in a water bath at body temperature, e.g., 37° C., the bare frame shunt device had an orifice diameter of 5.00 mm and the encapsulated shunt device has an orifice diameter of 4.80 mm. In this study, the austenitic finish temperature (At) of each shunt device was about 60° C. While the temperature of the shunt devices remained at 37° C., both shunt devices were expanded via a nominal 9 mm angioplasty balloon, such that the shunt orifice of the bare frame shunt device expanded to 9.10 mm, and the shunt orifice of the encapsulated shunt device was expanded to 8.65 mm. Following the expansion, the temperature of the water bath was slowly increased until reaching a temperature of 70° C., such that the respective shunt orifice diameters of each shunt device were recorded at 5° C. increments.

TABLE 1

| Phase of Shunt Device | Temperature (C.) | Orifice Diameter (mm) | |
|---|---|---|---|
| | | Bare Frame | Encapsulated |
| Baseline | 37 | 5.00 | 4.80 |
| After 9 mm Balloon Expansion | 37 | 9.10 | 8.65 |
| Heat-Activated Recovery | 40 | 9.05 | 8.50 |
| | 45 | 8.95 | 8.45 |
| | 50 | 8.25 | 8.00 |
| | 55 | 6.85 | 6.00 |
| | 60 | 5.25 | 5.05 |
| | 65 | 5.10 | 4.90 |
| | 70 | 5.05 | 4.85 |

As shown in Table 1, the data illustrates that heat-activated shape-memory recovery of the respective shunt devices to their heat-set baseline shunt orifice diameter may be achieved gradually as opposed to an all-or-none transition. Accordingly, by heating the shunt devices to a predetermined temperature above their respective martensitic finish temperatures (MO, but below their respective austenitic finish temperatures (At), the shunt orifice of the shunt devices may be selectively thermally contracted to a desired diameter between their respective baseline diameters and their respective fully balloon-expanded diameters.

As shown in FIG. 15, both shunt devices begin their recovery, e.g., contraction toward their respective baseline diameters from their respective 9 mm balloon-expanded diameters, at about 45° C., reaching halfway recovery, e.g., about 7 mm shunt orifice diameter, at about between 52° C. to 55° C., and complete recovery, e.g., their respective baseline diameters, at about 60° C. Moreover, after the temperature of the water bath exceeds the austenitic finish temperatures (At) of about 60° C., further contraction of the respective shunt devices may be minimal as the shunt orifices have essentially reached their respective baseline diameters. As will be understood by a person having ordinary skill in the art, the shunt devices having a bridge described herein also may be heat treated such that they may be selectively thermally contracted to diameters other than their heat-set austenitic configurations.

Accordingly, the shunt devices described herein, upon deployment at the interatrial shunt, may, for example, be temporarily balloon expanded in vivo to allow passage of a device such as, e.g., a MitraClip® system, through the passageway of the shunt device, and subsequently efficiently readjusted to a smaller desired diameter (larger than its fully recovered diameter) by heating the shunt device to a specific temperature below its austenitic finish temperatures (At), e.g., according to Table 1 above. For example, the shunt device may be heated by injecting a heated fluid, e.g., saline, via a catheter to the shunt device in vivo, until the desired temperature of the shunt device is achieved. Preferably, the saline may be heated to an initial temperature calculated based on, e.g., the injection rate of the saline through the catheter and/or a size/dimension of the catheter including, for example, the length of the catheter, the wall thickness of the catheter, the inner diameter of the fluid lumen of the catheter, and/or the outer diameter of the catheter, such that the saline is at the desired temperature when it is injected onto the shunt device at the interatrial septum, to account for any thermal loss between the catheter lumen and external factors such as the ambient air and/or the body temperature blood surrounding the catheter as the saline is injected through the catheter.

In addition, it is preferable to minimize dilution and washout of the heated saline as it is injected onto the shunt device in vivo. For example, an inflatable balloon, e.g., a semi-spherical 10-16 mm diameter balloon, may be delivered and positioned adjacent the distal end region of the shunt device, e.g., across the interatrial septum, and inflated to its expanded state to block blood flow through the shunt device during injection of the heated saline to the shunt device, e.g., via a large 8-14 Fr injection catheter having an outlet/port adjacent to the proximal end region of the shunt device, to thereby minimize dilution and washout of the heated saline. The large injection catheter permits rapid delivery of the heated saline, which further minimizes dilution and washout. Accordingly, an amount of heated saline must be injected through the catheter to first displace the entire volume within the fluid lumen of the injection catheter, as well as deliver enough heated saline to heat the shunt device to the desired temperature in vivo. Alternatively, an inflatable balloon may be delivered and positioned adjacent to the proximal region of the shunt device and inflated to its expanded state during injection of the heated saline to minimize dilution and washout of the heated saline. For example, a single injection catheter having an inflatable balloon disposed thereon at a position proximal to the injection ports of the injection catheter may be used to simultaneously inject heated saline to the shunt device and block blood flow through the shunt device.

In some embodiments, the distal tip of the injection catheter may include a temperature sensor configured to generate one or more signals indicative of the temperature of the heated fluid delivered within the shunt device, e.g., during injection of the heated saline. Accordingly, the user may terminate injection of heated saline through the catheter when the temperature of the heated fluid delivered within the shunt device reaches the desired temperature, and accordingly, the shunt device achieves the desired shunt orifice diameter. Additionally or alternatively, injection of heated saline through the catheter to the shunt device may be automated via a power injector fluidically coupled to the injection catheter, and operatively coupled to the temperature sensor. For example, the power injector may be programmed to automatically terminate heated saline injection when the signal received from the temperature sensor indicates that the temperature of the heated fluid delivered within the shunt device is at a predetermined desired temperature, e.g., for a predetermined time period.

In some embodiments, the power injector may include a heated syringe, which may be set to a temperature higher than the austenitic finish temperatures (At) of the shunt device at the interatrial septum. Accordingly, the power injector may be programmed to control the rate and duration of the injection of heated saline through the catheter based on the feedback signal from the temperature sensor indicative of the temperature of the shunt device. For example, the temperature of the saline within the shunt location may be increased by increasing the rate of injection, or conversely, decreased by decreasing injection rate, as cooling of the heated saline through the catheter is reduced by reducing the transit time of the heated saline through the catheter.

Accordingly, the power injector may be programmed to begin injection of heated saline through the catheter at a rapid rate to initially displace the body-temperature fluid within the catheter, followed by a slower injection rate as the temperature at the distal tip of the catheter measured by the temperature sensor rises. The power injector further may be programmed to modulate the injection rate to maintain the temperature of the heated fluid delivered within the shunt device, and accordingly the temperature of at least the middle region of the shunt device, for a predetermined time period, e.g., one or two seconds or less, to ensure that the shunt orifice diameter has thermally contracted to the desired size.

Although the middle region of the shunt device is described herein as being heated treated such that it may be heated to a target temperature above its martensitic finish temperature (MO, but below its austenitic finish temperatures (At) to be selectively contracted to a predetermined size, as will be understood by a person having ordinary skill in the art, the proximal and/or the distal end region of the shunt device in addition to or instead of the middle region may be similarly heated treated to permit selective thermal contraction of the respect end region.

Additional studies have shown that the "effective" austenitic finish temperature (At), i.e., the temperature required to return the shunt device to its heat-set austenitic configuration, of an ePTFE encapsulated shunt may be lower than the austenitic finish temperature (At) of the Nitinol frame, e.g., by about 5° C. This is theorized to be due to the ePTFE acting as an insulator to heat transfer to the Nitinol frame. Accordingly, to achieve a target effective austenitic finish temperature (At) of, e.g., 45-60° C., for an encapsulated shunt, the Nitinol frame may be heat treated to exhibit an austenitic finish temperature (At) of 50-65° C., prior to encapsulation. Moreover, the thickness of the encapsulation material may be selected to control the effective austenitic finish temperature (At) of an encapsulated shunt. For example, a first encapsulated shunt with a Nitinol frame having a first austenitic finish temperature (At) and a first encapsulation material thickness may have the same effective austenitic finish temperature (At) as a second encapsulated shunt with a Nitinol frame having a second austenitic finish temperature (At) higher than the first second austenitic finish temperature (At) of the first encapsulated shunt and a second encapsulation material thickness that is thicker than the first encapsulation material thickness of the first encapsulated shunt.

Figure 16:
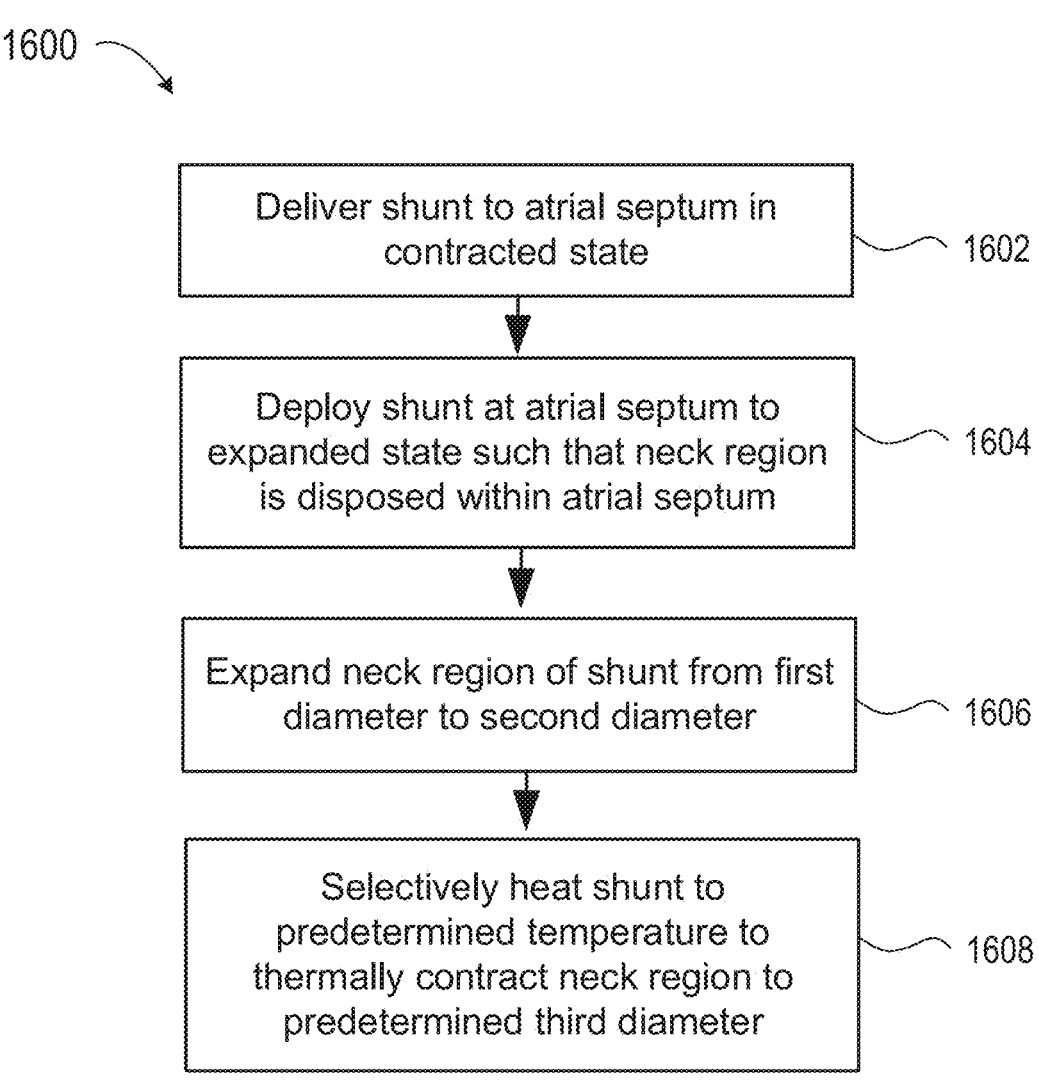
FIG. 16 is a flow chart illustrating exemplary method steps for treating a heart condition in accordance with the principles of the present disclosure.

Referring now to FIG. 16, exemplary method 1600 for treating a heart condition using the shunt devices describes herein is provided. At step 1602, the shunt may be delivered to the interatrial septum in its contracted state, using any of the delivery methods described above. For example, the shunt device may be delivered within a delivery sheath through the interatrial septum. As described above, the shunt device may have a diabolo shape, and may be heat treated during manufacture such that its proximal and distal end regions are self-expandable at body temperature, and its middle/neck region exhibits a martensitic finish temperature (MO, such that it is malleable at body temperature, and an austenitic finish temperature (At), above which it returns to its heat-set austenitic configuration. Moreover, the shunt device may be any one of a bare frame stent, an encapsulated shunt device, and/or may include a bridge, as described above.

At step 1604, the shunt device may be deployed to its expanded state at the interatrial septum such that its distal end region self-expands in a first atrium, its proximal end region self-expands in a second atrium, and the neck region is disposed within the interatrial septum. At step 1606, the neck region of the shunt device may be expanded, e.g., mechanically balloon-expanded, such that the shunt orifice at the neck region expands from a first diameter to a second diameter larger than the first diameter. For example, the second diameter may be selected to permit a medical device to pass therethrough, e.g., a MitraClip® system. Alternatively, the second diameter may be selected to permit blood flow therethrough at a predetermined flow rate to provide an initial therapy.

Accordingly, if/when the shunt orifice of the shunt device needs to be reduced, e.g., during the course of the therapy based on patient physiological response, at step 1608, the shunt device may be heated to a predetermined temperature below the austenitic finish temperature (At), e.g., in accordance with Table 1 above, to selectively thermally contract the shunt orifice at the neck region to a predetermined third diameter, e.g., a diameter that is smaller than the second diameter, but larger than the first diameter. For example, as described above, an injection catheter may be used to inject heated fluid, e.g., saline, to the shunt device in vivo to heat the shunt device to the desired temperature. When the shunt device reaches the desired temperature, and accordingly, the shunt orifice of the neck region reaches the desired size, the delivery sheath and the injection catheter may be removed from the patient leaving the shunt device implanted at the interatrial septum. Additionally or alternatively, other methods may be used to selectively thermally contract the shunt device in vivo such as, for example, applying a current to the shunt device via one or more electrodes, as described above. As will be understood by a person having ordinary skill in the art, if the desired shunt orifice size is the heat-set austenitic configuration, e.g., the first diameter, the shunt device may be heated to a temperature above the austenitic finish temperature (At).

While various illustrative embodiments of the invention are described above, it will be apparent to one skilled in the art that various changes and modifications may be made therein without departing from the invention. For example, although examples of the present devices are described as having two or three components, it should be understood that the present devices may include any suitable number of components that respectively include a self-expanding superelastic material or a malleable shape-memory material. The appended claims are intended to cover all such changes and modifications that fall within the true spirit and scope of the invention.

What is claimed is:

1. A method for making in vivo adjustments for shunting blood between a patient's first atrium and second atrium to treat a medical condition, the method comprising:

implanting an encapsulated shunt within a puncture in an atrial septum such that the encapsulated shunt transitions from a contracted delivery state to an expanded state wherein a first flared end region is disposed in the first atrium, a second flared end region is disposed in the second atrium, a neck region is disposed therebetween, and a bridge of biocompatible material extending from a first outer surface of the first flared end region to a second outer surface of the second flared end region engages the patient's atrial septum, wherein the encapsulated shunt defines a passageway to permit blood to flow from the first atrium to the second atrium via the passageway; and adjusting a diameter of the passageway in vivo to a different diameter while the bridge remains in contact with the atrial septum.

2. The method of claim 1, wherein adjusting the diameter comprises expanding the passageway such that the different diameter is larger than the diameter.

3. The method of claim 2, further comprising adjusting the different diameter to a third diameter smaller than the different diameter.

4. The method of claim 1, wherein adjusting the diameter comprises contracting the passageway such that the different diameter is smaller than the diameter.

5. The method of claim 1, wherein the neck region is malleable at body temperature and comprises NITINOL having an austenitic finish temperature (Af) between 45-65° C., and wherein the first flared end region and the second flared end region are superelastic at body temperature and comprise NITINOL having an austenitic finish temperature (Af) between 5-20° C.

6. The method of claim 1, wherein adjusting the diameter comprises mechanically expanding the passageway at the neck region in vivo to the different diameter.

7. The method of claim 1, wherein adjusting the diameter comprises thermally contracting the passageway at the neck region in vivo to the different diameter.

8. The method of claim 1, wherein the bridge defines an outer diameter larger than the diameter and the different diameter of the passageway.

9. The method of claim 8, wherein the outer diameter is between 7 and 14 mm.

10. The method of claim 8, wherein the bridge extends to form a gap between an inner surface of the bridge and an outer surface at the neck region.

11. The method of claim 10, wherein, when the diameter is adjusted in vivo, the gap is configured to change in size and the outer diameter is configured to remain the same diameter.

12. The method of claim 8, wherein the outer diameter of the bridge is configured to remain the same diameter while adjusting the diameter of the passageway to the different diameter.

13. The method of claim 1, wherein there is no gap between the bridge and the neck region.

14. The method of claim 1, wherein the bridge is integrally formed with biocompatible material that encapsulates the encapsulated shunt.

15. The method of claim 1, wherein the biocompatible material of the bridge is different from biocompatible material encapsulating the first flared end region, the second flared end region, and the neck region.

16. The method of claim 15, wherein the biocompatible material of the bridge is configured to permit tissue ingrowth and the biocompatible material encapsulating the first flared end region, the second flared end region, and the neck region is configured to inhibit tissue ingrowth.

17. The method of claim 15, wherein the biocompatible material of the bridge comprises a porosity selected to permit tissue ingrowth.

18. The method of claim 1, wherein the biocompatible material of the bridge has a porosity greater than the porosity of biocompatible material encapsulating the first flared end region, the second flared end region, and the neck region.

19. The method of claim 1, wherein the biocompatible material of the bridge has an internodal distance greater than the internodal distance of biocompatible material encapsulating the first flared end region, the second flared end region, and the neck region.

20. The method of claim 19, wherein the internodal distance of the bridge material is selected to permit tissue ingrowth while the internodal distance of the encapsulating material is selected to inhibit tissue ingrowth.

21. The method of claim 19, wherein the internodal distance of the bridge is greater than 30 microns while the internodal distance of the encapsulation is less than or equal to 30 microns.

22. The method of claim 19, wherein the internodal distance of the bridge material is in a range of 45-200 microns.

23. The method of claim 19, wherein the internodal distance of the bridge material is 60 microns while the internodal distance of the encapsulating material is 30 microns.

24. The method of claim 19, wherein the biocompatible material of the bridge and the biocompatible material encapsulating the first flared end region, the second flared end region, and the neck region are expanded polytetrafluoroethylene (ePTFE).

25. The method of claim 1, wherein the bridge is configured to remain engaged with the patient's atrial septum when the passageway is contracted.

26. The method of claim 1, wherein implanting the encapsulated shunt comprises percutaneously advancing the encapsulated shunt in the contracted delivery state toward the atrial septum in a delivery catheter and deploying the encapsulated shunt from the delivery catheter to implant the encapsulated shunt.

27. The method of claim 1, wherein the first flared end region and the second flared end region comprise a self-expanding superelastic material and the neck region comprises a malleable shape-memory material.

28. The method of claim 1, wherein the encapsulated shunt is configured to permit blood to flow from the first atrium to the second atrium via the passageway to treat heart failure.

29. The method of claim 1, wherein the encapsulated shunt is configured to permit blood to flow from the first atrium to the second atrium via the passageway to treat pulmonary hypertension.

\* \* \* \* \*